US008637663B2

(12) United States Patent
Raboisson et al.

(10) Patent No.: US 8,637,663 B2
(45) Date of Patent: Jan. 28, 2014

(54) MACROCYCLIC INHIBITORS OF HEPATITIS C VIRUS

(75) Inventors: Pierre Jean-Marie Bernard Raboisson, Rosieres (BE); Herman Augustinus De Kock, Arendonk (BE); David Craig McGowan, Brussels (BE); Wim Van De Vreken, Haasdonk (BE); Lili Hu, Putte (BE); Abdellah Tahri, Anderlecht (BE); Sandrine Marie Helene Vendeville, Woluwe-Saint-Pierre (BE)

(73) Assignee: Janssen R&D Ireland, Little Island Co Cork (IE)

( * ) Notice: Subject to any disclaimer, the term of this patent is extended or adjusted under 35 U.S.C. 154(b) by 739 days.

(21) Appl. No.: 12/441,812

(22) PCT Filed: Nov. 16, 2007

(86) PCT No.: PCT/EP2007/062436
§ 371 (c)(1),
(2), (4) Date: Mar. 18, 2009

(87) PCT Pub. No.: WO2008/059046
PCT Pub. Date: May 22, 2008

(65) Prior Publication Data
US 2010/0022578 A1    Jan. 28, 2010

(30) Foreign Application Priority Data

Nov. 17, 2006   (EP) ..................... 06124359

(51) Int. Cl.
*C07D 225/04*    (2006.01)

(52) U.S. Cl.
USPC ....................................... 540/461

(58) Field of Classification Search
USPC ....................................... 540/461
See application file for complete search history.

(56) References Cited

U.S. PATENT DOCUMENTS

| 5,087,876 | A | 2/1992 | Reiss et al. |
| 5,484,801 | A | 1/1996 | Al-Razzak et al. |
| 5,948,436 | A | 9/1999 | Al-Razzak et al. |
| 6,037,157 | A | 3/2000 | Norbeck et al. |
| 6,054,472 | A | 4/2000 | Armistead et al. |
| 6,344,465 | B1 | 2/2002 | Armistead et al. |
| 6,498,178 | B2 | 12/2002 | Stamos et al. |
| 7,511,157 | B2 * | 3/2009 | Bailey et al. .............. 548/537 |

FOREIGN PATENT DOCUMENTS

| WO | WO 94/14436 A1 | 7/1994 |
| WO | WO 95/07696 A1 | 3/1995 |
| WO | WO 95/09614 A1 | 4/1995 |
| WO | WO 97/40028 A1 | 10/1997 |
| WO | WO 98/40381 A1 | 9/1998 |
| WO | WO 00/09543 A2 | 2/2000 |
| WO | WO 00/56331 A1 | 9/2000 |
| WO | WO 00/59929 A1 | 10/2000 |
| WO | WO 02/18369 A2 | 3/2002 |
| WO | WO 03/087092 A2 | 10/2003 |
| WO | WO 2005/010029 A1 | 2/2005 |
| WO | WO 2005/073195 A2 | 8/2005 |
| WO | WO 2005/073216 A2 | 8/2005 |
| WO | WO 2007/014925 A1 | 2/2007 |
| WO | WO 2007/014926 A1 | 2/2007 |

OTHER PUBLICATIONS

Bodanszky, M., "Peptide Chemistry", 2nd Red.Ed., Springer-Verlag, Berlin, Germany (1993).

(Continued)

*Primary Examiner* — Shengjun Wang
(74) *Attorney, Agent, or Firm* — Andrea Jo Kamage

(57) ABSTRACT

Inhibitors of HCV replication of formula (I)

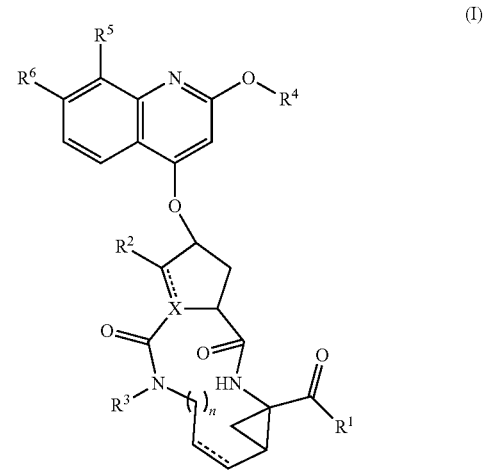

(I)

and the salts and stereoisomers thereof, wherein
each dashed line (represented by - - - - -) represents an optional double bond;
X is N, CH and where X bears a double bond it is C;
$R^1$ is —$OR^7$, —NH—$SO_2R^8$;
$R^2$ is hydrogen, and where X is C or CH, $R^2$ may also be $C_{1-6}$alkyl;
$R^3$ is hydrogen, $C_{1-6}$alkyl, $C_{1-6}$alkoxy$C_{1-6}$alkyl, $C_{3-7}$cycloalkyl;
n is 3, 4, 5, or 6;
$R^4$ is $C_{1-6}$alkyl or $C_{3-7}$cycloalkyl;
$R^5$ is hydrogen, halo, $C_{1-6}$alkyl, hydroxy, $C_{1-6}$alkoxy, polyhalo$C_{1-6}$alkyl;
$R^6$ is hydrogen, $C_{1-6}$alkoxy, mono- or di$C_{1-6}$alkylamino; or
$R^5$ and $R^6$ may form a 5- or 6-membered unsaturated or partially unsaturated ring, optionally comprising one or two selected from O, N and S;
$R^7$ is hydrogen; $C_{3-7}$cycloalkyl optionally substituted with $C_{1-6}$alkyl; or $C_{1-6}$alkyl optionally substituted with $C_{3-7}$cycloalkyl;
$R^8$ is $C_{3-7}$cycloalkyl optionally substituted with $C_{1-6}$alkyl; $C_{1-6}$alkyl optionally substituted with $C_{3-7}$cycloalkyl; or —$NR^{8a}R^{8b}$; $R^{8a}$ and $R^{8b}$ are $C_{1-6}$alkyl, or both may form a 5- or 6-membered saturated heterocyclic ring;
pharmaceutical compositions containing compounds (I) and processes for preparing compounds (I).

13 Claims, No Drawings

(56) References Cited

OTHER PUBLICATIONS

Dolby, et al., "Studies of the Synthesis of the B, C, and D Rings of Gibberellie Acid", J. Org. Chem. 36 (1971) 1277-1285.

Greene, "Protective Groups in Organic Chemistry", Wiley, John & Sons, New York (1999) and "The Peptides: Analysis, Synthesis, Biology", vol. 9, Academic Press, NY (1987) Title Page and Table of Contents.

Huang, et al., "Olefin Metathesis-Active Ruthenium Complexes Bearing a Nucleophilic Carbene Ligand" J.Am. Chem. Soc. 1999 121, p. 2674-2678.

Kingsbury, J., "A Recyclable Ru-Based Metathesis Catalyst", et al., J.Am. Chem. Soc. 1999, 121, p. 791-799.

Krchnak, V. et al., "Polymer-Supported Mitsunobu Ether Formation and its Use in Combinatorial Chemistry", Tetrahedron Letters, vol. 36, No. 35, p. 6193-6195, 1995.

Krieger, N., et al., "Enhancement of Hepatitis C Virus RNA Replication by Cell Culture-Adaptive Mutations", Journal of Virology, May 2001, pp. 4614-4624.

Landro, J., et la. "Mechanistic Role of an NS4A Peptide Cofactor with the Truneated NS3 Protease of Hepatitis C Virus: :Elucidation of the NS4A Stimulatory Effect via Kinetic Analysis and Inhibitor Mapping", Biochemistry 36, pp. 9340-9348 (1997).

Liu, Y., et al. "Use of a Fluorescence Plate Reader for Measuring Kinetic Parameters with Inner Filter Effect Correction", Analytical Biochemistry 267, pp. 331-335 (1999).

Lohmann, V., et al., "Replication of Subgenomic Hepatitis C Virus RNAs in a Hepatoma Cell Line", Science 285, 1999, pp. 110-113.

Miller, S., et al., "Application of Ring-Closing Metathesis to the Synthesis of Rigidified Amino Acids and Peptides", J. Am. Chem. Soc. 1996, 118, p. 9606-9614.

Mitsunobu, O., et al. "The Use of Diethyl Azodicarboxylate and Triphenylphospine in Synthesis and Transformation of Natural Products", Synthesis, Jan. 1-28 (1981).

Poliakov, "Expression and Purification of Recombinant Full-Length NS3 Protease-Helicase from a New Variant of Hepatitis C Virus", Prot Expression & Purification, 25, pp. 363-371, 2002.

Rano, Thomas A. and Chapman, Kevin T., "Solid Phase Synthesis of Aryl Ethers via the Mitsunobu Reaction", Tetrahedron Letters, vol. 36, No. 22, pp. 3789-3792, 1995.

Richter, L.S., Gadek, T.R., "A Surprising Observation about Mitsunobu Reactions in Solid Phase Synthesis", Tetrahedron Letters, vol. 35, No. 27, p. 4705-4706, 1994.

Rosenquist, et al., "Synthesis of Enantiomerically Pure trans-3,4-Substituted Cyclopentanois by Enzymatic Resolution", in Acta Chem. Scand. 46 (1992) 1127-1129.

Smith, E., et al. "Synthesis and Pharmacological Activity of Angiotensin converting Enzyme Inhibitors: N-(Mercaptoacy)-4-Substituted-(S)-Prolines", J. Med. Chem. 31, p. 875-885 (1988).

* cited by examiner

MACROCYCLIC INHIBITORS OF HEPATITIS C VIRUS

CROSS REFERENCE TO RELATED APPLICATIONS

This application claims priority of the benefits of the filing of PCT Application No. PCT/EP2007/062436, filed Nov. 16, 2007 and European Patent Application No. 06124359.8 filed Nov. 17, 2006. The complete disclosures of the aforementioned related U.S. patent application is/are hereby incorporated herein by reference for all purposes.

The present invention is concerned with macrocyclic compounds having inhibitory activity on the replication of the hepatitis C virus (HCV). It further concerns compositions comprising these compounds as active ingredients as well as processes for preparing these compounds and compositions.

Hepatitis C virus is the leading cause of chronic liver disease worldwide and has become a focus of considerable medical research. HCV is a member of the *Flaviviridae* family of viruses in the *hepacivirus* genus, and is closely related to the *flavivirus* genus, which includes a number of viruses implicated in human disease, such as dengue virus and yellow fever virus, and to the animal *pestivirus* family, which includes bovine viral diarrhea virus (BVDV). HCV is a positive-sense, single-stranded RNA virus, with a genome of around 9,600 bases. The genome comprises both 5' and 3' untranslated regions, which adopt RNA secondary structures, and a central open reading frame that encodes a single polyprotein. The polyprotein encodes ten gene products, which are generated from the precursor polyprotein by an orchestrated series of co- and posttranslational endoproteolytic cleavages mediated by both host and viral proteases. The viral structural proteins include the core nucleocapsid protein, and two envelope glycoproteins E1 and E2. The non-structural (NS) proteins encode some essential viral enzymatic functions (helicase, polymerase, protease), as well as proteins of unknown function. Replication of the viral genome is mediated by an RNA-dependent RNA polymerase, encoded by non-structural protein 5b (NS5B). In addition to the polymerase, the viral helicase and protease functions, both encoded in the bifunctional NS3 protein, have been shown to be essential for replication of HCV RNA. Next to the NS3 serine protease, HCV also encodes a metalloproteinase in the NS2 region.

Following the initial acute infection, a majority of infected individuals develop chronic hepatitis because HCV replicates preferentially in hepatocytes but is not directly cytopathic. In particular, the lack of a vigorous T-lymphocyte response and the high propensity of the virus to mutate appear to promote a high rate of chronic infection. Chronic hepatitis can progress to liver fibrosis leading to cirrhosis, end-stage liver disease, and HCC (hepatocellular carcinoma), making it the leading cause of liver transplantations.

There are 6 major HCV genotypes and more than 50 subtypes, which are geographically differently distributed. HCV type 1 is the predominant genotype in Europe and the US. The extensive genetic heterogeneity of HCV has important diagnostic and clinical implications, perhaps explaining difficulties in vaccine development and the lack of response to therapy.

Transmission of HCV can occur through contact with contaminated blood or blood products, for example following blood transfusion or intravenous drug use. The introduction of diagnostic tests used in blood screening has led to a downward trend in post-transfusion HCV incidence. However, given the slow progression to the end-stage liver disease, the existing infections will continue to present a serious medical and economic burden for decades.

Current HCV therapies are based on (pegylated) interferon-alpha (IFN-α) in combination with ribavirin. This combination therapy yields a sustained virologic response in more than 40% of patients infected by genotype 1 viruses and about 80% of those infected by genotypes 2 and 3. Beside the limited efficacy on HCV type 1, this combination therapy has significant side effects and is poorly tolerated in many patients. Major side effects include influenza-like symptoms, hematologic abnormalities, and neuropsychiatric symptoms. Hence there is a need for more effective, convenient and better tolerated treatments.

Recently, two peptidomimetic HCV protease inhibitors have gained attention as clinical candidates, namely BILN-2061 disclosed in WO 00/59929 and VX-950 disclosed in WO 03/87092. A number of similar HCV protease inhibitors have also been disclosed in the academic and patent literature. It has already become apparent that the sustained administration of BILN-2061 or VX-950 selects HCV mutants that are resistant to the respective drug, so called drug escape mutants. These drug escape mutants have characteristic mutations in the HCV protease genome, notably D168V, D168A and/or A156S. Accordingly, additional drugs with different resistance patterns will be required to provide failing patients with treatment options, and combination therapy with multiple drugs is likely to be the norm in the future, even for first line treatment.

Experience with HIV drugs, and with HIV protease inhibitors in particular, has further emphasized that sub-optimal pharmacokinetics and complex dosage regimes quickly result in inadvertent compliance failures. This in turn means that the 24 hour trough concentration (minimum plasma concentration) for the respective drugs in an HIV regime frequently falls below the $IC_{90}$ or $ED_{90}$ threshold for large parts of the day. It is considered that a 24 hour trough level of at least the $IC_{50}$, and more realistically, the $IC_{90}$ or $ED_{90}$, is essential to slow down the development of drug escape mutants. Achieving the necessary pharmacokinetics and drug metabolism to allow such trough levels provides a stringent challenge to drug design. The strong peptidomimetic nature of prior art HCV protease inhibitors, with multiple peptide bonds poses pharmacokinetic hurdles to effective dosing regimes.

There is a need for HCV inhibitors that may overcome the disadvantages of current HCV therapy such as side effects, limited efficacy, the emergence of resistance, and compliance failures.

The present invention concerns HCV inhibitors that are superior in one or more of the following pharmacological related properties, i.e. potency, decreased cytotoxicity, improved pharmacokinetics, improved resistance profile, acceptable dosage and pill burden. In addition, the compounds of the present invention have relatively low molecular weight and are easy to synthesize, starting from starting materials that are commercially available or readily available through art-known synthesis procedures.

WO 2005/010029 discloses aza-peptide macrocyclic Hepatitis C serine protease inhibitors. WO 2005/073216 and WO 2005/073195 describe series of linear and macrocyclic HCV protease inhibitors having a proline respectively cycloalkyl moiety. The compounds of the present invention have a specifically substituted quinolinyloxy fragment, linked to the proline or cycloalkyl moieties, which fragment is undisclosed in the cited references.

The present invention concerns inhibitors of HCV replication, which can be represented by formula (I):

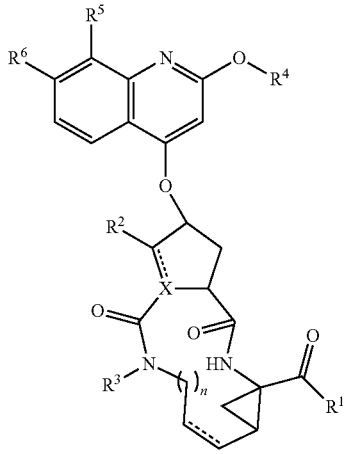

and the salts and stereoisomers thereof, wherein
each dashed line (represented by - - - - -) independently represents an optional double bond;
X is N, CH and where X bears a double bond it is C;
$R^1$ is —$OR^7$, —NH—$SO_2R^8$;
$R^2$ is hydrogen, and where X is C or CH, $R^2$ may also be $C_{1-6}$alkyl;
$R^3$ is hydrogen, $C_{1-6}$alkyl, $C_{1-6}$alkoxy$C_{1-6}$alkyl, $C_{3-7}$cycloalkyl;
n is 3, 4, 5, or 6;
$R^4$ is $C_{1-6}$alkyl or $C_{3-7}$cycloalkyl;
$R^5$ represents hydrogen, halo, $C_{1-6}$alkyl, hydroxy, $C_{1-6}$alkoxy, polyhalo$C_{1-6}$alkyl;
$R^6$ represents hydrogen, $C_{1-6}$alkoxy, mono- or di$C_{1-6}$alkylamino; or
$R^5$ and $R^6$ may optionally, together with the carbon atoms to which they are attached, form a 5- or 6-membered unsaturated or partially unsaturated ring, and wherein said ring may optionally comprise one or two heteroatoms selected from O, N and S;
$R^7$ is hydrogen; $C_{3-7}$cycloalkyl optionally substituted with $C_{1-6}$alkyl; or $C_{1-6}$alkyl optionally substituted with $C_{3-7}$cycloalkyl;
$R^8$ is $C_{3-7}$cycloalkyl optionally substituted with $C_{1-6}$alkyl; $C_{1-6}$alkyl optionally substituted with $C_{3-7}$cycloalkyl; or —$NR^{8a}R^{8b}$, wherein $R^{8a}$ and $R^{8b}$ are, each independently, $C_{1-6}$alkyl, or $R^{8a}$ and $R^{8b}$ together with the nitrogen to which they are attached form a 5- or 6-membered saturated heterocyclic ring.

The invention further relates to methods for the preparation of the compounds of formula (I), the addition salts and stereochemically isomeric forms thereof, and to intermediates used in these preparation methods.

The invention also relates to the compounds of formula (I) per se, the addition salts and stereochemically isomeric forms thereof, for use as a medicament. The invention further relates to pharmaceutical compositions comprising a carrier and an anti-virally effective amount of a compound of formula (I) as specified herein. The pharmaceutical compositions may comprise combinations of the aforementioned compounds with other anti-HCV agents. The invention further relates to the aforementioned pharmaceutical compositions for administration to a subject suffering from HCV infection.

The invention also relates to the use of a compound of formula (I), or an addition salt, or stereochemically isomeric forms thereof, for the manufacture of a medicament for inhibiting HCV replication. Alternatively, the invention relates to a method of inhibiting HCV replication in a warm-blooded animal, said method comprising the administration of an effective amount of a compound of formula (I), or an addition salt, or a stereochemically isomeric form thereof.

As used in the foregoing and hereinafter, the following definitions apply, unless otherwise noted.

The term halo is generic to fluoro, chloro, bromo and iodo.

The term "polyhalo$C_{1-6}$alkyl" is defined as mono- or polyhalo substituted $C_{1-6}$alkyl, in particular $C_{1-6}$alkyl substituted with up to one, two, three, four, five, six, or more halo atoms, such as methyl or ethyl with one or more fluoro atoms, for example, difluoromethyl, trifluoromethyl, trifluoroethyl. Preferred is trifluoromethyl. Also included are perfluoro$C_{1-6}$alkyl groups, which are $C_{1-6}$alkyl groups wherein all hydrogen atoms are replaced by fluoro atoms, e.g. pentafluoroethyl. In case more than one halogen atom is attached to an alkyl group within the definition of polyhalo$C_{1-6}$alkyl, the halogen atoms may be the same or different.

As used herein "$C_{1-4}$alkyl" as a group or part of a group defines straight or branched chain saturated hydrocarbon radicals having from 1 to 4 carbon atoms such as for example methyl, ethyl, 1-propyl, 2-propyl, 1-butyl, 2-butyl, 2-methyl-1-propyl; "$C_{1-6}$alkyl" encompasses $C_{1-4}$alkyl radicals and the higher homologues thereof having 5 or 6 carbon atoms such as, for example, 1-pentyl, 2-pentyl, 3-pentyl, 1-hexyl, 2-hexyl, 2-methyl-1-butyl, 2-methyl-1-pentyl, 2-ethyl-1-butyl, 3-methyl-2-pentyl, and the like. Of interest amongst $C_{1-6}$alkyl is $C_{1-4}$alkyl.

The term "alkenyl" as a group or part of a group defines straight and branched chained hydrocarbon radicals having saturated carbon-carbon bonds and at least one (or preferably one) double bond. The term "alkenyl" may refer to hydrocarbon radicals as specified above having a varying number of carbon atoms, e.g. from 2-6, 3-6, 2-4, 3-4, etc. The term "$C_{5-8}$alkenyl", as used herein as a group or part of a group defines straight and branched chained hydrocarbon radicals having saturated carbon-carbon bonds and at least one (or preferably one) double bond, and having from 5 to 8 carbon atoms, such as, for example, 2-pentenyl, 3-pentenyl, 2-hexenyl, 3-hexenyl, 4-hexenyl, 2-methyl-2-butenyl, 2-methyl-2-pentenyl, 2-heptenyl, 3-heptenyl, 1-octenyl, 2-octenyl, 3-octenyl, 4-octenyl, and the like.

$C_{3-7}$cycloalkyl is generic to cyclopropyl, cyclobutyl, cyclopentyl, cyclohexyl and cycloheptyl.

$C_{1-6}$alkoxy means $C_{1-6}$alkyloxy wherein $C_{1-6}$alkyl is as defined above.

As used herein before, the term (=O) or oxo forms a carbonyl moiety when attached to a carbon atom, a sulfoxide moiety when attached to a sulfur atom and a sulfonyl moiety when two of said terms are attached to a sulfur atom. Whenever a ring or ring system is substituted with an oxo group, the carbon atom to which the oxo is linked is a saturated carbon.

It should be noted that the radical positions on any molecular moiety used in the definitions may be anywhere on such moiety as long as it is chemically stable. When any variable occurs more than one time in any moiety, each definition is independent. Radicals used in the definitions of the variables include all possible isomers unless otherwise indicated. For instance pyridyl includes 2-pyridyl, 3-pyridyl and 4-pyridyl; pentyl includes 1-pentyl, 2-pentyl and 3-pentyl.

Whenever used hereinafter, the term "compounds of formula (I)", or "the present compounds" or similar terms, it is meant to include the compounds of formula (I), the addition salts thereof; and the stereochemically isomeric forms thereof.

The compounds of formula (I) have several centers of chirality and exist as stereochemically isomeric forms. The term "stereochemically isomeric forms" as used herein defines all the possible compounds made up of the same atoms bonded by the same sequence of bonds but having different three-dimensional structures which are not interchangeable, which the compounds of formula (I) may possess. With reference to the instances where (R) or (S) is used to designate the absolute configuration of a chiral atom within a substituent, the designation is done taking into consideration the whole compound and not the substituent in isolation.

Unless otherwise mentioned or indicated, the chemical designation of a compound encompasses the mixture of all possible stereochemically isomeric forms, which said compound might possess. Said mixture may contain all diastereomers and/or enantiomers of the basic molecular structure of said compound. All stereochemically isomeric forms of the compounds of the present invention both in pure form or mixed with each other are intended to be embraced within the scope of the present invention. Pure stereoisomeric forms of the compounds and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i.e. minimum 80% of one isomer and maximum 20% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms "enantiomerically pure" and "diastereomerically pure" should be understood in a similar way, but then having regard to the enantiomeric excess, and the diastereomeric excess, respectively, of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The diastereomeric racemates of the compounds of formula (I) can be obtained separately by conventional methods. Appropriate physical separation methods that may advantageously be employed are, for example, selective crystallization and chromatography, e.g. column chromatography.

For some of the compounds of formula (I), or their salts, as well as intermediates used in the preparation thereof, the absolute stereochemical configuration was not experimentally determined. A person skilled in the art is able to determine the absolute configuration of such compounds using art-known methods such as, for example, X-ray diffraction.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

For therapeutic use, salts of the compounds of formula (I) are those wherein the counter-ion is pharmaceutically acceptable, which salts can be referred to as pharmaceutically acceptable acid and base addition salts. However, salts of acids and bases that are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove are meant to comprise the therapeutically active non-toxic acid and base addition salt forms which the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium, and the like salts; salts with organic bases, e.g. the benzathine, N-methyl-D-glucamine, hydrabamine salts, and salts with amino acids such as, for example, arginine, lysine, and the like.

The term "addition salt" or "salt", as used herein also is meant to comprise the solvates, which the compounds of formula (I) as well as the (non-solvate) salts thereof, are able to form. Such solvates are for example hydrates, alcoholates, e.g. methanolates, ethanolates, propanolates, and the like. Preferred are solvates that are pharmaceutically acceptable. Hence the invention also encompasses the pharmaceutically acceptable solvates of the compounds of formula (I) as specified herein.

Some of the compounds of formula (I) may also exist in their tautomeric form. Such forms, although not explicitly indicated in the above formula, are intended to be included within the scope of the present invention.

As mentioned above, the compounds of formula (I) have several asymmetric centers. In order to more efficiently refer to each of these asymmetric centers, the numbering system as indicated in the following structural formula will be used.

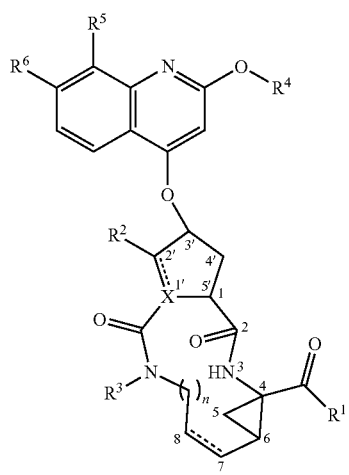

(I)

Asymmetric centers are present at positions 1, 4 and 6 of the macrocycle as well as at the carbon atom 3' in the 5-membered ring, carbon atom 2' when the R² substituent is $C_{1-6}$alkyl, and at carbon atom 1' when X is CH. Each of these asymmetric centers can occur in their R or S configuration.

The stereochemistry at position 1 preferably corresponds to that of an L-amino acid configuration, i.e. that of L-proline.

When X is CH, the two carbonyl groups substituted at positions 1' and 5' of the cyclo-pentane ring preferably are in a trans configuration. The carbonyl substituent at position 5' preferably is in that configuration that corresponds to an L-proline configuration. The carbonyl groups substituted at positions 1' and 5' preferably are as depicted below in the structure of the following formula

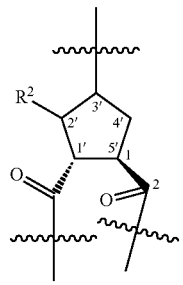

The compounds of formula (I) include a cyclopropyl group as represented in the structural fragment below:

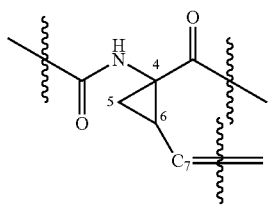

wherein $C_7$ represents the carbon at position 7 and carbons at position 4 and 6 are asymmetric carbon atoms of the cyclopropane ring.

Notwithstanding other possible asymmetric centers at other segments of the compounds of formula (I), the presence of these two asymmetric centers means that the compounds can exist as mixtures of diastereomers, such as the diastereomers of compounds of formula (I) wherein the carbon at position 7 is configured either syn to the carbonyl or syn to the amide as shown below.

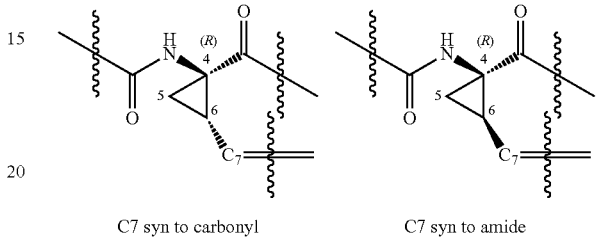

C7 syn to carbonyl        C7 syn to amide

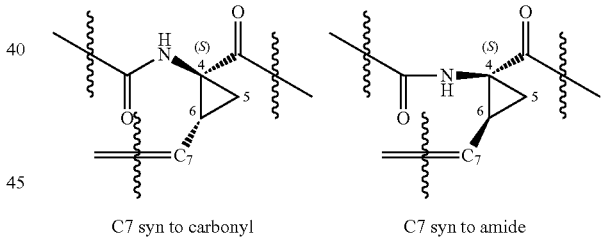

C7 syn to carbonyl        C7 syn to amide

One embodiment concerns compounds of formula (I) wherein the carbon at position 7 is configured syn to the carbonyl. Another embodiment concerns compounds of formula (I) wherein the configuration at the carbon at position 4 is R. A specific subgroup of compounds of formula (I) are those wherein the carbon at position 7 is configured syn to the carbonyl and wherein the configuration at the carbon at position 4 is R.

The compounds of formula (I) may include as well a proline residue (when X is N) or a cyclopentyl or cyclopentenyl residue (when X is CH or C). Preferred are the compounds of formula (I) wherein the substituent at the 1 (or 5') position and the substituent at position 3' are in a trans configuration. Of particular interest are the compounds of formula (I) wherein position 1 has the configuration corresponding to L-proline and the substituent at position 3' is in a trans configuration in respect of position 1. Preferably the compounds of formula (I) have the stereochemistry as indicated in the structures of formulae (I-a) and (I-b) below:

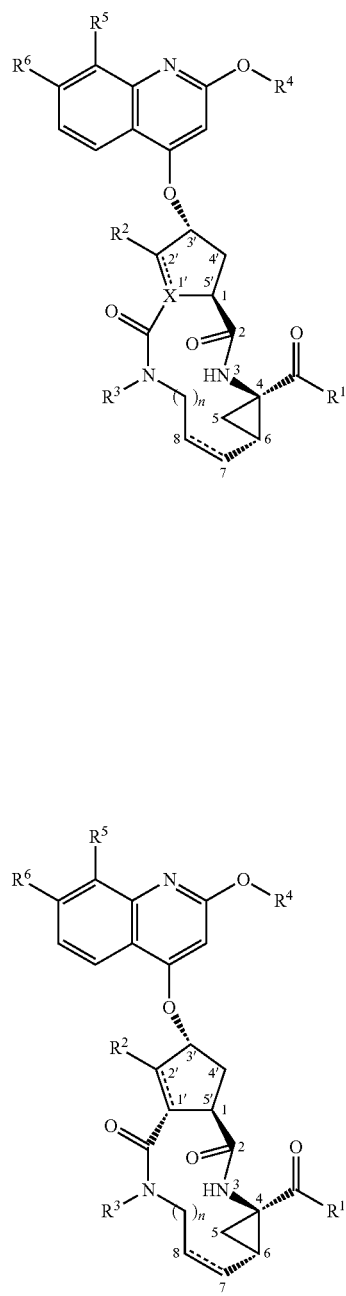

One embodiment of the present invention concerns compounds of formula (I) or of formula (I-a) or of any subgroup of compounds of formula (I), wherein one or more of the following conditions apply:

(a) $R^2$ is hydrogen;

(b) X is nitrogen;

(c) a double bond is present between carbon atoms 7 and 8.

One embodiment of the present invention concerns compounds of formula (I) or of formulae (I-a), (I-b), or of any subgroup of compounds of formula (I), wherein, where applicable, one or more of the following conditions apply:

(a) $R^2$ is hydrogen;

(b) X is CH;

(c) a double bond is present between carbon atoms 7 and 8.

Particular subgroups of compounds of formula (I) are those represented by the following structural formulae:

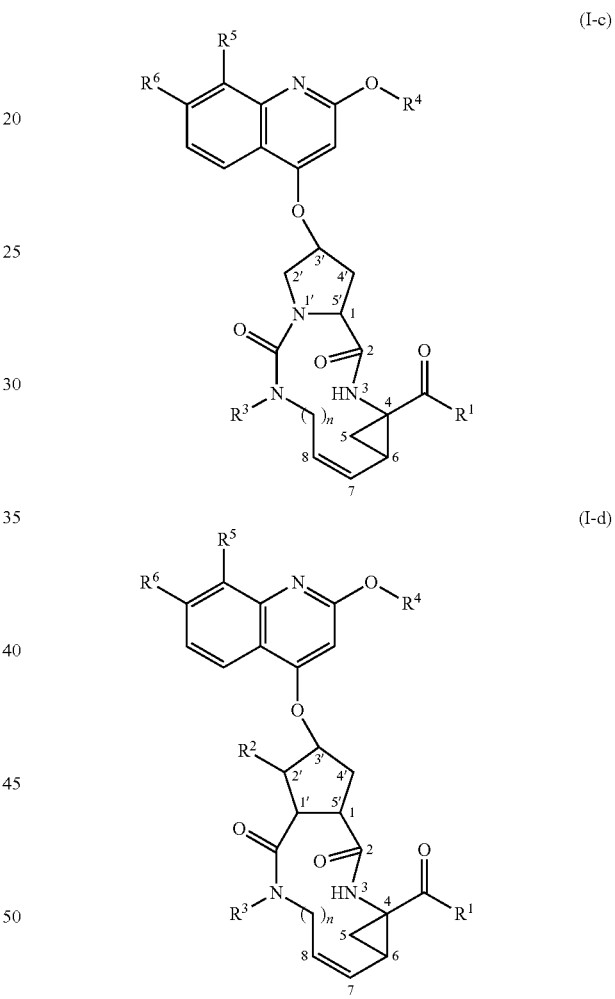

Amongst the compounds of formula (I-c) and (I-d), those having the stereochemical configuration of the compounds of formulae (I-a), and (I-b), respectively, are of particular interest.

The double bond between carbon atoms 7 and 8 in the compounds of formula (I), or in any subgroup of compounds of formula (I), may be in a cis or in a trans configuration. Preferably the double bond between carbon atoms 7 and 8 is in a cis configuration, as depicted in formulae (I-c) and (I-d).

A double bond between carbon atoms 1' and 2' may be present in the compounds of formula (I), or in any subgroup of compounds of formula (I), as depicted in formula (I-e) below.

(I-e)
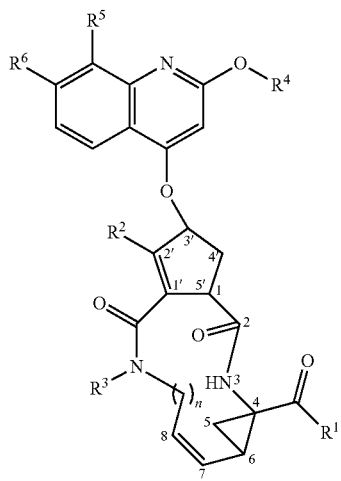

(I-h)
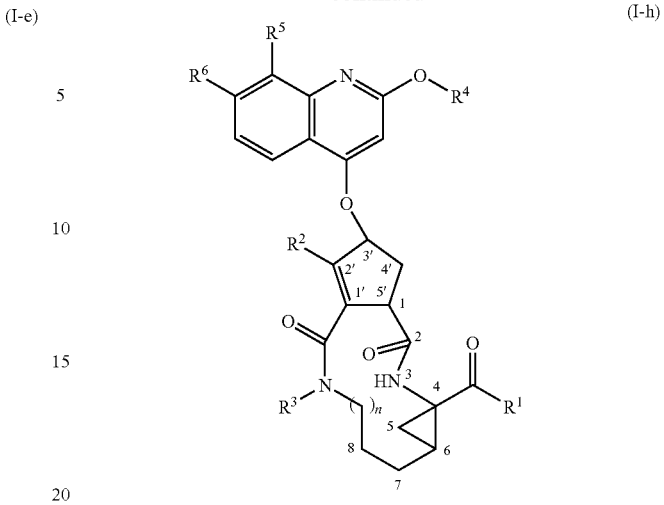

Other particular subgroups of compounds of formula (I) are those represented by the following structural formulae:

(I-f)
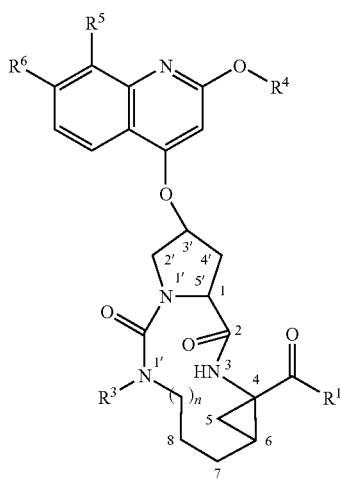

(I-g)
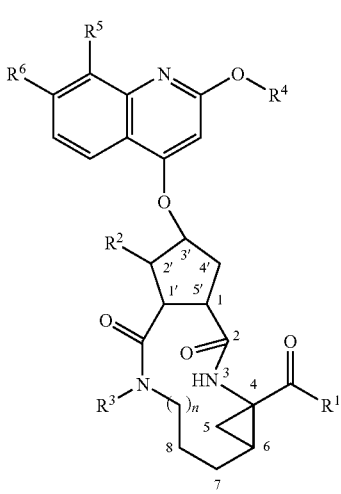

Amongst the compounds of formula (I-f), (I-g) or (I-h), those having the stereochemical configuration of the compounds of formulae (I-a) or (I-b) are of particular interest.

In the compounds of formula (I-a), (I-b), (I-c), (I-d), (I-e), (I-f), (I-g) and (I-h), where applicable, X, n, $R^1$, $R^2$, $R^3$, $R^4$, $R^5$, and $R^6$ are as specified in the definitions of the compounds of formula (I) or in any of the subgroups of compounds of formula (I) specified herein.

It is to be understood that the above defined subgroups of compounds of formula (I-a), (I-b), (I-c), (I-d), (I-e), (I-f), (I-g) or (I-h), as well as any other subgroup defined herein, are meant to also include stereochemically isomeric forms of such compounds and to also comprise any addition salts.

When n is 3, the moiety —$CH_2$— bracketed by "n" corresponds to propanediyl in the compounds of formula (I) or in any subgroup of compounds of formula (I). When n is 4, the moiety —$CH_2$— bracketed by "n" corresponds to butanediyl in the compounds of formula (I) or in any subgroup of compounds of formula (I). When n is 5, the moiety —$CH_2$— bracketed by "n" corresponds to pentanediyl in the compounds of formula (I) or in any subgroup of compounds of formula (I). When n is 6, the moiety —$CH_2$— bracketed by "n" corresponds to hexanediyl in the compounds of formula (I) or in any subgroup of compounds of formula (I). Particular subgroups of the compounds of formula (I) are those compounds wherein n is 4 or 5.

Embodiments of the invention are compounds of formula (I) or any of the subgroups of compounds of formula (I) wherein
  (a) $R^1$ is —$OR^7$, in particular wherein $R^7$ is $C_{1-6}$alkyl, such as methyl, ethyl, or tert-butyl (or t.butyl), or preferably wherein $R^7$ is hydrogen;
  (b) $R^1$ is —$NHS(=O)_2R^8$, in particular wherein $R^8$ is $C_{1-6}$alkyl or $C_{3-7}$cycloalkyl, e.g. wherein $R^8$ is methyl or cyclopropyl; or wherein $R^1$ is —$NHS(=O)_2R^8$ wherein $R^8$ is cyclopropyl;
  (c) $R^1$ is —$NHS(=O)_2R^8$, in particular wherein $R^8$ is $C_{3-7}$cycloalkyl substituted with $C_{1-6}$alkyl, preferably wherein $R^8$ is cyclopropyl, cyclobutyl, cyclopentyl, or cyclohexyl, each of which is substituted with $C_{1-4}$alkyl, i.e. with methyl, ethyl, propyl, isopropyl, butyl, tert-butyl, or isobutyl; or
  (d) $R^1$ is —$NHS(=O)_2R^8$, wherein in particular $R^8$ is —$NR^{8a}R^{8b}$, wherein $R^{8a}$ and $R^{8b}$ are, each independently $C_{1-6}$alkyl; or $R^1$ is —$NHS(=O)_2R^8$ wherein $R^{8a}$ and $R^{8b}$ together with the nitrogen to which they are attached form a 5- or 6-membered nitrogen-containing saturated heterocyclic ring, which ring may further contain a O, S, or N atom, which N-atom may bear a hydrogen atom or may bear a $C_{1-6}$alkyl or $C_{1-6}$alkylcarbonyl group; such as, e.g. pyrrolidinyl, piperidinyl, morpholinyl, piperazinyl, 4-$C_{1-6}$alkylpiperazinyl, or 4-$C_{1-6}$alkylcarbonylpiperazinyl;

(e) $R^1$ is —NHS(=O)$_2R^8$, wherein $R^8$ in particular is cyclopropyl substituted with $C_{1-4}$alkyl, i.e. cyclopropyl substituted with methyl, ethyl, propyl, or with isopropyl;

(f) $R^1$ is —NHS(=O)$_2R^8$, wherein in particular $R^8$ is 1-methylcyclopropyl (or 1-methyl-1-cyclopropyl).

Further embodiments of the invention are compounds of formula (I) or any of the subgroups of compounds of formula (I) wherein
(a) $R^2$ is hydrogen;
(b) $R^2$ is $C_{1-6}$alkyl, in particular methyl.

Embodiments of the invention are compounds of formula (I) or any of the subgroups of compounds of formula (I) wherein
(a) X is N, C(X being linked via a double bond) or CH(X being linked via a single bond) and $R^2$ is hydrogen;
(b) X is C(X being linked via a double bond) and $R^2$ is $C_{1-6}$alkyl, preferably methyl.

Further embodiments of the invention are compounds of formula (I) or any of the subgroups of compounds of formula (I) wherein
(a) $R^3$ is hydrogen;
(b) $R^3$ is $C_{1-6}$alkyl;
(c) $R^3$ is $C_{1-6}$alkoxy$C_{1-6}$alkyl or $C_{3-7}$cycloalkyl.

Preferred embodiments of the invention are compounds of formula (I) or any of the subgroups of compounds of formula (I) wherein $R^3$ is hydrogen or $C_{1-6}$alkyl; or $R^3$ is hydrogen or methyl; or $R^3$ is $C_{1-4}$alkyl; or $R^3$ is methyl.

Embodiments of the invention are compounds of formula (I) or any of the subgroups of compounds of formula (I) wherein $R^4$ is $C_{1-4}$alkyl; or wherein $R^4$ is methyl, ethyl, propyl, isopropyl, butyl, isobutyl, sec-butyl, tert-butyl, 1-methyl-butyl, 2-methyl-butyl, 3-methyl-butyl, 1,2-dimethyl-propyl, pentyl, 1-methyl-pentyl, 2-methyl-pentyl, 3-methyl-pentyl, 4-methyl-pentyl, 1,1-dimethyl-butyl, 1,2-dimethyl-butyl, 1,3-dimethyl-butyl, 2,2-dimethyl-butyl, 3,3-dimethyl-butyl, 1,1,2-trimethyl-propyl, 1,2,2-trimethyl-propyl, or hexyl. In one embodiment, $R^4$ is methyl, ethyl, propyl or isopropyl. In another embodiment $R^4$ is ethyl.

Embodiments of the invention are compounds of formula (I) or any of the subgroups of compounds of formula (I) wherein $R^5$ is hydrogen, halo, $C_{1-6}$alkyl, or polyhalo-$C_{1-6}$alkyl; or wherein $R^5$ is hydrogen, $C_{1-4}$alkyl, or halo; or wherein $R^5$ is hydrogen, methyl, ethyl, isopropyl, tert-butyl, fluoro, chloro, bromo, or trifluoromethyl.

Embodiments of the invention are compounds of formula (I) or any of the subgroups of compounds of formula (I) wherein $R^6$ is hydrogen, $C_{1-6}$alkoxy, or di$C_{1-6}$alkylamino; or wherein $R^6$ is hydrogen, methoxy, or dimethylamino; or wherein $R^6$ is hydrogen or methoxy.

Embodiments of the invention are compounds of formula (I) or any of the subgroups of compounds of formula (I) wherein $R^5$ and $R^6$, together with the carbon atoms to which they are attached, form a 5- or 6-membered unsaturated or partially unsaturated ring, and wherein said ring may optionally comprise one or two heteroatoms selected from O and N. One embodiment concerns compounds of formula (I) or any of the subgroups of compounds of formula (I), wherein $R^5$ and $R^6$, together with the carbon atoms to which they are attached, form a 5-membered partially unsaturated ring, wherein the unsaturation is between the carbon atoms bearing $R^5$ and $R^6$, the remainder of the ring is saturated, and said ring comprises one or two oxygen ring atoms. One particular embodiment concerns those compounds of formula (I) or any of the subgroups of compounds of formula (I) wherein $R^5$ and $R^6$, together with the quinoline moiety to which they are attached, form a ring system selected from:

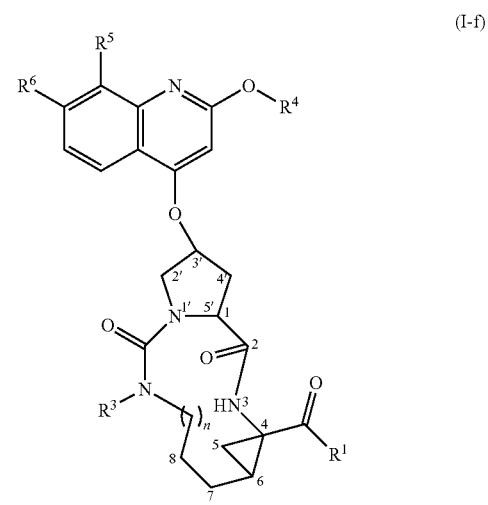

(I-f)

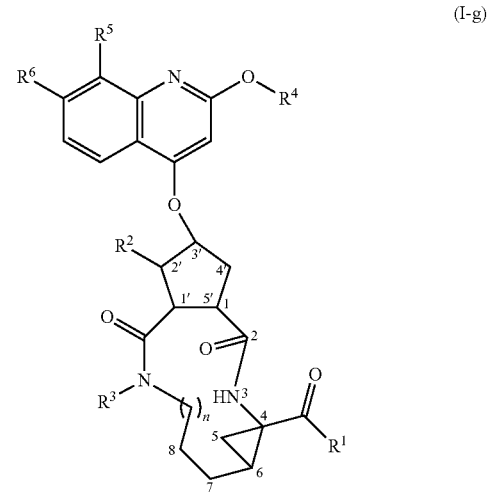

(I-g)

The compounds of formula (I) consist of three building blocks P1, P2, P3. Building block P1 further contains a P1' tail. The carbonyl group marked with an asterisk in compounds (I-i) and (I-j) below may be part of either building block P2 or of building block P3. For reasons of chemistry, building block P2 of the compounds of formula (I) wherein X is C incorporates the carbonyl group attached to the position 1'.

The linking of building blocks P1 with P2, P2 with P3, and P1 with P1' (when $R^1$ is —NH—SO$_2R^8$) involves forming an amide bond. The linking of blocks P1 and P3 involves double bond formation. The linking of building blocks P1, P2 and P3 to prepare compounds (I-i) or (I-j) can be done in any given sequence. One of the steps involves a cyclization whereby the macrocycle is formed.

Represented herebelow are compounds (I-i) which are compounds of formula (I) wherein carbon atoms C7 and C8 are linked by a double bond, and compounds (I-j) which are compounds of formula (I) wherein carbon atoms C7 and C8 are linked by a single bond. The compounds of formula (I-j) can be prepared from the corresponding compounds of formula (I-i) by reducing the double bond in the macrocycle.

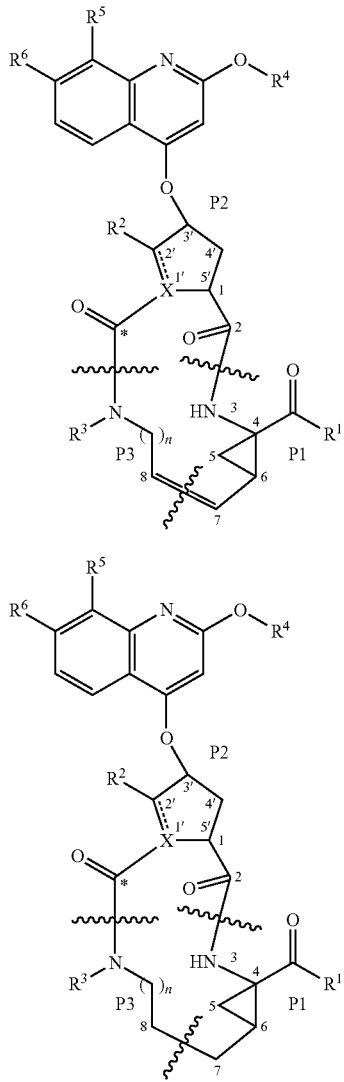

It should be noted that in compounds of formula (I-c), the amide bond formation between blocks P2 and P3 might be accomplished at two different positions of the urea fragment. A first amide bond encompasses the nitrogen of the pyrrolidine ring and the adjacent carbonyl (marked with an asterisk). An alternative second amide bond formation involves the reaction of the asterisked carbonyl with an —NHR³ group. Both amide bond formations between building blocks P2 and P3 are feasible.

The synthesis procedures described hereinafter are meant to be applicable for as well the racemates, stereochemically pure intermediates or end products, or any stereoisomeric mixtures. The racemates or stereochemical mixtures may be separated into stereoisomeric forms at any stage of the synthesis procedures. In one embodiment, the intermediates and end products have the stereochemistry specified above in the compounds of formula (I-a) and (I-b).

In order to simplify the structural representation of the compounds of formula (I) or the intermediates, the group

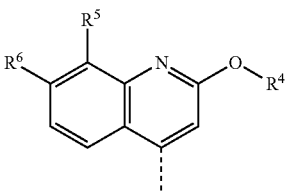

is represented by $R^9$ and the dotted line represents the bond linking said group $R^9$ to the remainder of the molecule.

In one embodiment, compounds (I-i) are prepared by first forming the amide bonds and subsequent forming the double bond linkage between P3 and P1 with concomitant cyclization to the macrocycle.

In a preferred embodiment, compounds (I) wherein the bond between $C_7$ and $C_8$ is a double bond, which are compounds of formula (I-i), as defined above, may be prepared as outlined in the following reaction scheme:

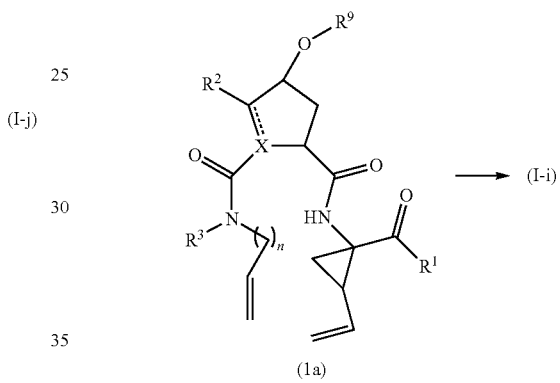

Formation of the macrocycle can be carried out via an olefin metathesis reaction in the presence of a suitable metal catalyst such as e.g. the Ru-based catalyst reported by Miller, S. J., Blackwell, H. E., Grubbs, R. H. J. Am. Chem. Soc. 118, (1996), 9606-9614; Kingsbury, J. S., Harrity, J. P. A., Bonitatebus, P. J., Hoveyda, A. H., J. Am. Chem. Soc. 121, (1999), 791-799; and Huang et al., J. Am. Chem. Soc. 121, (1999), 2674-2678; for example a Hoveyda-Grubbs catalyst.

Air-stable ruthenium catalysts such as bis(tricyclohexylphosphine)-3-phenyl-1H-inden-1-ylidene ruthenium chloride (Neolyst M1®) or bis(tricyclohexylphosphine)-[(phenylthio)methylene]ruthenium (IV) dichloride can be used. Other catalysts that can be used are Grubbs first and second generation catalysts, i.e. Benzylidene-bis(tricyclohexylphosphine)dichlororuthenium and (1,3-bis-(2,4,6-trimethylphenyl)-2-imidazolidinylidene)dichloro(phenylmethylene)-(tricyclohexylphosphine)ruthenium, respectively. Of particular interest are the Hoveyda-Grubbs first and second generation catalysts, which are dichloro(o-isopropoxyphenylmethylene)(tricyclohexylphosphine)-ruthenium(II) and 1,3-bis-(2, 4,6-trimethylphenyl)-2-imidazolidinylidene)dichloro-(o-isopropoxyphenylmethylene)ruthenium respectively. Also other catalysts containing other transition metals such as Mo can be used for this reaction.

The metathesis reactions may be conducted in a suitable solvent such as for example ethers, e.g. tetrahydrofuran (THF), dioxane; halogenated hydrocarbons, e.g. dichloromethane, CHCl₃, 1,2-dichloroethane and the like, hydrocarbons, e.g. toluene. In a preferred embodiment, the metathesis reaction is conducted in toluene. These reactions are conducted at increased temperatures under nitrogen atmosphere.

Compounds of formula (I) wherein the link between C7 and C8 in the macrocycle is a single bond, i.e. compounds of formula (I-j), can be prepared from the compounds of formula (I-i) by a reduction of the C7-C8 double bond in the compounds of formula (I-i). This reduction may be conducted by catalytic hydrogenation with hydrogen in the presence of a noble metal catalyst such as, for example, Pt, Pd, Rh, Ru or Raney nickel. Of interest is Rh on alumina. The hydrogenation reaction preferably is conducted in a solvent such as, e.g. an alcohol such as methanol, ethanol, or an ether such as THF, or mixtures thereof. Water can also be added to these solvents or solvent mixtures.

The $R^1$ group can be connected to the P1 building block at any stage of the synthesis, i.e. before or after the cyclization, or before or after the cyclization and reduction as described herein above. The compounds of formula (I) wherein $R^1$ represents —$NHSO_2R^8$, said compounds being represented by formula (I-k-1), can be prepared by linking the $R^1$ group to P1 by forming an amide bond between both moieties. Similarly, the compounds of formula (I) wherein $R^1$ represents —$OR^7$, i.e. compounds (I-k-2), can be prepared by linking the $R^1$ group to P1 by forming an ester bond. In one embodiment, the —$OR^7$ groups are introduced in the last step of the synthesis of the compounds (I) as outlined in the following reaction schemes wherein G represents a group:

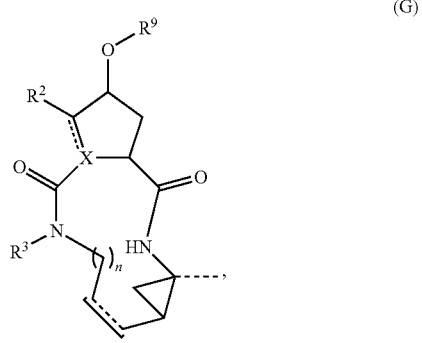

wherein the dotted line represents the bond linking group G to the remainder of the molecule.

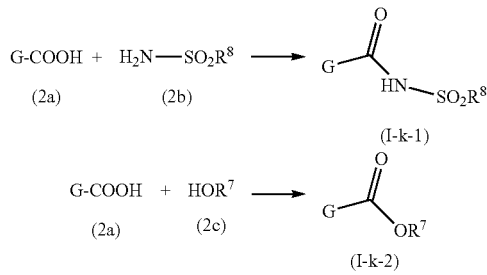

Intermediate (2a) can be coupled with the amine (2b) by an amide forming reaction such as any of the procedures for the formation of an amide bond described hereinafter. In particular, (2a) may be treated with a coupling agent, for example N,N'-carbonyl-diimidazole (CDI), N-ethyloxycarbonyl-2-ethyloxy-1,2-dihydroquinoline (EEDQ), N-isobutyloxy-carbonyl-2-isobutyloxy-1,2-dihydroquinoline (IIDQ), 1-ethyl-3-(3'-dimethylaminopropyl)carbodiimide (EDCI) or benzotriazol-1-yl-oxy-tris-pyrrolidino-phosphonium hexafluorophosphate (commercially available as PyBOP®), in a solvent such as an ether, e.g. THF, or a halogenated hydrocarbon, e.g. dichloromethane, chloroform, dichloroethane, and reacted with the desired sulfonamide (2b), preferably after reacting (2a) with the coupling agent. The reactions of (2a) with (2b) preferably are conducted in the presence of a base, for example a trialkylamine such as triethylamine or diisopropylethylamine, or 1,8-diazabicycle [5.4.0]undec-7-ene (DBU). Intermediate (2a) can also be converted into an activated form, e.g. an activated form of general formula G-CO-Z, wherein Z represents halo, or the rest of an active ester, e.g. Z is an aryloxy group such as phenoxy, p.nitrophenoxy, pentafluorophenoxy, trichlorophenoxy, pentachlorophenoxy and the like; or Z can be the rest of a mixed anhydride. In one embodiment, G-CO-Z is an acid chloride (G-CO—Cl) or a mixed acid anhydride (G-CO—O—CO—R or G-CO—O—CO—OR, R in the latter being e.g. $C_{1-4}$alkyl, such as methyl, ethyl, propyl, i.propyl, butyl, t.butyl, i.butyl, or benzyl). The activated form G-CO-Z is reacted with the sulfonamide (2b).

The activation of the carboxylic acid in (2a) as described in the above reactions may lead to an internal cyclization reaction to an azalactone intermediate of formula

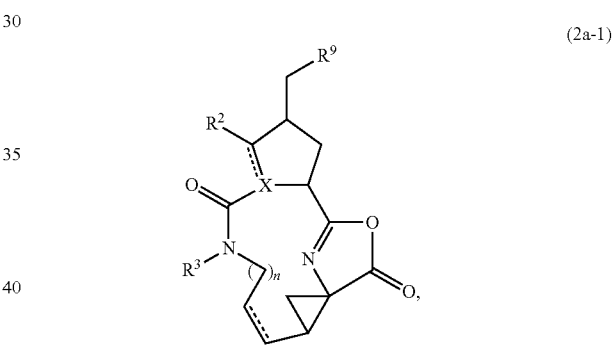

wherein X, $R^2$, $R^3$, $R^9$, n are as specified above and wherein the stereogenic centers may have the stereochemical configuration as specified above, for example as in (I-a) or (I-b). The intermediates (2a-1) can be isolated from the reaction mixture, using conventional methodology, and the isolated intermediate (2a-1) is then reacted with (2b), or the reaction mixture containing (2a-1) can be reacted further with (2b) without isolation of (2a-1). In one embodiment, where the reaction with the coupling agent is conducted in a water-immiscible solvent, the reaction mixture containing (2a-1) may be washed with water or with slightly basic water in order to remove all water-soluble side products. The thus obtained washed solution may then be reacted with (2b) without additional purification steps. The isolation of intermediates (2a-1) on the other hand may provide certain advantages in that the isolated product, after optional further purification, may be reacted with (2b), giving rise to less side products and an easier work-up of the reaction.

Intermediate (2a) can be coupled with the alcohol (2c) by an ester forming reaction. For example, (2a) and (2c) are reacted together with removal of water either physically, e.g. by azeotropical water removal, or chemically by using a dehydrating agent. Intermediate (2a) can also be converted into an activated form G-CO-Z, such as the activated forms mentioned above, and subsequently reacted with the alcohol (2c). The ester forming reactions preferably are conducted in the presence of a base such as an alkali metal carbonate or hydrogen carbonate, e.g. sodium or potassium hydrogen carbonate, or a tertiary amine such as the amines mentioned herein in relation to the amide forming reactions, in particular a trialkylamine, e.g. triethylamine. Solvents that can be used in the ester forming reactions comprise ethers such as THF; halogenated hydrocarbons such as dichoromethane, $CH_2Cl_2$; hydrocarbons such as toluene; polar aprotic solvents such as dimethylformamide (DMF), dimethyl sulfoxide (DMSO), dimethylacetamide (DMA); and the like solvents.

The compounds of formula (I) wherein $R^3$ is hydrogen, said compounds being represented by (I-1), can also be prepared by removal of a protecting group PG, from a corresponding nitrogen-protected intermediate (3a), as in the following reaction scheme. The protecting group PG in particular is any of the nitrogen protecting groups mentioned hereinafter and can be removed using procedures also mentioned hereinafter:

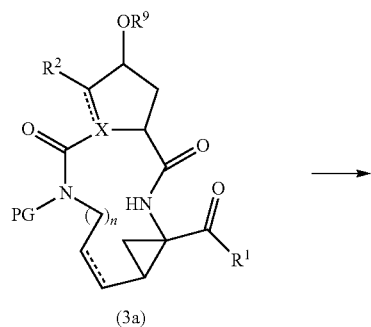

The starting materials (3a) in the above reaction can be prepared following the procedures for the preparation of compounds of formula (I), but using intermediates wherein the group $R^3$ is PG.

The compounds of formula (I) can also be prepared by reacting an intermediate (4a) with intermediate (4b) as outlined in the following reaction scheme wherein the various radicals have the meanings specified above:

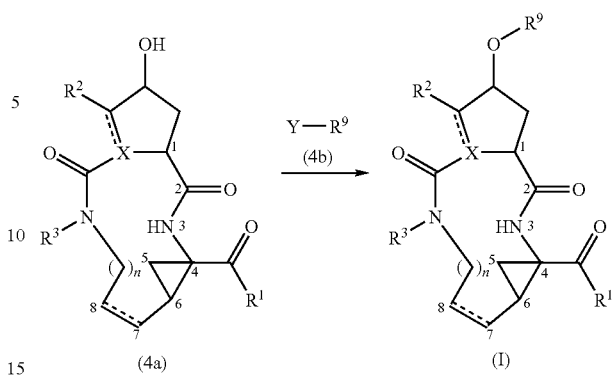

Y in (4b) represents hydroxy or a leaving group LG such as a halide, e.g. bromide or chloride, or an arylsulfonyl group, e.g. mesylate, triflate or tosylate and the like.

In one embodiment, the reaction of (4a) with (4b) is an O-arylation reaction and Y represents a leaving group. This reaction can be conducted following the procedures described by E. M. Smith et al. (J. Med. Chem. (1988), 31, 875-885). In particular, this reaction is conducted in the presence of a base, preferably a strong base, in a reaction-inert solvent, e.g. one of the solvents mentioned for the formation of an amide bond.

In a particular embodiment, starting material (4a) is reacted with (4b) in the presence of a base which is strong enough to detract a hydrogen from the hydroxy group, for example an alkali of alkaline metal hydride such as LiH or sodium hydride, or alkali metal alkoxide such as sodium or potassium methoxide or ethoxide, potassium tert-butoxide, in a reaction inert solvent like a dipolar aprotic solvent, e.g. DMA, DMF and the like. The resulting alcoholate is reacted with the arylating agent (4b), wherein Y is a suitable leaving group as mentioned above. The conversion of (4a) to (I) using this type of O-arylation reaction does not change the stereochemical configuration at the carbon bearing the hydroxy group.

Alternatively, the reaction of (4a) with (4b) can also be conducted via a Mitsunobu reaction (Mitsunobu, 1981, Synthesis, January, 1-28; Rano et al., Tetrahedron Lett., 1995, 36, 22, 3779-3792; Krchnak et al., Tetrahedron Lett., 1995, 36, 5, 6193-6196; Richter et al., Tetrahedron Lett., 1994, 35, 27, 4705-4706). This reaction comprises treatment of intermediate (4a) with (4b) wherein Y is hydroxyl, in the presence of triphenylphosphine and an activating agent such as a dialkyl azocarboxylate, e.g. diethyl azodicarboxylate (DEAD), diisopropyl azodicarboxylate (DIAD) or the like. The Mitsunobu reaction changes the stereochemical configuration at the carbon bearing the hydroxy group.

Another type of reaction useful to introduce the (4b) group onto (4a) is the Brosylate reaction whereby (4a) is reacted with p-bromobenzenesulfonyl in the presence of triethylamine or diisopropyltriethylamine and THF, followed by addition of (4b) wherein Y is hydroxyl to provide compound (I). As with the Mitsunobu reaction, the stereochemical configuration at the carbon bearing the hydroxy group is also changed.

Alternatively, in order to prepare the compounds of formula (I), first an amide bond between building blocks P2 and P1 is formed, followed by coupling of the P3 building block to the P1 moiety in P1-P2, and a subsequent carbamate or ester bond formation between P3 and the P2 moiety in P2-P1-P3 with concomitant ring closure.

Yet another alternative synthetic methodology is the formation of an amide bond between building blocks P2 and P3, followed by the coupling of building block P1 to the P3 moiety in P3-P2, and a last amide bond formation between P1 and P2 in P1-P3-P2 with concomitant ring closure.

Building blocks P1 and P3 can be linked to a P1-P3 sequence. If desired, the double bond linking P1 and P3 may be reduced. The thus formed P1-P3 sequence, either reduced or not, can be coupled to building block P2 and the thus forming sequence P1-P3-P2 subsequently cyclized by forming an amide bond.

Building blocks P1 and P3 in any of the previous approaches can be linked via double bond formation, e.g. by the olefin metathesis reaction described hereinafter, or a Wittig type reaction. If desired, the thus formed double bond can be reduced, similarly as described above for the conversion of (I-i) to (I-j). The double bond can also be reduced at a later stage, i.e. after addition of a third building block, or after formation of the macrocycle. Building blocks P2 and P1 are linked by amide bond formation and P3 and P2 are linked by carbamate or amide formation.

The tail P1' can be bonded to the P1 building block at any stage of the synthesis of the compounds of formula (I), for example before or after coupling the building blocks P2 and P1; before or after coupling the P3 building block to P1; or before or after ring closure.

The individual building blocks can first be prepared and subsequently coupled together or alternatively, precursors of the building blocks can be coupled together and modified at a later stage to the desired molecular composition. The functionalities in each of the building blocks may be protected to avoid side reactions.

The formation of amide bonds can be carried out using standard procedures such as those used for coupling amino acids in peptide synthesis. The latter involves the dehydrative coupling of a carboxyl group of one reactant with an amino group of the other reactant to form a linking amide bond. The amide bond formation may be performed by reacting the starting materials in the presence of a coupling agent or by converting the carboxyl functionality into an active form such as an active ester, mixed anhydride or a carboxyl acid chloride or bromide. General descriptions of such coupling reactions and the reagents used therein can be found in general textbooks on peptide chemistry, for example, M. Bodanszky, "Peptide Chemistry", 2nd rev. ed., Springer-Verlag, Berlin, Germany, (1993).

Examples of coupling reactions with amide bond formation include the azide method, mixed carbonic-carboxylic acid anhydride (isobutyl chloroformate) method, the carbodiimide (dicyclohexylcarbodiimide, diisopropylcarbodiimide, or water-soluble carbodiimide such as N-ethyl-N'-[(3-dimethylamino)propyl]carbodiimide) method, the active ester method (e.g. p-nitrophenyl, p-chlorophenyl, trichlorophenyl, pentachloro-phenyl, pentafluorophenyl, N-hydroxysuccinic imido and the like esters), the Woodward reagent K-method, the 1,1-carbonyldiimidazole (CDI or N,N'-carbonyl-diimidazole) method, the phosphorus reagents or oxidation-reduction methods. Some of these methods can be enhanced by adding suitable catalysts, e.g. in the carbodiimide method by adding 1-hydroxybenzotriazole, DBU, or 4-DMAP (4-dimethylamino-pyridine). Further coupling agents are (benzotriazol-1-yloxy)-tris-(dimethylamino) phosphonium hexafluorophosphate, either by itself or in the presence of 1-hydroxy-benzotriazole or 4-DMAP; or 2-(1H-benzotriazol-1-yl)-N,N,N',N'-tetra-methyluronium tetrafluoroborate, or O-(7-azabenzotriazol-1-yl)-N,N,N',N'-tetramethyluronium hexafluorophosphate. These coupling reactions can be performed in either solution (liquid phase) or solid phase.

A preferred amide bond formation is performed employing N-ethyloxycarbonyl-2-ethyl-oxy-1,2-dihydroquinoline (EEDQ) or N-isobutyloxy-carbonyl-2-isobutyloxy-1,2-dihydroquinoline (IIDQ). Unlike the classical anhydride procedure, EEDQ and IIDQ do not require base nor low reaction temperatures. Typically, the procedure involves reacting equimolar amounts of the carboxyl and amine components in an organic solvent (a wide variety of solvents can be used). Then EEDQ or IIDQ is added in excess and the mixture is allowed to stir at room temperature.

The coupling reactions preferably are conducted in an inert solvent, such as halogenated hydrocarbons, e.g. dichloromethane, chloroform, dipolar aprotic solvents such as acetonitrile, dimethylformamide, dimethylacetamide, DMSO, hexamethylphosphoric triamide (HMPT), ethers such as THF.

In many instances the coupling reactions are done in the presence of a suitable base such as a tertiary amine, e.g. triethylamine, diisopropylethylamine (DIPEA), N-methylmorpholine, N-methylpyrrolidine, 4-DMAP or DBU. The reaction temperature may range between 0° C. and 50° C. and the reaction time may range between 15 min and 24 h.

The functional groups in the building blocks that are linked together may be protected to avoid formation of undesired bonds. Appropriate protecting groups that can be used are listed for example in Greene, "Protective Groups in Organic Chemistry", John Wiley & Sons, New York (1999) and "The Peptides: Analysis, Synthesis, Biology", Vol. 3, Academic Press, New York (1987).

Carboxyl groups can be protected as an ester that can be cleaved off to give the carboxylic acid. Protecting groups that can be used include 1) alkyl esters such as methyl, trimethylsilyl and tert-butyl; 2) arylalkyl esters such as benzyl and substituted benzyl; or 3) esters that can be cleaved by a mild base or mild reductive means such as trichloroethyl and phenacyl esters.

Amino groups can be protected by a variety of N-protecting groups, such as:
1) acyl groups such as formyl, trifluoroacetyl, phthalyl, and p-toluenesulfonyl;
2) aromatic carbamate groups such as benzyloxycarbonyl (Cbz or Z) and substituted benzyloxycarbonyls, and 9-fluorenylmethyloxycarbonyl (Fmoc);
3) aliphatic carbamate groups such as tert-butyloxycarbonyl (Boc), ethoxycarbonyl, diisopropylmethoxy-carbonyl, and allyloxycarbonyl;
4) cyclic alkyl carbamate groups such as cyclopentyloxycarbonyl and adamantyloxycarbonyl;
5) alkyl groups such as triphenylmethyl, benzyl or substituted benzyl such as 4-methoxybenzyl;
6) trialkylsilyl such as trimethylsilyl or t.Bu dimethylsilyl; and
7) thiol containing groups such as phenylthiocarbonyl and dithiasuccinoyl.

Interesting amino protecting groups are Boc and Fmoc.

Preferably the amino protecting group is cleaved off prior to the next coupling step. Removal of N-protecting groups can be done following art-known procedures. When the Boc group is used, the methods of choice are trifluoroacetic acid, neat or in dichloromethane, or HCl in dioxane or in ethyl acetate. The resulting ammonium salt is then neutralized either prior to the coupling or in situ with basic solutions such as aqueous buffers, or tertiary amines in dichloromethane or acetonitrile or dimethylformamide. When the Fmoc group is used, the reagents of choice are piperidine or substituted piperidine in dimethylformamide, but any secondary amine can be used. The deprotection is carried out at a temperature between 0° C. and room temperature, usually around 15-25° C., or 20-22° C.

Other functional groups that can interfere in the coupling reactions of the building blocks may also be protected. For example hydroxyl groups may be protected as benzyl or substituted benzyl ethers, e.g. 4-methoxybenzyl ether, benzoyl or substituted benzoyl esters, e.g. 4-nitrobenzoyl ester, or with trialkylsilyl groups (e.g. trimethylsilyl or tert-butyldimethylsilyl).

Further amino groups may be protected by protecting groups that can be cleaved off selectively. For example, when Boc is used as the α-amino protecting group, the following side chain protecting groups are suitable: p-toluenesulfonyl (tosyl) moieties can be used to protect further amino groups; benzyl (Bn) ethers can be used to protect hydroxy groups; and benzyl esters can be used to protect further carboxyl groups. Or when Fmoc is chosen for the α-amino protection, usually tert-butyl based protecting groups are acceptable. For instance, Boc can be used for further amino groups; tert-butyl ethers for hydroxyl groups; and tert-butyl esters for further carboxyl groups.

Any of the protecting groups may be removed at any stage of the synthesis procedure but preferably, the protecting groups of any of the functionalities not involved in the reaction steps are removed after completion of the build-up of the macrocycle. Removal of the protecting groups can be done in whatever manner is dictated by the choice of protecting groups, which manners are well known to those skilled in the art.

The intermediates of formula (1a) wherein X is N, said intermediates being represented by formula (1a-1), may be prepared starting from intermediates (5a) which are reacted with an alkenamine (5b) in the presence of a carbonyl introducing agent as outlined in the following reaction scheme.

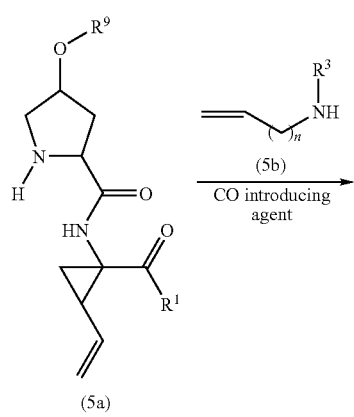

(5a)

-continued

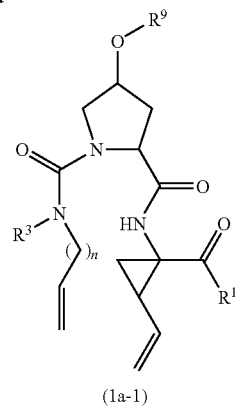

(1a-1)

Carbonyl (CO) introducing agents include phosgene, or phosgene derivatives such as CDI, and the like. In one embodiment (5a) is reacted with the CO introducing agent in the presence of a suitable base and a solvent, which can be the bases and solvents used in the amide forming reactions as described above. In a particular embodiment, the base is a hydrogencarbonate, e.g. $NaHCO_3$, or a tertiary amine such as triethylamine and the like, and the solvent is an ether or halogenated hydrocarbon, e.g. THF, $CH_2Cl_2$, $CHCl_3$, and the like. Thereafter, the amine (5b) is added thereby obtaining intermediates (1a-1) as in the above scheme. An alternative route using similar reaction conditions involves first reacting the CO introducing agent with the alkenamine (5b) and then reacting the thus formed intermediate with (5a).

The intermediates (1a-1) can alternatively be prepared as follows:

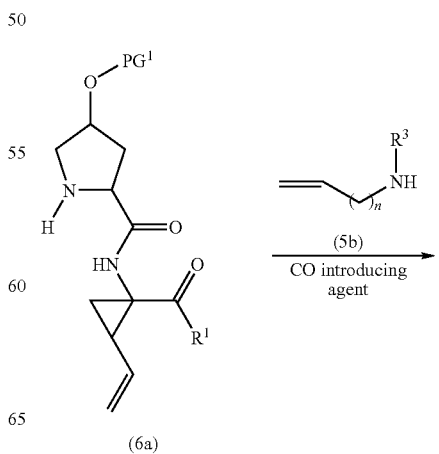

(6a)

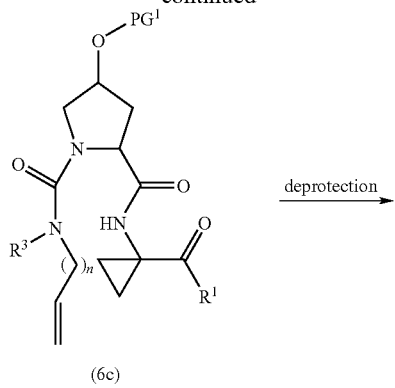

(6c)

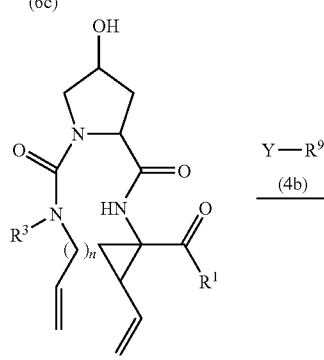

(6d)

PG¹ is an O-protecting group, which can be any of the groups mentioned herein and in particular is a benzoyl or substituted benzoyl group such as 4-nitrobenzoyl. In the latter instance this group can be removed by reaction with a an alkali metal hydroxide (LiOH, NaOH, KOH), in particular where PG¹ is 4-nitro-benzoyl, with LiOH, in an aqueous medium comprising water and a water-soluble organic solvent such as an aliphatic alcohol (methanol, ethanol) and THF.

Intermediates (6a) are reacted with (5b) in the presence of a carbonyl introducing agent, similar as described above, and this reaction yields intermediates (6c). These are deprotected, in particular using the reaction conditions mentioned above. The resulting alcohol (6d) is reacted with intermediates (4b) as described above for the reaction of (4a) with (4b) and this reaction results in intermediates (1a-1).

The intermediates of formula (1a) wherein X is C, said intermediates being represented by formula (1a-2), may be prepared by an amide forming reaction starting from intermediates (7a) which are reacted with an amine (5b) as shown in the following reaction scheme, using reaction conditions for preparing amides such as those described above.

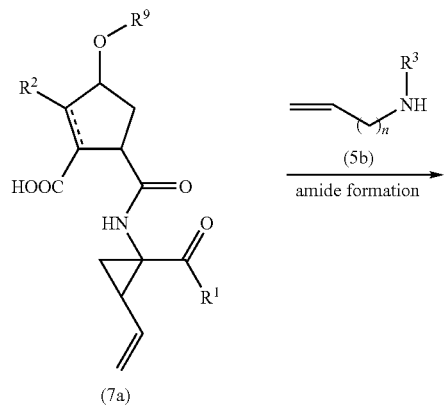

(7a)

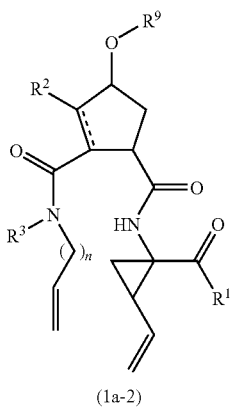

(1a-2)

The intermediates (1a-1) can alternatively be prepared as follows:

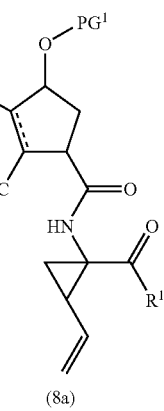

(8a)

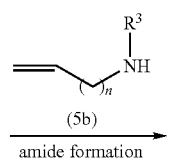

(5b)

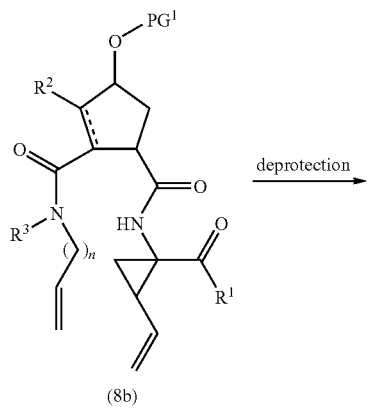

(8b)

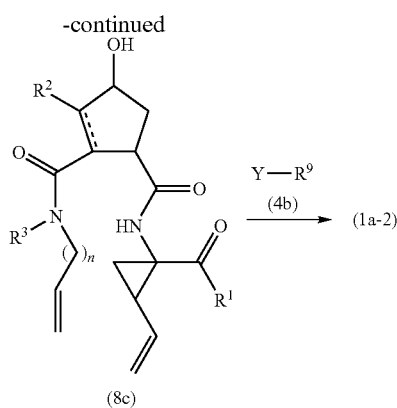

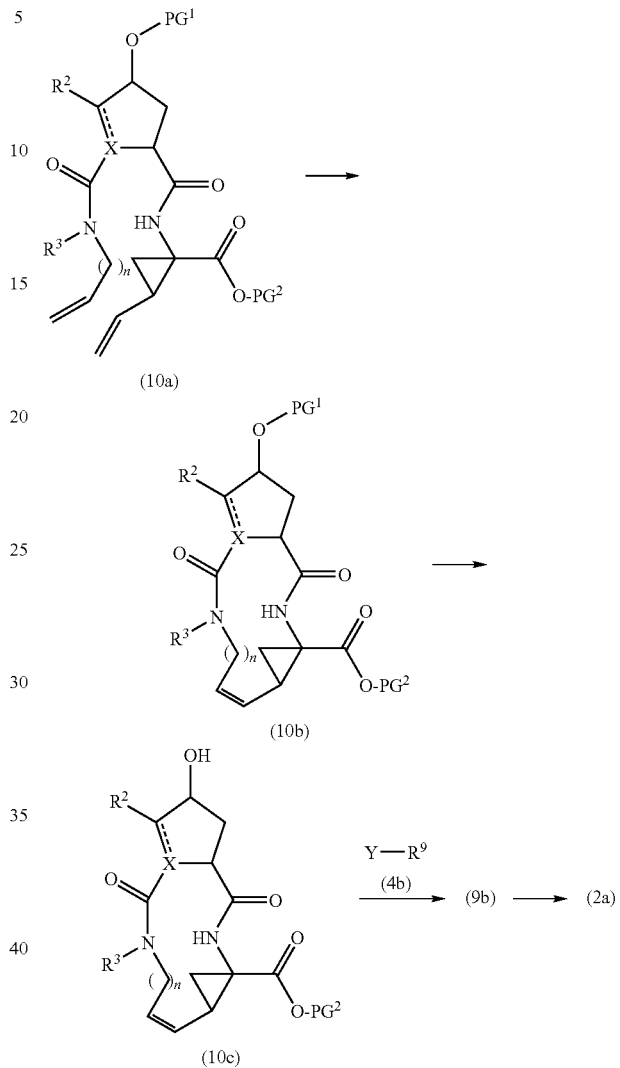

PG$^1$ is an O-protecting group as described above. The same reaction conditions as described above may be used: amide formation as described above, removal of PG$^1$ as in the description of the protecting groups and introduction of R$^9$ as in the reactions of (4a) with the reagents (4b).

The intermediates of formula (2a) may be prepared by first cyclizing the open amide (9a) to a macrocyclic ester (9b), which in turn is converted to (2a) as follows:

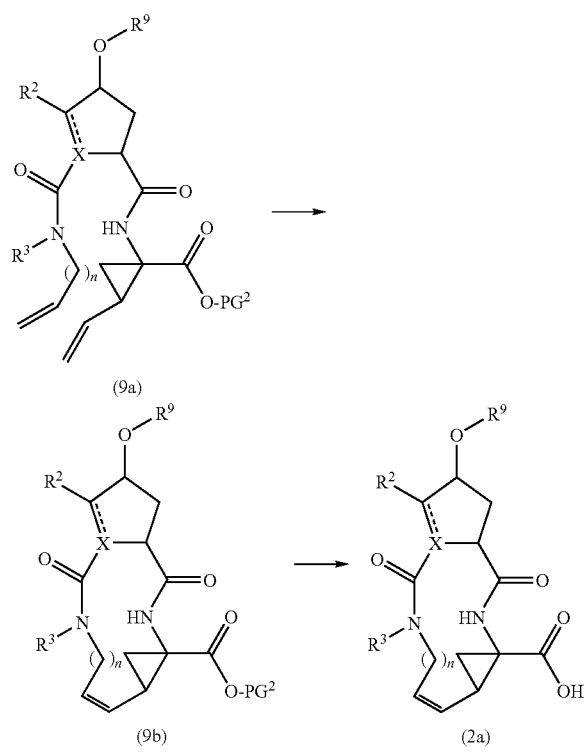

PG$^2$ is a carboxyl protecting group, e.g. one of the carboxyl protecting groups mentioned above, in particular a C$_{1-4}$alkyl or benzyl, e.g. a methyl, ethyl or t.butyl. The reaction of (9a) to (9b) is a metathesis reaction and is conducted as described above. The group PG$^2$ is removed following procedures also described above. Where PG$^2$ is a C$_{1-4}$alkyl, it is removed by alkaline hydrolysis, e.g. with NaOH or preferably LiOH, in an aqueous solvent, e.g. an aliphatic alcohol/water mixture. A benzyl group can be removed by trimethylsilyl bromide (TMSBr).

In an alternative synthesis, intermediates (2a) can be prepared as follows:

The PG$^1$ group is selected such that it is selectively cleavable towards PG$^2$. PG$^2$ may be e.g. methyl or ethyl esters, which can be removed by treatment with an alkali metal hydroxide in an aqueous medium, in which case PG$^1$ e.g. is benzyl. PG$^2$ may be t.butyl removable under acidic conditions, or PG$^1$ may be benzoyl removable by treatment with sodium hydroxide or lithium hydroxide, or PG$^1$ may be an optionally substituted benzyl group (e.g. p-methoxybenzyl) removable by dichlorodicyanoquinone (DDQ) or TMSBr. PG$^1$ may also be an ethoxymethyl, which can be introduced with chloromethylethylether in the presence of DIPEA and dichloromethane (DCM), and can be cleaved with hydrochloric acid in the presence of THF/methanol/water.

First, intermediates (10a) are cyclized to the macrocyclic esters (10b), the latter are deprotected by removal of the PG$^1$ group to (10c), which are reacted with intermediates (4b), followed by removal of carboxyl protecting group PG$^2$. The cyclization, deprotection of PG$^1$ and PG$^2$ and the coupling with (4b) are as described above.

The R$^1$ groups can be introduced at any stage of the synthesis, either as the last step as described above, or earlier, before the macrocycle formation. In the following scheme, the groups $R^1$ being —NH—SO$_2$R$^8$ or —OR$^7$ (which are as specified above) are introduced:

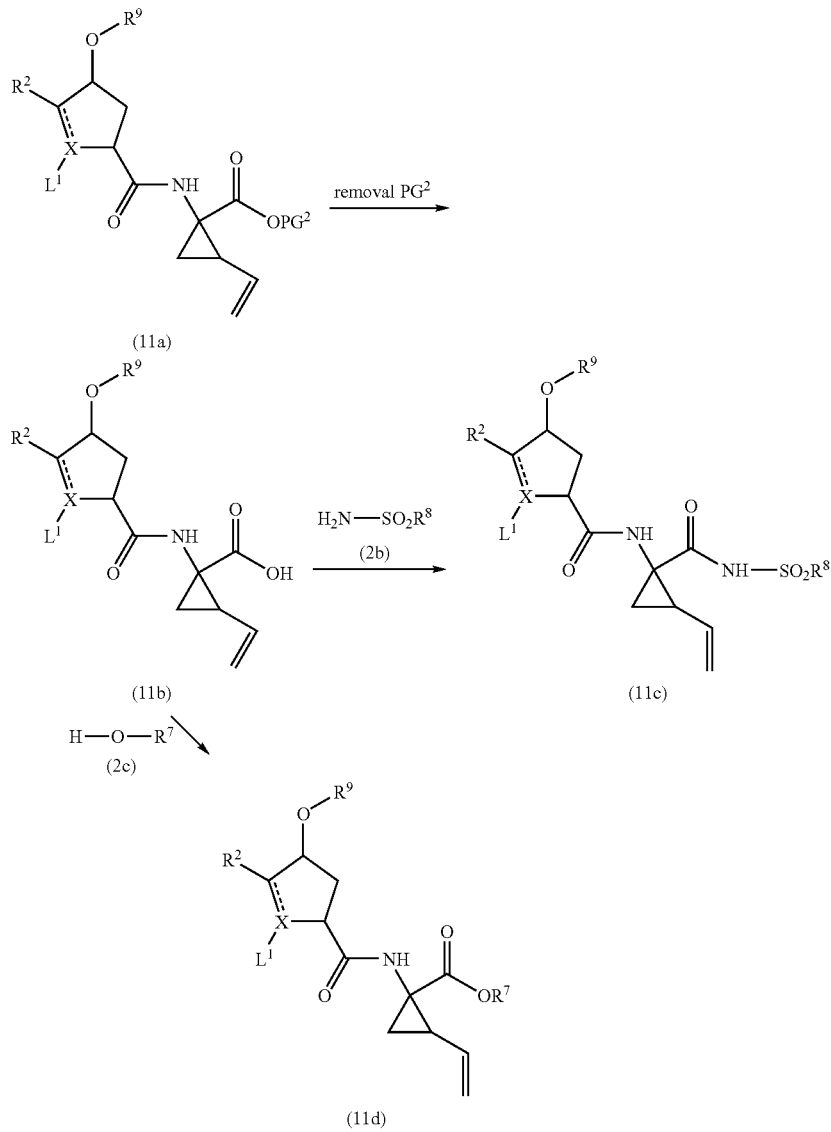

In the above scheme, PG$^2$ is as defined above and L$^1$ is a P3 group

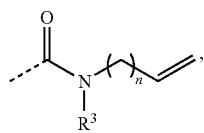

(b)

wherein n and R$^3$ are as defined above and where X is N, L$^1$ may also be a nitrogen-protecting group (PG, as defined above) and where X is C, L$^1$ may also be a group —COOPG$^{2a}$, wherein the group PG$^{2a}$ is a carboxyl protecting group similar as PG$^2$, but wherein PG$^{2a}$ is selectively cleavable towards PG$^2$. In one embodiment PG$^{2a}$ is t.butyl and PG$^2$ is methyl or ethyl.

The intermediates (11c) and (11d) wherein L$^1$ represents a group (b) correspond to the intermediates (1a) and may be processed further as specified above.

Coupling of P1 and P2 Building Blocks

The P1 and P2 building blocks are linked using an amide forming reaction following the procedures described above. The P1 building block may have a carboxyl protecting group PG$^2$ (as in (12b)) or may already be linked to P1' group (as in (12c)). L$^2$ is a N-protecting group (PG), or a group (b), as specified above. L$^3$ is hydroxy, —OPG$^1$ or a group —O—R$^9$ as specified above. Where in any of the following reaction schemes L$^3$ is hydroxy, prior to each reaction step, it may be protected as a group —OPG$^1$ and, if desired, subsequently deprotected back to a free hydroxy function. Similarly as described above, the hydroxy function may be converted to a group —O—R$^9$.

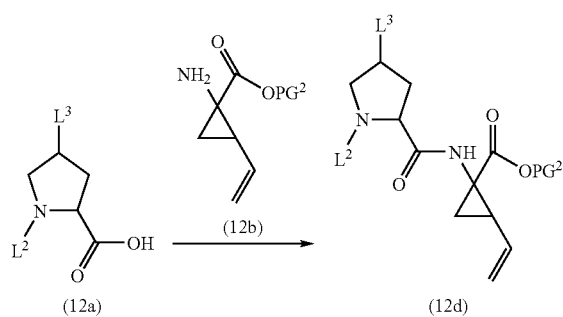
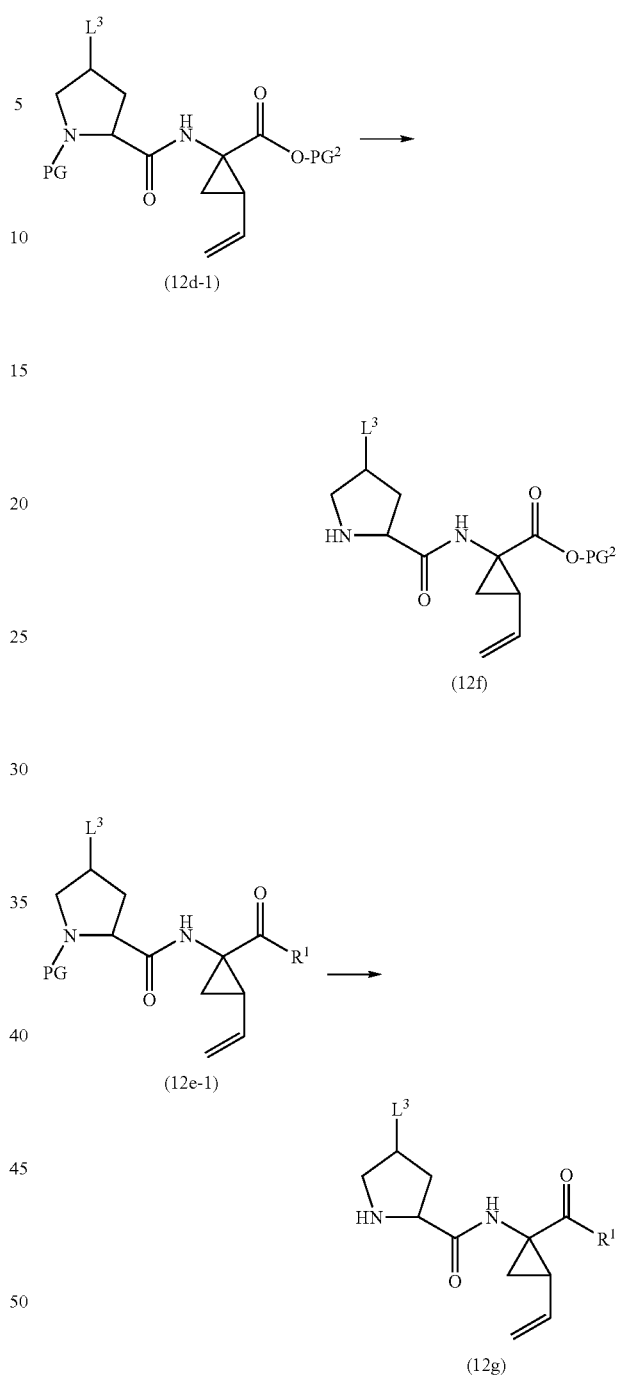

In the procedure of the above scheme, a cyclopropyl amino acid (12b) or (12c) is coupled to the acid function of the P2 building block (12a) with the formation of an amide linkage, following the procedures described above. Intermediates (12d) or (12e) are obtained. Where in the latter $L^2$ is a group (b), the resulting products are P3-P2-P1 sequences encompassing some of the intermediates (11c) or (11d) in the previous reaction scheme. Removal of the acid protecting group in (12d), using the appropriate conditions for the protecting group used, followed by coupling with an amine $H_2N-SO_2R^8$ (2b) or with $HOR^7$ (2c) as described above, again yields the intermediates (12e), wherein $-COR^1$ are amide or ester groups. Where $L^2$ is a N-protecting group, it can be removed yielding intermediates (5a) or (6a). In one embodiment, PG in this reaction is a BOC group and $PG^2$ is methyl or ethyl. Where additionally $L^3$ is hydroxy, the starting material (12a) is Boc-L-hydroxyproline. In a particular embodiment, PG is BOC, $PG^2$ is methyl or ethyl and $L^3$ is $-O-R^9$.

In one embodiment, $L^2$ is a group (b) and these reactions involve coupling P1 to P2-P3, which results in the intermediates (1a-1) or (1a) mentioned above. In another embodiment, $L^2$ is a N-protecting group PG, which is as specified above, and the coupling reaction results in intermediates (12d-1) or (12e-1), from which the group PG can be removed, using reaction conditions mentioned above, obtaining intermediates (12f) or (12g) respectively, which encompass intermediates (5a) and (6a) as specified above:

In one embodiment, the group $L^3$ in the above schemes represents a group $-O-PG^1$ which can be introduced on a starting material (12a) wherein $L^3$ is hydroxy. In this instance $PG^1$ is chosen such that it is selectively cleavable towards group $L^2$ being PG.

In a similar way, P2 building blocks wherein X is C, which are cyclopentane or cyclopentene derivatives, can be linked to P1 building blocks as outlined in the following scheme wherein $R^1$, $R^2$, and $L^3$ are as specified above and $PG^2$ and $PG^{2a}$ are carboxyl protecting groups. $PG^{2a}$ typically is chosen such that it is selectively cleavable towards group $PG^2$. Removal of the $PG^{2a}$ group in (13c) yields intermediates (7a) or (8a), which can be reacted with (5b) as described above.

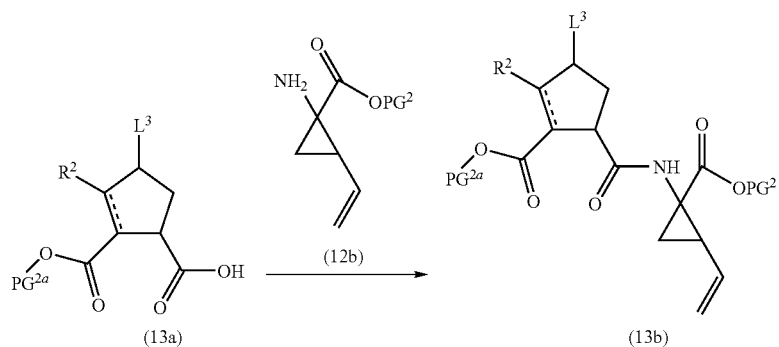

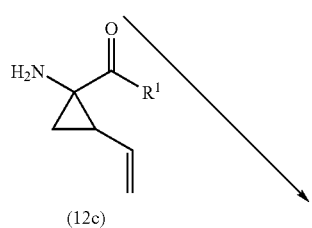

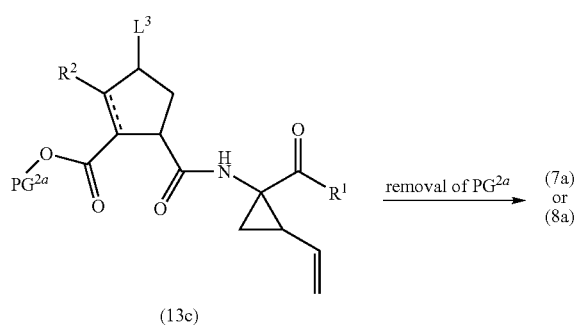

In a particular embodiment, where X is CH, $R^2$ is H, and where X and the carbon bearing $R^2$ are linked by a single bond (P2 being a cyclopentane moiety), $PG^{2a}$ and $L^3$ taken together form a bond and the P2 building block is represented by formula:

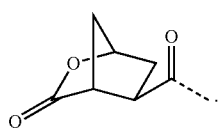

(c)

Bicyclic acid (14a) is reacted with (12b) or (12c) similar as described above to (14b) and (14c) respectively, wherein the lactone is opened giving intermediates (14c) and (14e). The lactones can be opened using ester hydrolysis procedures, for example using the reaction conditions described above for the alkaline removal of a $PG^1$ group in (9b), in particular using basic conditions such as an alkali metal hydroxide, e.g. NaOH, KOH, in particular LiOH.

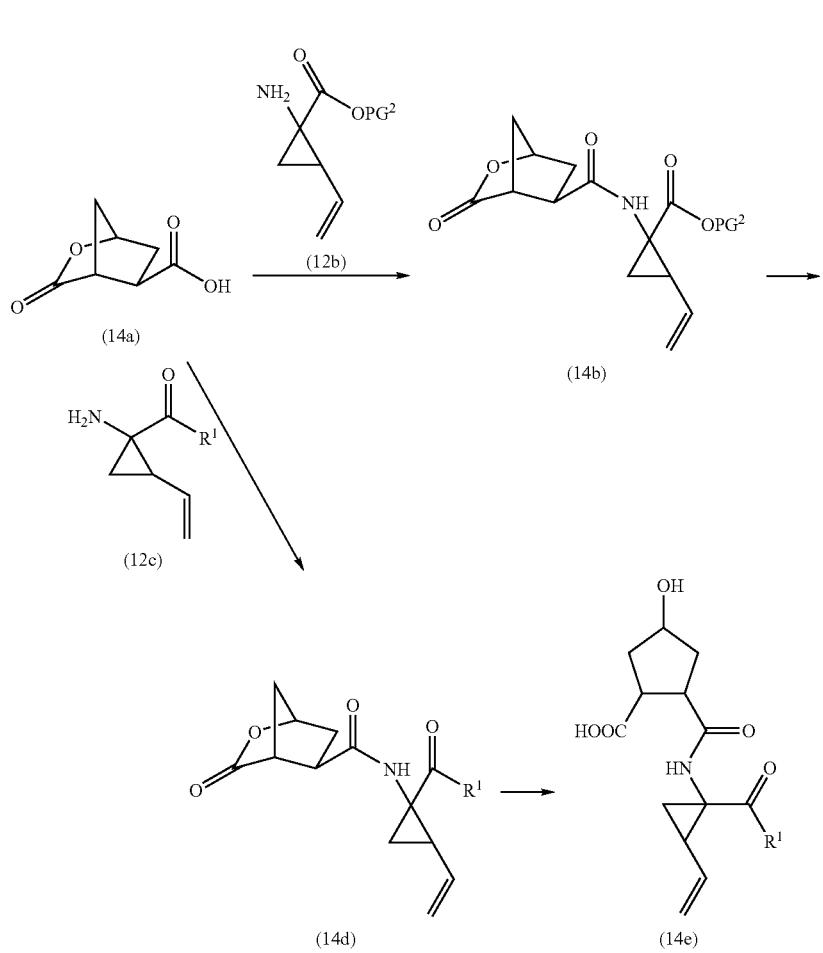

Intermediates (14c) and (14e) can be processed further as described hereinafter.

Coupling of P3 and P2 Building Blocks

For P2 building blocks that have a pyrrolidine moiety, the P3 and P2 or P3 and P2-P1 building blocks are linked using a carbamate forming reaction following the procedures described above for the coupling of (5a) with (5b). A general procedure for coupling P2 blocks having a pyrrolidine moiety is represented in the following reaction scheme wherein $L^3$ is as specified above and $L^4$ is a group —$OPG^2$, a group (d)

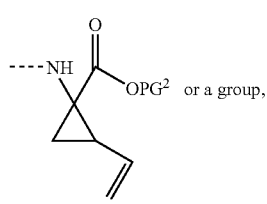

OPG² or a group, (e)

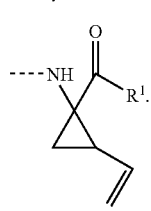

-continued

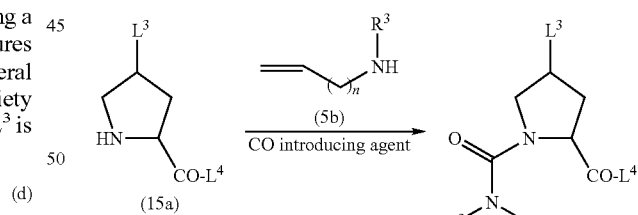

In one embodiment $L^4$ in (15a) is a group —$OPG^2$, the $PG^2$ group may be removed and the resulting acid coupled with cyclopropyl amino acids (12b) or (12c), yielding intermediates (12d) or (12e) wherein $L^2$ is a radical (d) or (e).

A general procedure for coupling P3 blocks with a P2 block or a with a P2-P1 block wherein the P2 is a cyclopentane or cyclopentene is shown in the following scheme. $L^3$ and $L^4$ are as specified above.

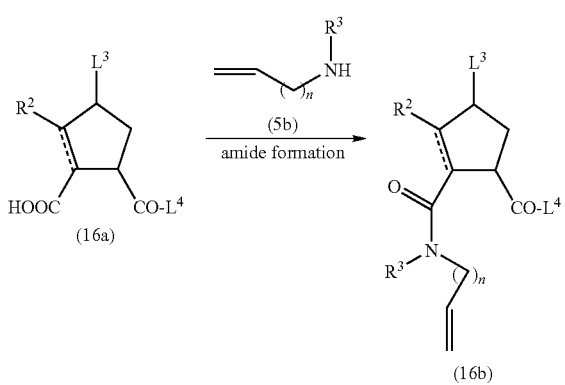

In a particular embodiment $L^3$ and $L^4$ taken together may form a lactone bridge as in (14a), and the coupling of a P3 block with a P2 block is as follows:

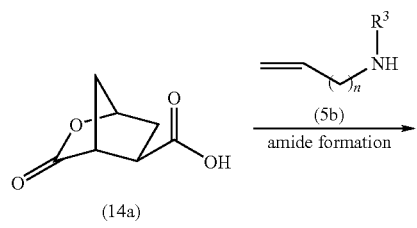

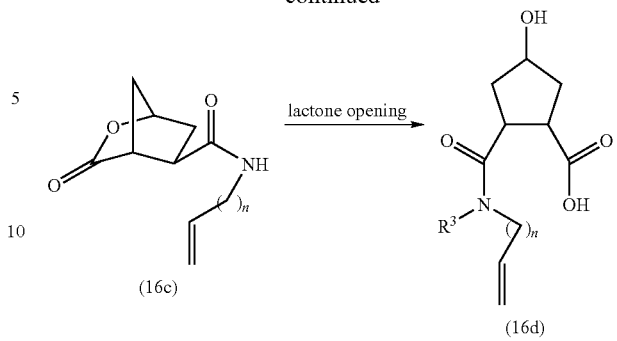

Bicyclic lactone (14a) is reacted with (5b) in an amide forming reaction to amide (16c) in which the lactone bridge is opened to (16d). The reaction conditions for the amide forming and lactone opening reactions are as described above or hereinafter. Intermediate (16d) in turn can be coupled to a P1 group as described above.

The reactions in the above schemes are conducted using the same procedures as described above for the reactions of (5a), (6a), (7a) or (8a) with (5b) and in particular the above reactions wherein $L^4$ is a group (d) or (e) correspond to the reactions of (5a), (6a), (7a) or (8a) with (5b), as described above.

The building blocks P1, P1', P2 and P3 used in the preparation of the compounds of formula (I) can be prepared starting from art-known intermediates. A number of such syntheses are described hereafter in more detail.

The individual building blocks can first be prepared and subsequently coupled together or alternatively, precursors of the building blocks can be coupled together and modified at a later stage to the desired molecular composition.

The functionalities in each of the building blocks may be protected to avoid side reactions.

Synthesis of P2 Building Blocks

The P2 building blocks contain either a pyrrolidine, a cyclopentane, or a cyclopentene moiety substituted with a group —O—$R^9$.

P2 building blocks containing a pyrrolidine moiety can be derived from commercially available hydroxy proline.

The preparation of P2 building blocks that contain a cylopentane ring may be performed as shown in the scheme below.

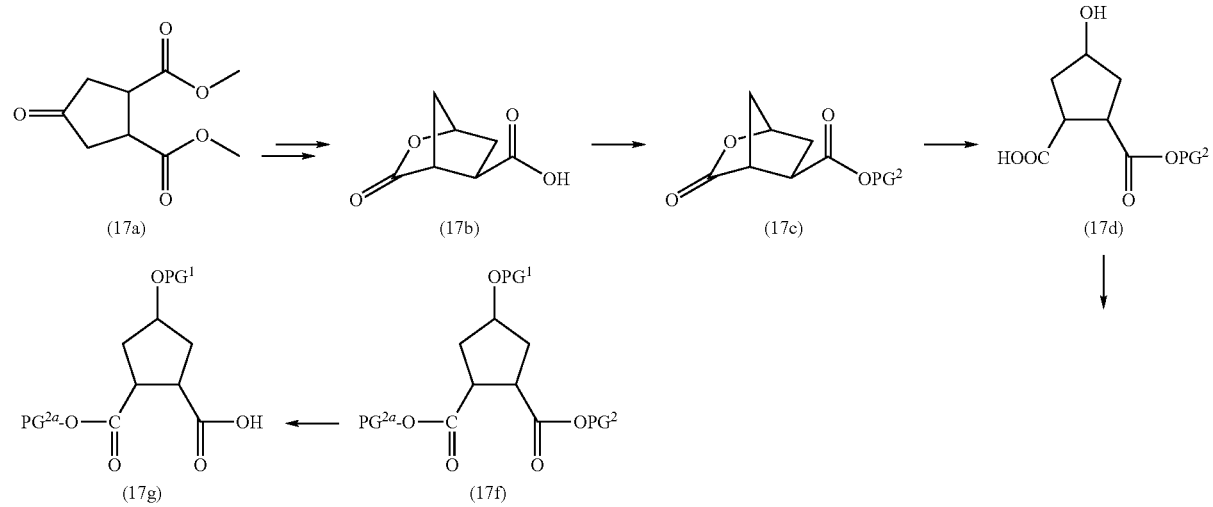

-continued

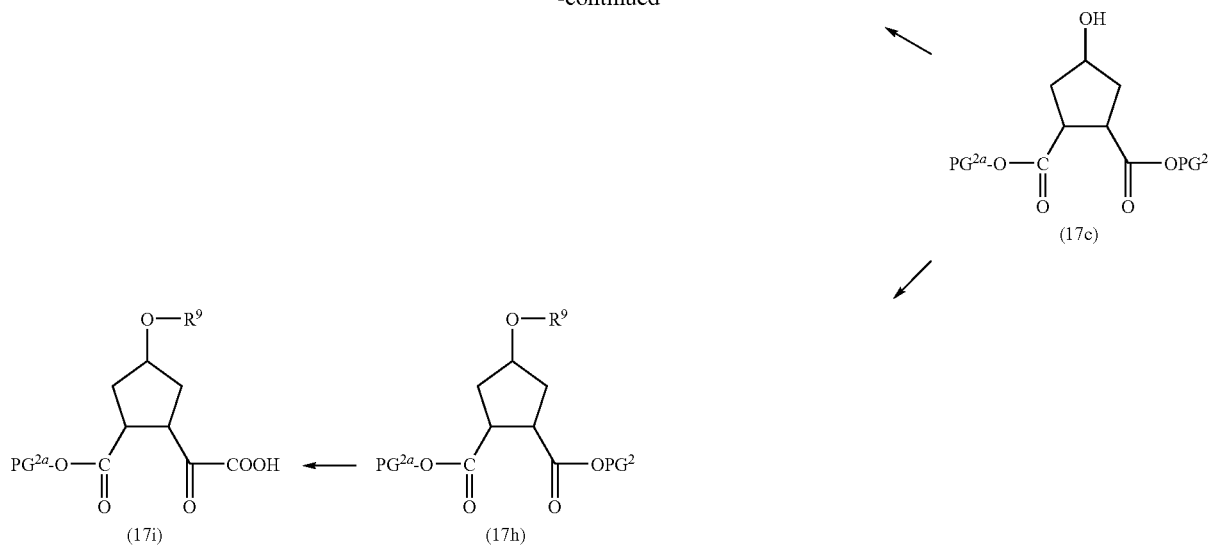

The bicyclic acid (17b) can be prepared, for example, from 3,4-bis(methoxy-carbonyl)-cyclopentanone (17a), as described by Rosenquist et al. in Acta Chem. Scand. 46 (1992) 1127-1129. A first step in this procedure involves the reduction of the keto group with a reducing agent like sodium borohydride in a solvent such as methanol, followed by hydrolysis of the esters and finally ring closure to the bicyclic lactone (17b) using lactone forming procedures, in particular by using acetic anhydride in the presence of a weak base such as pyridine. The carboxylic acid functionality in (17b) can then be protected by introducing an appropriate carboxyl protecting group, such as a group $PG^2$, which is as specified above, thus providing bicyclic ester (17c). The group $PG^2$ in particular is acid-labile such as a t.butyl group and is introduced, e.g. by treatment with isobutene in the presence of an acid or a Lewis acid. Lactone opening of (17c) using reaction conditions described above, in particular with lithium hydroxide, yields the acid (17d), which can be used further in coupling reactions with P1 building blocks. The free acid in (17d) may also be protected, preferably with an acid protecting group $PG^{2a}$ that is selectively cleavable towards $PG^2$, and the hydroxy function may be converted to a group $—OPG^1$ or to a group $—O—R^9$. The products obtained upon removal of the group $PG^2$ are intermediates (17g) and (17i), which correspond to intermediates (13a) or (16a) specified above.

Intermediates with specific stereochemistry may be prepared by resolving the intermediates in the above reaction sequence. For example, (17b) may be resolved following art-known procedures, e.g. by salt form action with an optically active base or by chiral chromatography, and the resulting stereoisomers may be processed further as described above. The OH and COOH groups in (17d) are in cis position. Trans analogs can be prepared by inverting the stereochemistry at the carbon bearing the OH function by using specific reagents in the reactions introducing $OPG^1$ or $O—R^9$ that invert the stereochemistry, such as, e.g. by applying a Mitsunobu reaction.

In one embodiment, the intermediates (17d) are coupled to P1 blocks (12b) or (12c), which coupling reactions correspond to the coupling of (13a) or (16a) with the same P1 blocks, using the same conditions. Subsequent introduction of an $—O—R^9$ substituent as described above followed by removal of the acid protection group $PG^2$ yields intermediates (8a-1), which are a subclass of the intermediates (7a), or part of the intermediates (16a). The reaction products of the $PG^2$ removal can be further coupled to a P3 building block. In one embodiment $PG^2$ in (17d) is t.butyl which can be removed under acidic conditions, e.g. with trifluoroacetic acid.

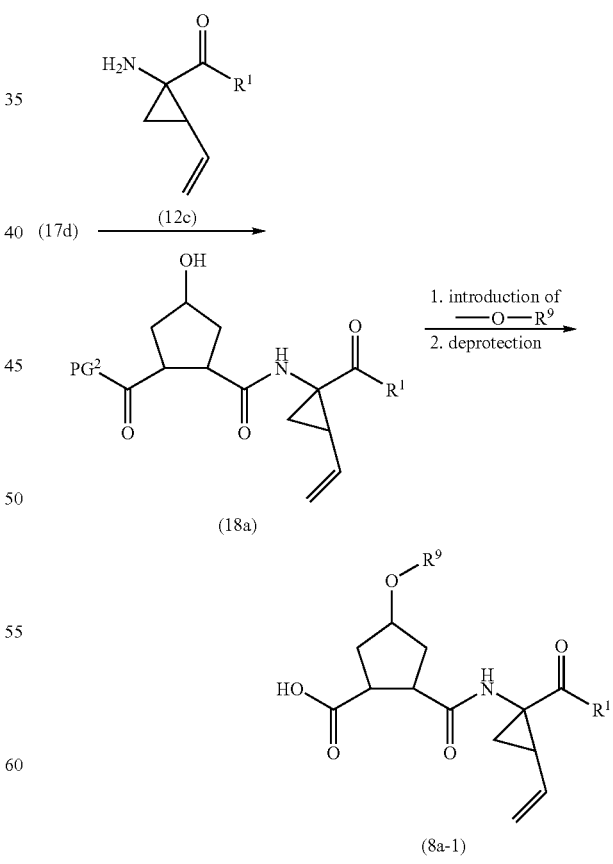

An unsaturated P2 building block, i.e. a cyclopentene ring, may be prepared as illustrated in the scheme below.

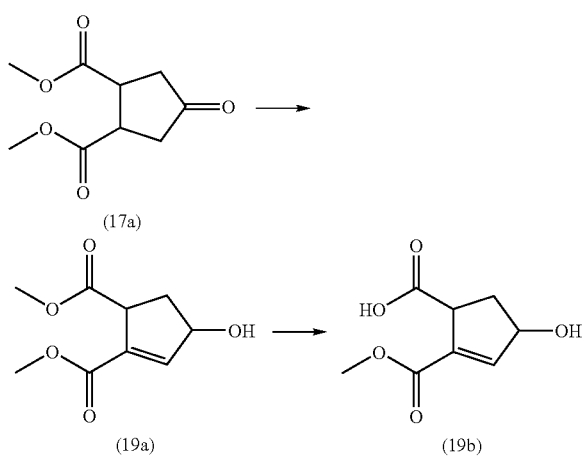

A bromination-elimination reaction of 3,4-bis(methoxycarbonyl)cyclopentanone (17a) as described by Dolby et al. in J. Org. Chem. 36 (1971) 1277-1285 followed by reduction of the keto functionality with a reducing agent like sodium borohydride provides the cyclopentenol (19a). Selective ester hydrolysis using for example lithium hydroxide in a solvent like a mixture of dioxane and water provides the hydroxy substituted monoester cyclopentenol (19b).

An unsaturated P2 building block wherein $R^2$ can be other than hydrogen, may be prepared as shown in the scheme below.

ment with di-tert-butyl dicarbonate in the presence of a base like dimethylaminopyridine. Intermediate (20e) is treated with a base such as lithium diisopropyl amide in a solvent like THF, and reacted with (20c) to give the alkenyl diester (20f). Cyclisation of (20f) by an olefin metathesis reaction, performed as described above, provides cyclopentene derivative (20g). Stereoselective epoxidation of (20g) can be carried out using the Jacobsen asymmetric epoxidation method to obtain epoxide (20h). Finally, an epoxide opening reaction under basic conditions, e.g. by addition of a base, in particular DBN (1,5-diazabicyclo-[4.3.0]non-5-ene), yields the alcohol (20i). Optionally, the double bond in intermediate (20i) can be reduced, for example by catalytic hydrogenation using a catalyst like palladium on carbon, yielding the corresponding cyclopentane compound. The t.butyl ester may be removed to produce the corresponding acid, which subsequently is coupled to a P1 building block.

The —$R^9$ group can be introduced on the pyrrolidine, cyclopentane or cyclopentene rings at any convenient stage of the synthesis of the compounds according to the present invention. One approach is to first introduce the —$R^9$ group to the said rings and subsequently add the other desired building blocks, i.e. P1 (optionally with the P1' tail) and P3, followed by the macrocycle formation. Another approach is to couple the building blocks P2, bearing no —O—$R^9$ substituent, with each P1 and P3, and to add the —$R^9$ group either before or after the macrocycle formation. In the latter procedure, the P2 moieties have a hydroxy group, which may be protected by a hydroxy protecting group $PG^1$.

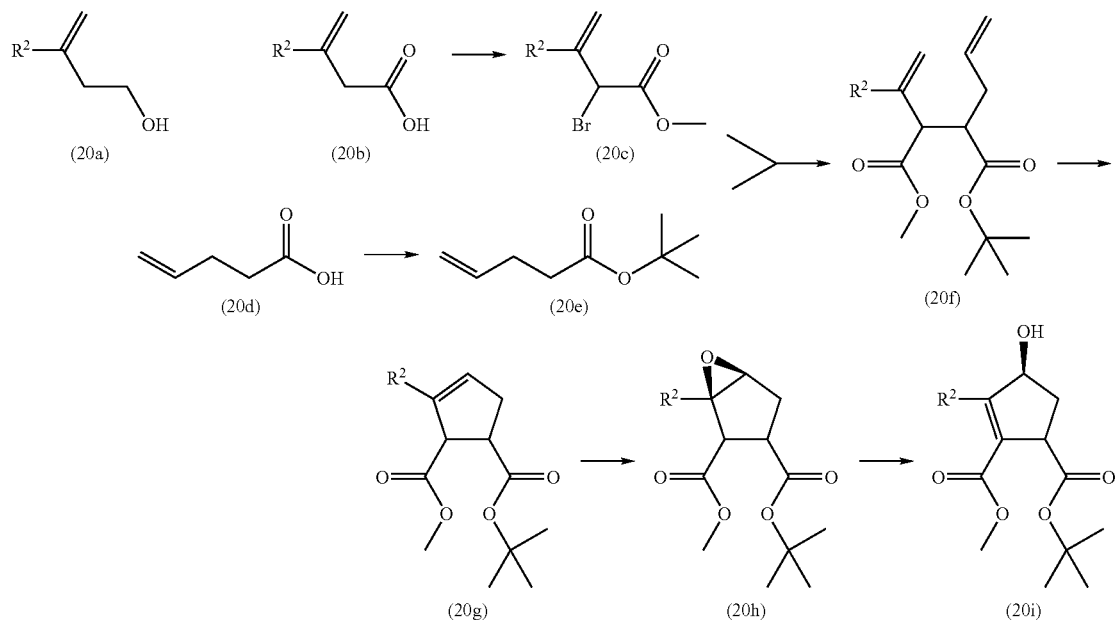

Oxidation of commercially available 3-methyl-3-buten-1-ol (20a), in particular by an oxidizing agent like pyridinium chlorochromate, yields (20b), which is converted to the corresponding methyl ester, e.g. by treatment with acetyl chloride in methanol, followed by a bromination reaction with bromine yielding the α-bromo ester (20c). The latter can then be condensed with the alkenyl ester (20e), obtained from (20d) by an ester forming reaction. The ester in (20e) preferably is a t.butyl ester which can be prepared from the corresponding commercially available acid (20d), e.g. by treat- $R^9$ groups can be introduced on building blocks P2 by reacting hydroxy substituted intermediates (21a) with intermediates (4b) similar as described above for the synthesis of (I) starting from (4a). These reactions are represented in the schemes below, wherein $L^2$ is as specified above and $L^5$ and $L^{5a}$ independently from one another, represent hydroxy, a carboxyl protecting group —$OPG^2$ or —$OPG^{2a}$, or $L^5$ may also represent a P1 group such as a group (d) or (e) as specified above, or $L^{5a}$ may also represent a P3 group such as a group (b) as specified above. The groups $PG^2$ and $PG^{2a}$ are as specified above. Where the groups $L^5$ and $L^{5a}$ are $PG^2$ or $PG^{2a}$, they are chosen such that each group is selectively cleavable towards the other. For example, one of $L^5$ and $L^{5a}$ may be a methyl or ethyl group and the other a benzyl or t.butyl group.

In one embodiment in (21a), $L^2$ is PG and $L^5$ is —$OPG^2$, or in (21d), $L^{5a}$ is —$OPG^2$ and $L^5$ is —$OPG^2$ and the $PG^2$ groups are removed as described above.

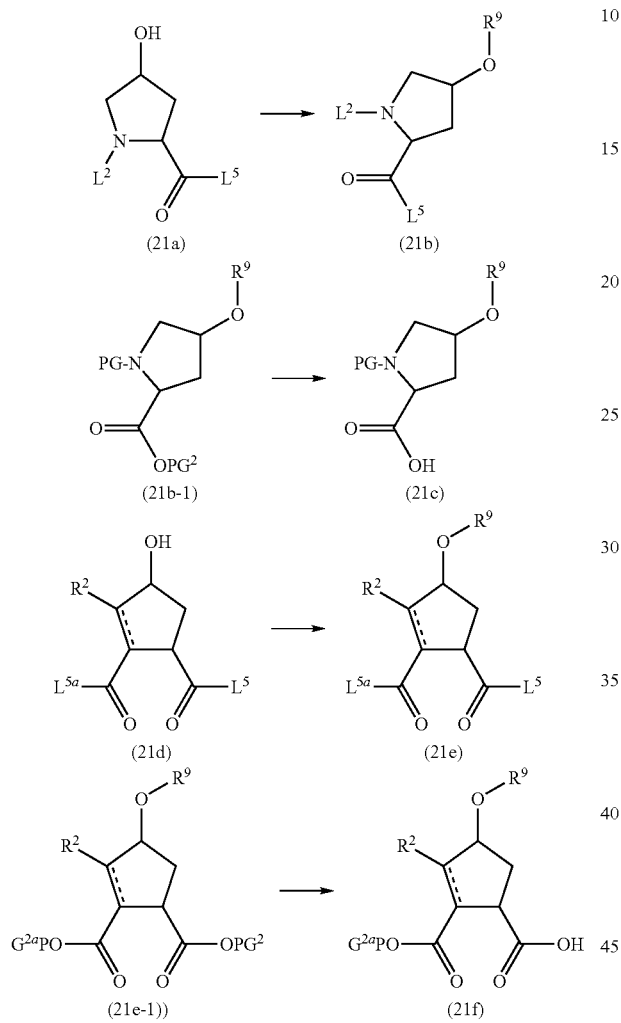

Alternatively, when handling hydroxy substituted cyclopentane analogues, the quinoline substituent can be introduced via a similar Mitsunobu reaction by reacting the hydroxy group of compound (2a') with the desired alcohol (3b) in the presence of triphenylphosphine and an activating agent like DEAD, DIAD or the like.

In another embodiment the group $L^2$ is BOC, $L^5$ is hydroxy and the starting material (21a) is commercially available BOC-hydroxyproline, or any other stereoisomeric form thereof, e.g. BOC-L-hydroxyproline, in particular the trans isomer of the latter. Where $L^5$ in (21b) is a carboxyl-protecting group, it may be removed following procedures described above to (21c). In still another embodiment PG in (21b-1) is Boc and $PG^2$ is a lower alkyl ester, in particular a methyl or ethyl ester. Hydrolysis of the latter ester to the acid can be done by standard procedures, e.g. acid hydrolysis with hydrochloric acid in methanol or with an alkali metal hydroxide such as NaOH, in particular with LiOH. In another embodiment, hydroxy substituted cyclopentane or cyclopentene analogs (21d) are converted to (21e), which, where $L^5$ and $L^{5a}$ are —$OPG^2$ or —$OPG^{2a}$, may be converted to the corresponding acids (21f) by removal of the group $PG^2$. Removal of $PG^{2a}$ in (21e-1) leads to similar intermediates.

The intermediates Y—$R^9$ (4b) can be prepared following art-known methods using known starting materials. A number of synthesis pathways for such intermediates will be described hereafter in somewhat more detail. For example the preparation of the above mentioned intermediate quinolines is shown below in the following scheme.

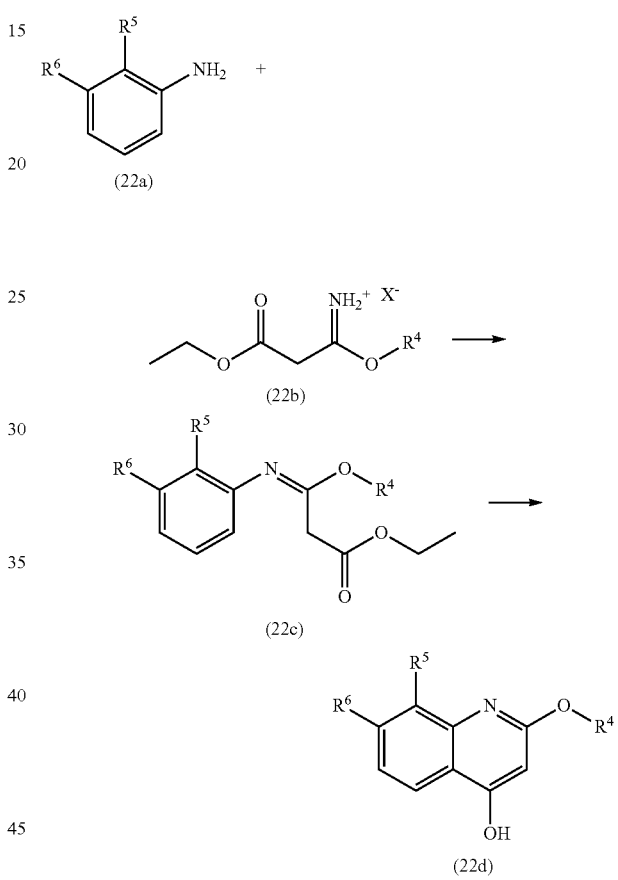

Condensation of an aniline (22a) with an iminoether (22b) produces compound (22c). Such condensation is preferably carried out in a solvent that solubilizes the iminoether, e.g. ethanol or methanol. Formation of the quinoline (22d) is achieved by an electrophilic aromatic cyclisation of compound (22c). This electrophilic aromatic cyclisation typically is carried out at increased temperature, in particular at temperatures around or higher than 200° C., in a solvent that can boil at 200° C. or more, e.g. in diphenylether.

Synthesis of P1 Building Blocks

The cyclopropane amino acid used in the preparation of the P1 fragment is commercially available or can be prepared using art-known procedures.

In particular the aminovinyl-cyclopropyl ethyl ester (12b) may be obtained according to the procedure described in WO 00/09543 or as illustrated in the following scheme, wherein $PG^2$ is a carboxyl protecting group as specified above:

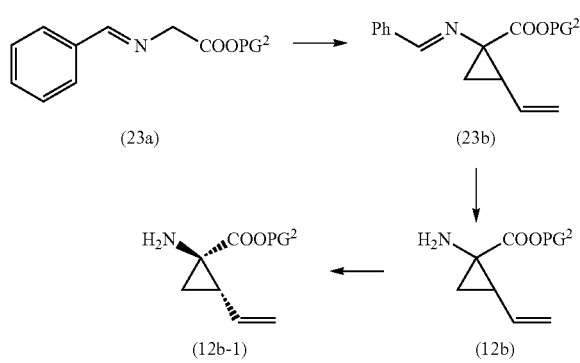

Treatment of commercially available or easily obtainable imine (23a) with 1,4-dihalo-butene in presence of a base produces (23b), which after hydrolysis yields cyclopropyl amino acid (12b), having the allyl substituent syn to the carboxyl group. Resolution of the enantiomeric mixture (12b) results in (12b-1). The resolution is performed using art-known procedures such as enzymatic separation; crystallization with a chiral acid; or chemical derivatization; or by chiral column chromatography. Intermediates (12b) or (12b-1) may be coupled to the appropriate P2 derivatives as described above.

P1 building blocks for the preparation of compounds according to general formula (I) wherein $R^1$ is $—OR^7$ or $—NH—SO_2R^8$ can be prepared by reacting amino acids (24a) with the appropriate alcohol or amine respectively, under standard conditions for ester or amide formation. N-protected cyclopropyl amino acids (26a) are prepared by introducing a N-protecting group PG and removal of $PG^2$, and the amino acids (24a) are converted to the amides (12c-1) or esters (12c-2), which are subgroups of the intermediates (12c), as outlined in the following reaction scheme, wherein PG is as specified above.

(24b) or (24c) from which the amino protecting group is removed by standard methods such as those described above. This in turn results in the desired intermediate (12c-1) and (12c-2) respectively. Starting materials (26a) may be prepared from the above-mentioned intermediates (12b) by first introducing a N-protecting group PG and subsequent removal of the group $PG^2$.

In one embodiment the reaction of (24a) with (2b) is done by treatment of the starting amino acid with a coupling agent, for example CDI or the like, in a solvent like THF followed by reaction with (2b) in the presence of a base such as DBU.

Intermediates (12c-1) or (12c-2) in turn may be coupled to the appropriate proline, cyclopentane or cyclopentene derivatives as described above.

Synthesis of the P3 Building Blocks

The P3 building blocks are commercially available or can be prepared according to methodologies known to the skilled in the art. One of these methodologies is shown in the scheme below and uses monoacylated amines, such as trifluoroacetamide or a Boc-protected amine.

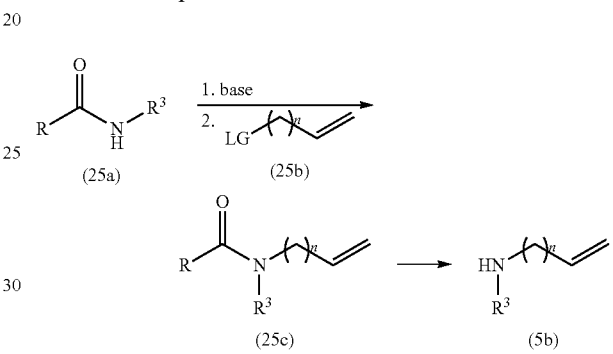

In the above scheme, R together with the CO group forms a N-protecting group, in particular R is t-butoxy, trifluoromethyl; $R^3$ and n are as defined above and LG is a leaving group, in particular halogen, e.g. chloro or bromo.

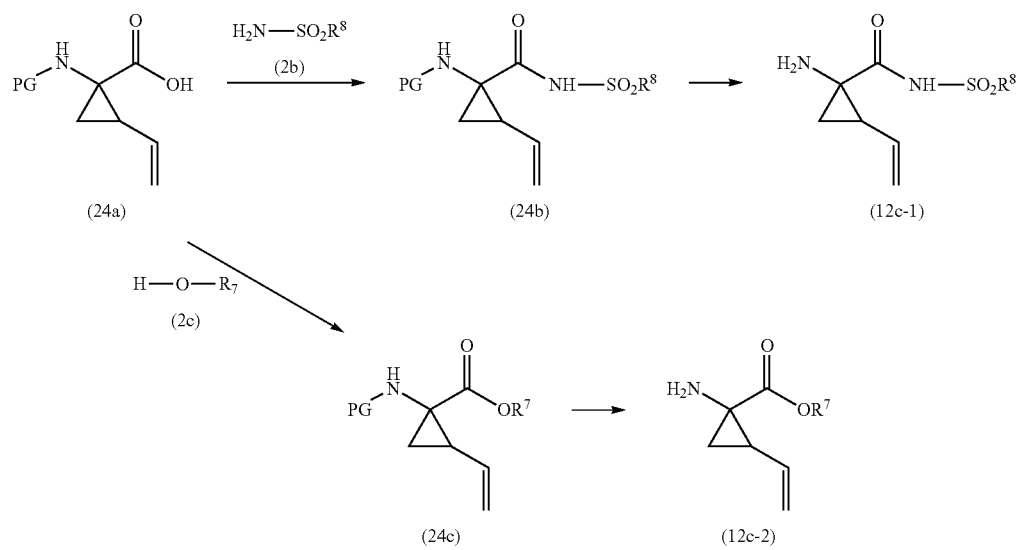

The reaction of (24a) with sulfonamide (2b) is an amide forming procedure. The similar reaction with (2c) is an ester forming reaction. Both can be performed following the procedures described above. This reaction yields intermediates The monoacylated amines (25a) are treated with a strong base such as sodium hydride and are subsequently reacted with a reagent LG-$C_{5-8}$alkenyl (25b), in particular halo$C_{5-8}$ alkenyl, to form the corresponding protected amines (25c). Deprotection of (25c) affords (5b), which are building blocks P3. Deprotection will depend on the functional group R, thus if R is t-butoxy, deprotection of the corresponding Boc-protected amine can be accomplished with an acidic treatment, e.g. trifluoroacetic acid. Alternatively, when R is for instance trifluoromethyl, removal of the R—CO group is accomplished with a base, e.g. sodium hydroxide.

The following scheme illustrates yet another method for preparing a P3 building block, namely a Gabriel synthesis of primary $C_{5-8}$alkenylamines, which can be carried out by the treatment of a phthalimide (26a) with a base, such as NaOH or KOH, and with (25b), which is as specified above, followed by hydrolysis of the intermediate N-alkenylimide to generate a primary $C_{5-8}$alkenylamine (5b-1).

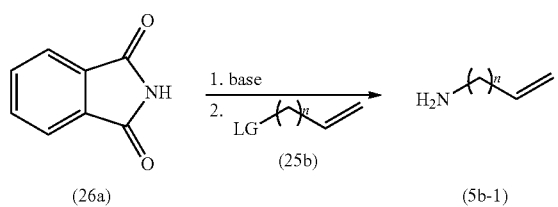

(26a)  (25b)  (5b-1)

In the above scheme, n is as defined above.

Compounds of formula (I) may be converted into each other following art-known functional group transformation reactions. For example, amino groups may be N-alkylated, nitro groups reduced to amino groups, a halo atom may be exchanged for another halo.

Pure stereochemically isomeric forms of the compounds of formula (I) may be obtained by the application of art-known procedures. Diastereomers may be separated by physical methods such as selective crystallization and chromatographic techniques, e.g., counter-current distribution, liquid chromatography and the like.

The compounds of formula (I) may be obtained as racemic mixtures of enantiomers, which can be separated from one another following art-known resolution procedures. The racemic compounds of formula (I) that are sufficiently basic or acidic may be converted into the corresponding diastereomeric salt forms by reaction with a suitable chiral acid, respectively chiral base. Said diastereomeric salt forms are subsequently separated, for example, by selective or fractional crystallization and the enantiomers are liberated therefrom by alkali or acid. An alternative manner of separating the enantiomeric forms of the compounds of formula (I) involves liquid chromatography, in particular liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound may be synthesized by stereospecific methods of preparation. These methods may advantageously employ enantiomerically pure starting materials.

In a further aspect, the present invention concerns a pharmaceutical composition comprising a therapeutically effective amount of a compound of formula (I) as specified herein, or a compound of any of the subgroups of compounds of formula (I) as specified herein, and a pharmaceutically acceptable carrier. A therapeutically effective amount in this context is an amount sufficient to prophylactically act against, to stabilize viral infection or to reduce viral infection, and in particular HCV viral infection, in infected subjects or subjects being at risk of being infected. In still a further aspect, this invention relates to a process of preparing a pharmaceutical composition as specified herein, which comprises intimately mixing a pharmaceutically acceptable carrier with a therapeutically effective amount of a compound of formula (I), as specified herein, or of a compound of any of the subgroups of compounds of formula (I) as specified herein.

Therefore, the compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form or metal complex, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations, which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin.

The compounds of the present invention may also be administered via oral inhalation or insufflation by means of methods and formulations employed in the art for administration via this way. Thus, in general the compounds of the present invention may be administered to the lungs in the form of a solution, a suspension or a dry powder, a solution being preferred. Any system developed for the delivery of solutions, suspensions or dry powders via oral inhalation or insufflation are suitable for the administration of the present compounds. Thus, the present invention also provides a pharmaceutical composition adapted for administration by inhalation or insufflation through the mouth comprising a compound of formula (I) and a pharmaceutically acceptable carrier. Preferably, the compounds of the present invention are administered via inhalation of a solution in nebulized or aerosolized doses.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compositions in accordance with this invention, including unit dosage forms, may contain the active ingredient in an amount that is in the range of about 0.1% to 70%, or about 0.5% to 50%, or about 1% to 25%, or about 5% to 20%, the remainder comprising the carrier, wherein the foregoing percentages are w/w versus the total weight of the composition or dosage form.

The compounds of formula (I) show antiviral properties. Viral infections and their associated diseases treatable using the compounds and methods of the present invention include those infections brought on by HCV and other pathogenic flaviviruses such as Yellow fever, Dengue fever (types 1-4), St. Louis encephalitis, Japanese encephalitis, Murray valley encephalitis, West Nile virus and Kunjin virus. The diseases associated with HCV include progressive liver fibrosis, inflammation and necrosis leading to cirrhosis, end-stage liver disease, and HCC; and for the other pathogenic flaviviruses the diseases include yellow fever, dengue fever, hemorrhagic fever and encephalitis. A number of the compounds of this invention moreover are active against mutated strains of HCV. Additionally, many of the compounds of this invention show a favorable pharmacokinetic profile and have attractive properties in terms of bioavailabilty, including an acceptable half-life, AUC (area under the curve) and peak values and lacking unfavorable phenomena such as insufficient quick onset and tissue retention.

The in vitro antiviral activity against HCV of the compounds of formula (I) was tested in a cellular HCV replicon system based on Lohmann et al. (1999) Science 285:110-113, with the further modifications described by Krieger et al. (2001) Journal of Virology 75: 4614-4624, which is further exemplified in the examples section. This model, while not a complete infection model for HCV, currently is widely accepted as an efficacious model of autonomous HCV RNA replication. Compounds exhibiting anti-HCV activity in this cellular model are considered as candidates for further development in the treatment of HCV infections in mammals. It will be appreciated that it is important to distinguish between compounds that specifically interfere with HCV functions from those that exert cytotoxic or cytostatic effects in the HCV replicon model, and as a consequence cause a decrease in HCV RNA or linked reporter enzyme concentration. Assays are known in the field for the evaluation of cellular cytotoxicity based for example on the activity of mitochondrial enzymes using fluorogenic redox dyes such as resazurin. Furthermore, cellular counter screens exist for the evaluation of non-selective inhibition of linked reporter gene activity, such as firefly luciferase. Appropriate cell types can be equipped by stable transfection with a luciferase reporter gene whose expression is dependent on a constitutively active gene promoter, and such cells can be used as a counter-screen to eliminate non-selective inhibitors.

Due to their antiviral properties, particularly their anti-HCV properties, the compounds of formula (I) or any subgroup thereof, their addition salts and stereochemically isomeric forms, are useful in the treatment of individuals experiencing a viral infection, particularly a HCV infection, and for the prophylaxis of these infections. In general, the compounds of the present invention may be useful in the treatment of warm-blooded animals infected with viruses, in particular flaviviruses such as HCV.

The compounds of the present invention or any subgroup thereof may therefore be used as medicines. Said use as a medicine or method of treatment comprises the systemic administration to viral infected subjects or to subjects susceptible to viral infections of an amount effective to combat the conditions associated with the viral infection, in particular the HCV infection.

The present invention also relates to the use of the present compounds or any subgroup thereof in the manufacture of a medicament for the treatment or the prevention of viral infections, particularly HCV infection.

The present invention furthermore relates to a method of treating a warm-blooded animal infected by a virus, or being at risk of infection by a virus, in particular by HCV, said method comprising the administration of an anti-virally effective amount of a compound of formula (I), as specified herein, or of a compound of any of the subgroups of compounds of formula (I), as specified herein.

Based on the test data presented hereinafter, it is contemplated that an effective daily dose is in the range of about 10 mg to about 2 g, or about 20 mg to about 1000 mg, or about 50 mg to about 750 mg, or about 100 mg to about 500 mg, for an average person of 70 kg. Doses may be adapted in function of weight and for paediatric applications. Daily doses may be administered q.d. or in multiple quantities such as b.i.d., t.i.d. or q.i.d.

Also, the combination of previously known anti-HCV compound, such as, for instance, interferon-α (IFN-α), pegylated interferon-α and/or ribavirin, and a compound of formula (I) can be used as a medicine in a combination therapy. The term "combination therapy" relates to a product containing mandatory (a) a compound of formula (I), and (b) optionally another anti-HCV compound, as a combined preparation for simultaneous, separate or sequential use in treatment of HCV infections, in particular, in the treatment of infections with HCV.

Anti-HCV compounds encompass agents selected from HCV polymerase inhibitors, NM283, R803, JTK-109 and JTK-003; HCV proteases (NS2-NS3 and NS3-NS4A) inhibitors, the compounds of WO02/18369 (see, e.g., page 273, lines 9-22 and page 274, line 4 to page 276, line 11), BILN-2061, VX-950, SCH 503034; inhibitors of other targets in the HCV life cycle, including helicase, and metalloprotease inhibitors, ISIS-14803; immunomodulatory agents such as, α-, β-, and γ-interferons, pegylated derivatized interferon-α compounds, compounds that stimulate the synthesis of interferon in cells, interleukins, compounds that enhance the development of type 1 helper T cell response, and thymosin; other antiviral agents such as ribavirin, amantadine, and telbivudine, inhibitors of internal ribosome entry, broad-spectrum viral inhibitors, such as IMPDH inhibitors (e.g., compounds of U.S. Pat. No. 5,807,876, U.S. Pat. No. 6,498,178, U.S. Pat. No. 6,344,465, U.S. Pat. No. 6,054,472, WO97/40028, WO98/40381, WO00/56331, and mycophenolic acid and derivatives thereof, and including, but not limited to VX-950, VX-497, VX-148, and/or VX-944); or combinations of any of the above.

Thus, to combat or treat HCV infections, the compounds of formula (I) may be co-administered in combination with for instance, interferon-α (IFN-α), pegylated interferon-α and/or ribavirin, as well as therapeutics based on antibodies targeted against HCV epitopes, small interfering RNA (siRNA), ribozymes, DNAzymes, antisense RNA, small molecule antagonists of for instance NS3 protease, NS3 helicase and NS5B polymerase.

Accordingly, the present invention relates to the use of a compound of formula (I) or any subgroup thereof as defined above for the manufacture of a medicament useful for inhibiting HCV activity in a mammal infected with HCV viruses, wherein said medicament is used in a combination therapy, said combination therapy preferably comprising a compound of formula (I) and another HCV inhibitory compound, e.g. (pegylated) IFN-α and/or ribavirin.

In still another aspect there are provided combinations of a compound of formula (I) as specified herein and an anti-HIV compound. The latter preferably are those HIV inhibitors that have a positive effect on drug metabolism and/or pharmacokinetics that improve bioavailabilty. An example of such an HIV inhibitor is ritonavir. Hence the present invention further provides a combination comprising (a) an HCV NS3/4a protease inhibitor of formula (I) or a pharmaceutically acceptable salt thereof; and (b) ritonavir or a pharmaceutically acceptable salt thereof.

The compound ritonavir, and pharmaceutically acceptable salts thereof, and methods for its preparation have been described in WO 94/14436. For preferred dosage forms of ritonavir, see U.S. Pat. No. 6,037,157, and the documents cited therein: U.S. Pat. No. 5,484,801, U.S. Ser. No. 08/402,690, and WO 95/07696 and WO 95/09614. Ritonavir has the following formula:

tion according to any one of the embodiments described herein and a pharmaceutically acceptable excipient. In particular, the present invention provides a pharmaceutical composition comprising (a) a therapeutically effective amount of an HCV NS3/4a protease inhibitor of the formula (I) or a pharmaceutically acceptable salt thereof, (b) a therapeutically effective amount of ritonavir or a pharmaceutically acceptable salt thereof, and (c) a pharmaceutically acceptable excipient. Optionally, the pharmaceutical composition further comprises an additional agent selected from an HCV polymerase inhibitor, an HCV protease inhibitor, an inhibitor of another target in the HCV life cycle, an immunomodulatory agent, an antiviral agent, and combinations thereof.

The compositions may be formulated into suitable pharmaceutical dosage forms such as the dosage forms described above. Each of the active ingredients may be formulated separately and the formulations may be co-administered or one formulation containing both and if desired further active ingredients may be provided.

As used herein, the term "composition" is intended to encompass a product comprising the specified ingredients, as well as any product that results, directly or indirectly, from the combination of the specified ingredients.

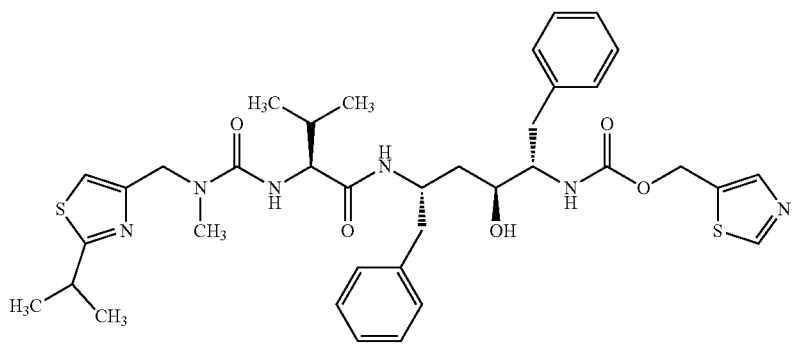 [SMILES: CC(C)c1nc(CN(C)C(=O)N[C@H](C(=O)N[C@@H](Cc2ccccc2)C[C@H](O)[C@H](Cc2ccccc2)NC(=O)OCc2cncs2)C(C)C)cs1]

In a further embodiment, the combination comprising (a) an HCV NS3/4a protease inhibitor of formula (I) or a pharmaceutically acceptable salt thereof; and (b) ritonavir or a pharmaceutically acceptable salt thereof; further comprises an additional anti-HCV compound selected from the compounds as described herein.

In one embodiment of the present invention there is provided a process for preparing a combination as described herein, comprising the step of combining an HCV NS3/4a protease inhibitor of formula (I) or a pharmaceutically acceptable salt thereof, and ritonavir or a pharmaceutically acceptable salt thereof. An alternative embodiment of this invention provides a process wherein the combination comprises one or more additional agents as described herein.

The combinations of the present invention may be used as medicaments. Said use as a medicine or method of treatment comprises the systemic administration to HCV-infected subjects of an amount effective to combat the conditions associated with HCV and other pathogenic flavi- and pestiviruses. Consequently, the combinations of the present invention can be used in the manufacture of a medicament useful for treating, preventing or combating infection or disease associated with HCV infection in a mammal, in particular for treating conditions associated with HCV and other pathogenic flavi- and pestiviruses.

In one embodiment of the present invention there is provided a pharmaceutical composition comprising a combina- In one embodiment the combinations provided herein may also be formulated as a combined preparation for simultaneous, separate or sequential use in HIV therapy. In such a case, the compound of general formula (I) or any subgroup thereof, is formulated in a pharmaceutical composition containing other pharmaceutically acceptable excipients, and ritonavir is formulated separately in a pharmaceutical composition containing other pharmaceutically acceptable excipients. Conveniently, these two separate pharmaceutical compositions can be part of a kit for simultaneous, separate or sequential use.

Thus, the individual components of the combination of the present invention can be administered separately at different times during the course of therapy or concurrently in divided or single combination forms. The present invention is therefore to be understood as embracing all such regimes of simultaneous or alternating treatment and the term "administering" is to be interpreted accordingly. In a preferred embodiment, the separate dosage forms are administered about simultaneously.

In one embodiment, the combination of the present invention contains an amount of ritonavir, or a pharmaceutically acceptable salt thereof, which is sufficient to clinically improve the bioavailability of the HCV NS3/4a protease inhibitor of formula (I) relative to the bioavailability when said HCV NS3/4a protease inhibitor of formula (I) is administered alone.

In another embodiment, the combination of the present invention contains an amount of ritonavir, or a pharmaceutically acceptable salt thereof, which is sufficient to increase at least one of the pharmacokinetic variables of the HCV NS3/4a protease inhibitor of formula (I) selected from $t_{1/2}$, $C_{min}$, $C_{max}$, $C_{ss}$, AUC at 12 hours, or AUC at 24 hours, relative to said at least one pharmacokinetic variable when the HCV NS3/4a protease inhibitor of formula (I) is administered alone.

A further embodiment relates to a method for improving the bioavailability of a HCV NS3/4a protease inhibitor by administering to an individual in need of such improvement, a combination as defined herein comprising a therapeutically effective amount of each component of said combination.

In a further embodiment, the invention relates to the use of ritonavir or a pharmaceutically acceptable salt thereof, as an improver of at least one of the pharmacokinetic variables of a HCV NS3/4a protease inhibitor of formula (I) selected from $t_{1/2}$, $C_{min}$, $C_{max}$, $C_{ss}$, AUC at 12 hours, or AUC at 24 hours; with the proviso that said use is not practiced in the human or animal body.

The term "individual" as used herein refers to an animal, preferably a mammal, most preferably a human, who has been the object of treatment, observation or experiment.

Bioavailability is defined as the fraction of administered dose reaching systemic circulation. $t_{1/2}$ represents the half life or time taken for the plasma concentration to fall to half its original value. $C_{ss}$ is the steady state concentration, i.e. the concentration at which the rate of input of drug equals the rate of elimination. $C_{min}$ is defined as the lowest (minimum) concentration measured during the dosing interval. $C_{max}$ represents the highest (maximum) concentration measured during the dosing interval. AUC is defined as the area under the plasma concentration-time curve for a defined period of time.

The combinations of this invention can be administered to humans in dosage ranges specific for each component comprised in said combinations. The components comprised in said combinations can be administered together or separately. The NS3/4a protease inhibitors of formula (I) or any subgroup thereof, and ritonavir or a pharmaceutically acceptable salt or ester thereof, may have dosage levels in the range of about 0.02 to about 3.0 grams-per-day, or in the range of about 0.03 to about 2.0 grams-per-day, or in the range of about 50 mg to about 1000 mg per day, or in the range of about 100 mg to about 500 mg per day.

When the HCV NS3/4a protease inhibitor of formula (I) and ritonavir are administered in combination, the weight ratio of the HCV NS3/4a protease inhibitor of formula (I) to ritonavir is suitably in the range of from about 40:1 to about 1:15, or from about 30:1 to about 1:15, or from about 15:1 to about 1:15, typically from about 10:1 to about 1:10, and more typically from about 8:1 to about 1:8. Also useful are weight ratios of the HCV NS3/4a protease inhibitors of formula (I) to ritonavir ranging from about 6:1 to about 1:6, or from about 4:1 to about 1:4, or from about 3:1 to about 1:3, or from about 2:1 to about 1:2, or from about 1.5:1 to about 1:1.5. In one aspect, the amount by weight of the HCV NS3/4a protease inhibitors of formula (I) is equal to or greater than that of ritonavir, wherein the weight ratio of the HCV NS3/4a protease inhibitor of formula (I) to ritonavir is suitably in the range of from about 1:1 to about 15:1, typically from about 1:1 to about 10:1, and more typically from about 1:1 to about 8:1.

Also useful are weight ratios of the HCV NS3/4a protease inhibitor of formula (I) to ritonavir ranging from about 1:1 to about 6:1, or from about 1:1 to about 5:1, or from about 1:1 to about 4:1, or from about 3:2 to about 3:1, or from about 1:1 to about 2:1 or from about 1:1 to about 1.5:1.

The term "therapeutically effective amount" as used herein means that amount of active compound or component or pharmaceutical agent that elicits the biological or medicinal response in a tissue, system, animal or human that is being sought, in the light of the present invention, by a researcher, veterinarian, medical doctor or other clinician, which includes alleviation of the symptoms of the disease being treated. Since the instant invention refers to combinations comprising two or more agents, the "therapeutically effective amount" is that amount of the agents taken together so that the combined effect elicits the desired biological or medicinal response. For example, the therapeutically effective amount of a composition comprising (a) the compound of formula (I) and (b) ritonavir, would be the amount of the compound of formula (I) and the amount of ritonavir that when taken together have a combined effect that is therapeutically effective.

In general it is contemplated that an antiviral effective daily amount would be from 0.01 mg/kg to 500 mg/kg body weight, more preferably from 0.1 mg/kg to 50 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines.

According to one embodiment, the HCV NS3/4a protease inhibitor of formula (I) and ritonavir may be co-administered once or twice a day, preferably orally, wherein the amount of the compounds of formula (I) per dose is from about 1 to about 2500 mg, and the amount of ritonavir per dose is from 1 to about 2500 mg. In another embodiment, the amounts per dose for once or twice-daily co-administration are from about 50 to about 1500 mg of the compound of formula (I) and from about 50 to about 1500 mg of ritonavir. In still another embodiment, the amounts per dose for once or twice daily co-administration are from about 100 to about 1000 mg of the compound of formula (I) and from about 100 to about 800 mg of ritonavir. In yet another embodiment, the amounts per dose for once or twice-daily co-administration are from about 150 to about 800 mg of the compound of formula (I) and from about 100 to about 600 mg of ritonavir. In yet another embodiment, the amounts per dose for once or twice daily co-administration are from about 200 to about 600 mg of the compound of formula (I) and from about 100 to about 400 mg of ritonavir. In yet another embodiment, the amounts per dose for once or twice-daily co-administration are from about 200 to about 600 mg of the compound of formula (I) and from about 20 to about 300 mg of ritonavir. In yet another embodiment, the amounts per dose for once or twice daily co-administration are from about 100 to about 400 mg of the compound of formula (I) and from about 40 to about 100 mg of ritonavir.

Exemplary combinations of the compound of formula (I) (mg)/ritonavir (mg) for once or twice daily dosage include 50/100, 100/100, 150/100, 200/100, 250/100, 300/100, 350/100, 400/100, 450/100, 50/133, 100/133, 150/133, 200/133, 250/133, 300/133, 50/150, 100/150, 150/150, 200/150, 250/150, 50/200, 100/200, 150/200, 200/200, 250/200, 300/200, 50/300, 80/300, 150/300, 200/300, 250/300, 300/300, 200/600, 400/600, 600/600, 800/600, 1000/600, 200/666, 400/666, 600/666, 800/666, 1000/666, 1200/666, 200/800, 400/800, 600/800, 800/800, 1000/800, 1200/800, 200/1200, 400/1200, 600/1200, 800/1200, 1000/1200, and 1200/1200. Other exemplary combinations of the compound of formula (I) (mg)/ritonavir (mg) for once or twice daily dosage include 1200/400, 800/400, 600/400, 400/200, 600/200, 600/100, 500/100, 400/50, 300/50, and 200/50. All above ratios are mg/mg.

In one embodiment of the present invention there is provided an article of manufacture comprising a composition effective to treat an HCV infection or to inhibit the NS3 protease of HCV; and packaging material comprising a label which indicates that the composition can be used to treat infection by the hepatitis C virus; wherein the composition comprises a compound of the formula (I) or any subgroup thereof, or the combinations as described herein.

The compounds and combinations of the present invention can be used in high-throughput target-analyte assays such as those for measuring the efficacy of said combination in HCV treatment.

EXAMPLES

The following examples are intended to illustrate the present invention and not to limit it thereto.

Example 1

Preparation of 17-[2-ethoxy-7-methoxy-8-methylquinolin-4-yloxy]-13-methyl-2,14-dioxo-3,13-diazatricyclo[13.3.0.0$^{4,6}$]octadec-7-ene-4-carboxylic acid (2)

Step A

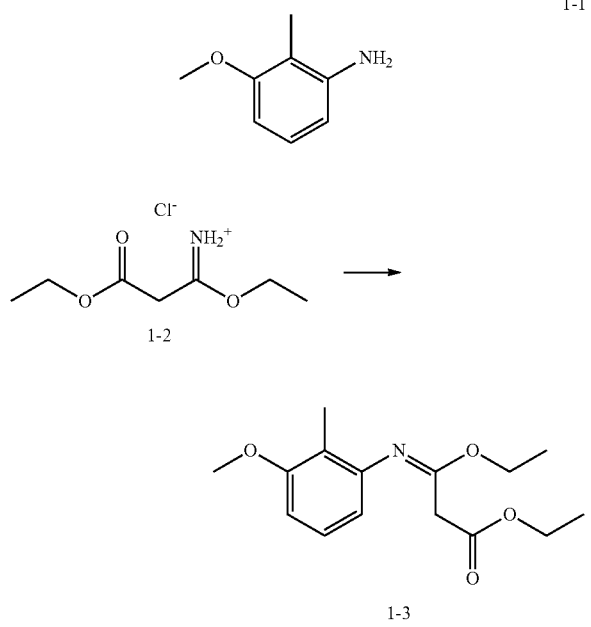

A solution of 3-methoxy-2-methylaniline (1.09 g, 7.95 mmol) and ethyl 3-ethoxy-3-iminopropionate hydrochloride (1.44 g, 7.36 mmol) in ethanol (15 mL) was stirred at room temperature under nitrogen for 48 h. Then, the solvent was evaporated under reduced pressure. The residue was triturated in ether and filtered off. The filtrate was evaporated then the residue was purified by column chromatography (ethyl acetate/heptane, 10:90) to give 1.97 g (89%) of the target product (1-3): m/z=280 (M+H)$^+$.

Step B: Synthesis of 4-hydroxy-2-ethoxy-7-methoxy-8-methylquinoline (1-4)

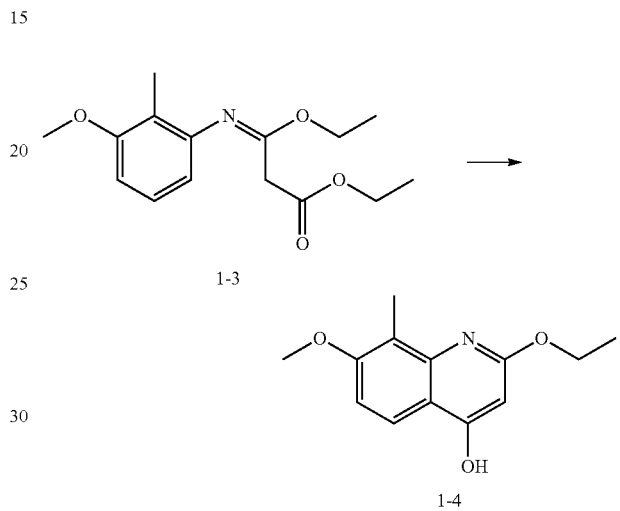

A mixture of (1-3) (5.54 g, 19.8 mmol) in diphenylether (20 mL) was heated at 250° C. for 30 minutes. Then, the reaction mixture was cooled down to room temperature. Purification by column chromatography (gradient heptane to ethyl acetate/heptane, 70:30) followed by a recrystallization from ethyl acetate afforded 2.46 g (53%) of the title product (1-4) as yellow needles: m/z=234 (M+H)$^+$.

Step C: Synthesis of Intermediate (1-5)

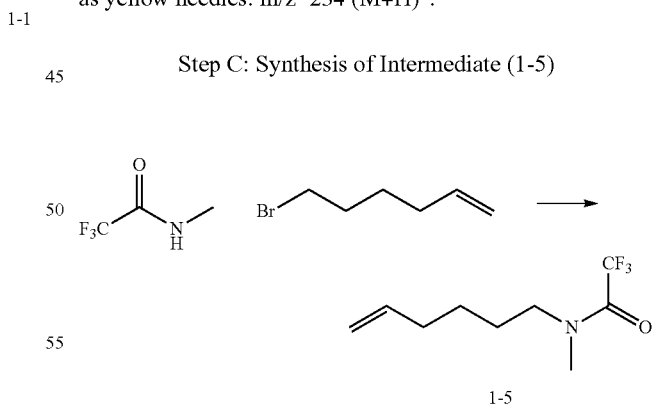

Sodium hydride (1.05 eq) was slowly added at 0° C. to a solution of N-methyltrifluoro-acetamide (25 g) in DMF (140 mL). The mixture was stirred for 1 h at room temperature under nitrogen. Then, a solution of bromohexene (32.1 g) in DMF (25 mL) was added dropwise and the mixture was heated to 70° C. for 12 hours. The reaction mixture was poured on water (200 mL) and extracted with diethylether (4×50 mL), dried (MgSO$_4$), filtered and evaporated to give 35 g of the target product (1-5) as a yellowish oil which was used without further purification in the next step.

Step D: Synthesis of (hex-5-enyl)(methyl)amine (1-6)

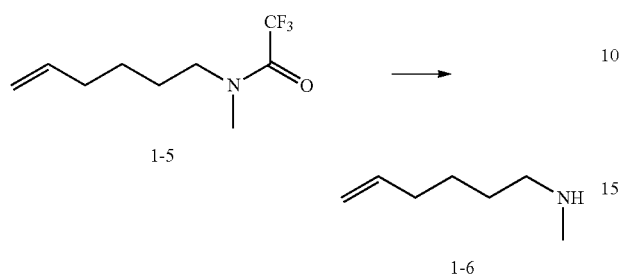

A solution of potassium hydroxide (187.7 g) in water (130 mL) was added dropwise to a solution of (1-5) (35 g) in methanol (200 mL). The mixture was stirred at room temperature for 12 hours. Then, the reaction mixture was poured on water (100 mL) and extracted with ether (4×50 mL), dried (MgSO$_4$), filtered and the ether was distilled under atmospheric pressure. The resulting oil was purified by distillation under vacuum (13 mm Hg pressure, 50° C.) to give 7.4 g (34%) of the title product (1-6) as a colourless oil: $^1$H-NMR (CDCl$_3$): δ 5.8 (m, 1H), 5 (ddd, J=17.2 Hz, 3.5 Hz, 1.8 Hz, 1H), 4.95 (m, 1H), 2.5 (t, J=7.0 Hz, 2H), 2.43 (s, 3H), 2.08 (q, J=7.0 Hz, 2H), 1.4 (m, 4H), 1.3 (br s, 1H).

Step E: Synthesis of Intermediate (1-8)

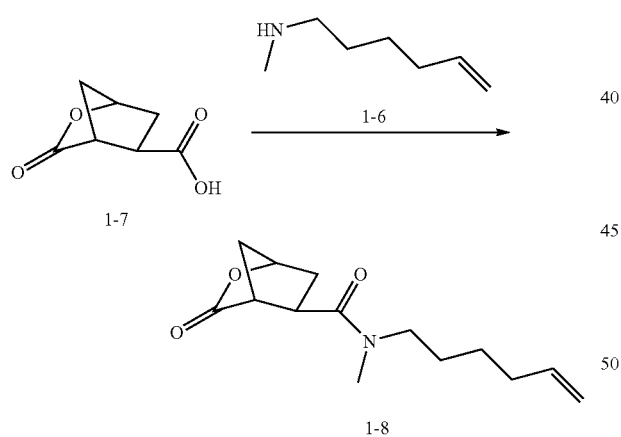

3-Oxo-2-oxa-bicyclo[2.2.1]heptane-5-carboxylic acid (1-7) (500 mg, 3.2 mmol) in 4 mL DMF was added at 0° C. to HATU (2-(1H-7-azabenzotriazol-1-yl)-1,1,3,3-tetramethyl uronium hexafluorophosphate methanaminium; 1.34 g, 3.52 mmol) and N-methylhex-5-enylamine ((1-6), 435 mg, 3.84 mmol) in DMF (3 mL), followed by DIPEA. After stirring for 40 min at 0° C., the mixture was stirred at room temperature for 5 h. Then, the solvent was evaporated, the residue dissolved in ethyl acetate (70 mL) and washed with saturated NaHCO$_3$ (10 mL). The aqueous layer was extracted with ethyl acetate (2×25 mL). The organic layers were combined, washed with saturated NaCl (20 mL), dried (Na$_2$SO$_4$), and evaporated. Purification by flash chromatography (ethyl acetate/petroleum ether, 2:1) afforded 550 mg (68%) of the target product (1-8) as a colorless oil: m/z=252 (M+H)$^+$.

Step F: Synthesis of Intermediate (1-9)

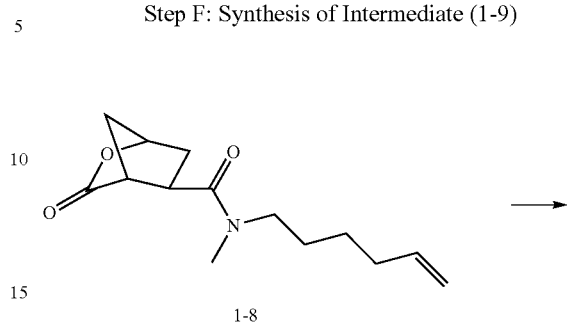

A solution of LiOH (105 mg in 4 mL of water) was added at 0° C. to the lactone amide (1-8). After 1 h, the conversion was completed (HPLC). The mixture was acidified to pH 2-3 with 1N HCl, extracted with ethyl acetate, dried (MgSO$_4$), evaporated, co-evaporated with toluene several times, and dried under high vacuum overnight to give 520 mg (88%) of the target product (1-9): m/z=270 (M+H)$^+$.

Step G: Synthesis of Intermediate (1-11)

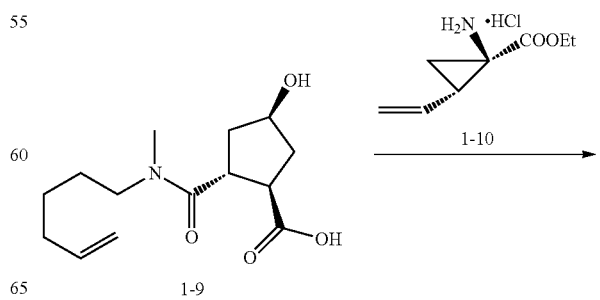

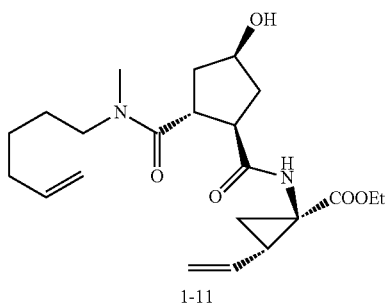

1-11

The 1-(amino)-2-(vinyl)cyclopropanecarboxylic acid ethyl ester hydrochloride (1-10) (4.92 g, 31.7 mmol) and HATU (12.6 g, 33.2 mmol) were added to (1-9) (8.14 g, 30.2 mmol).

The mixture was cooled in an ice bath under argon, and then DMF (100 mL) and DIPEA (12.5 mL, 11.5 mmol) were successively added. After 30 min at 0° C., the solution was stirred at room temperature for an additional 3 h. Then, the reaction mixture was partitioned between ethyl acetate and water, washed successively with 0.5 N HCl (20 mL) and saturated NaCl (2×20 mL), and dried (Na$_2$SO$_4$). Purification by flash chromatography (ethyl acetate/CH$_2$Cl$_2$/petroleum ether, 1:1:1) afforded 7.41 g (60%) of the target product (1-11) as a colorless oil: m/z=407 (M+H)$^+$.

Step H: Synthesis of Intermediate (1-12)

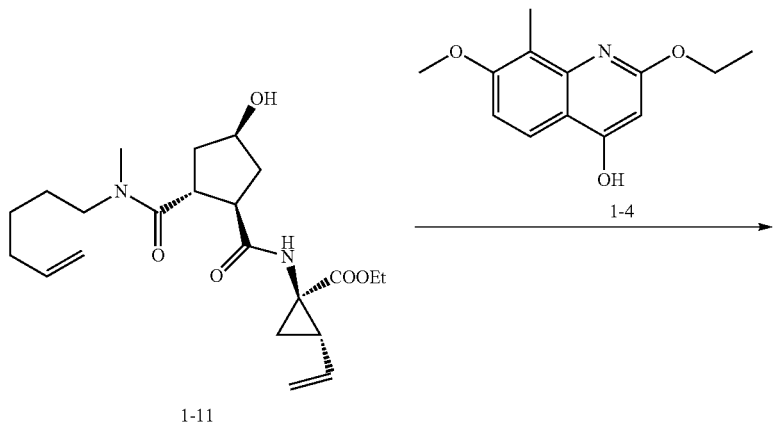

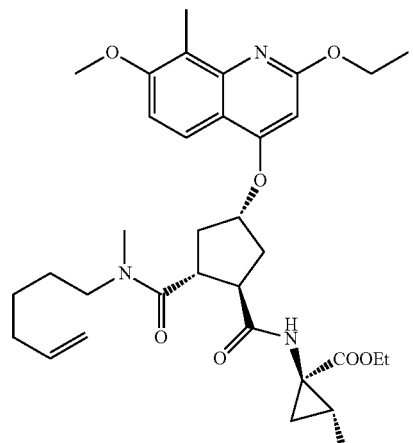

1-12

DIAD (271 mg, 1.30 mmol) was added at −20° C. under nitrogen atmosphere to a solution of (1-11) (351 mg, 0.86 mmol), quinoline (1-4) (207 mg, 0.89 mmol) and triphenylphosphine (387 mg, 1.5 mmol) in dry THF (15 mL). Next, the reaction was warmed up to room temperature. After 24 h, the reaction mixture was quenched with ice-cold water, and then extracted with ether. The organic layer was successively dried (Na$_2$SO$_4$), filtered and evaporated. The residue was purified by flash column chromatography (ethyl acetate/CH$_2$Cl$_2$, 1:9) to give 520 mg (92%) of the target product (1-12): m/z=622 (M+H)$^+$.

Step I: Synthesis of (1)

and the residue purified by silica gel chromatography (ether) to give 279 mg (62%) of the target product (1): m/z=594 (M+H)$^+$.

Step J: Synthesis of 17-[2-ethoxy-7-methoxy-8-methylquinolin-4-yloxy]-13-methyl-2,14-dioxo-3,13-diazatricyclo[13.3.0.0$^{4,6}$]octadec-7-ene-4-carboxylic acid (2)

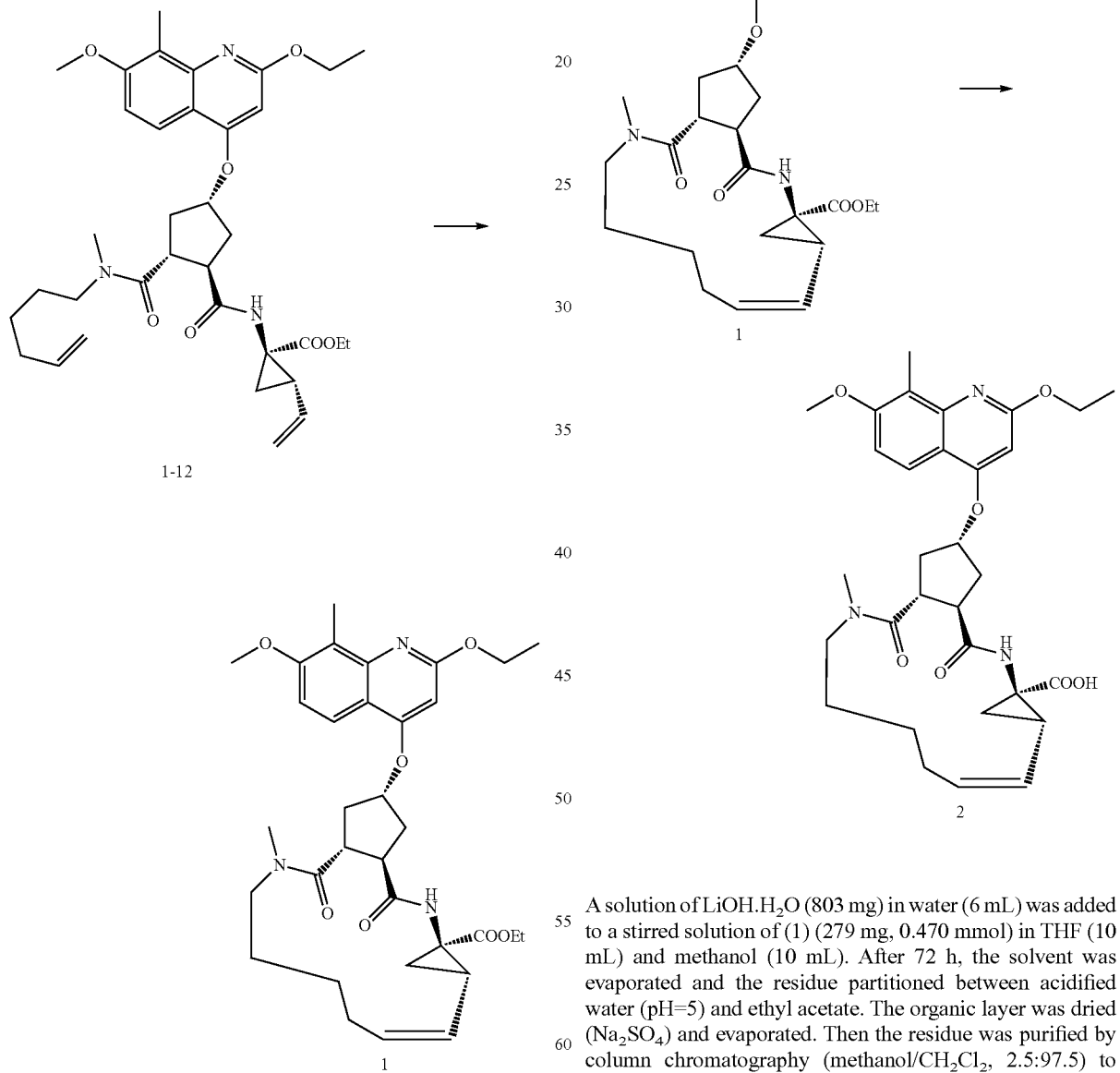

A solution of (1-12) (520 mg, 0.753 mmol) and Hoveyda-Grubbs 1$^{st}$ generation catalyst (48 mg, 0.080 mmol) in dried and degassed 1,2-dichloroethane (400 mL) was heated at 80° C. under nitrogen for 36 h. Then, the solvent was evaporated A solution of LiOH.H$_2$O (803 mg) in water (6 mL) was added to a stirred solution of (1) (279 mg, 0.470 mmol) in THF (10 mL) and methanol (10 mL). After 72 h, the solvent was evaporated and the residue partitioned between acidified water (pH=5) and ethyl acetate. The organic layer was dried (Na$_2$SO$_4$) and evaporated. Then the residue was purified by column chromatography (methanol/CH$_2$Cl$_2$, 2.5:97.5) to give the title product (2) as a white powder: m/z=566 (M+H)$^+$.
$^1$H NMR (CDCl$_3$): 1.10-1.14 (m, 3H), 1.10-1.21 (m, 1H), 1.31-1.42 (m, 1H), 1.40-1.50 (m, 4H), 1.50-1.65 (m, 1H), 1.68-1.83 (m, 2H), 1.83-1.95 (m, 2H), 2.10-2.20 (m, 1H), 2.21-2.34 (m, 2H), 2.35-2.49 (m, 1H), 2.50-2.65 (m, 5H), 2.97 (s, 3H), 3.18-3.30 (m, 1H), 3.92 (s, 3H), 4.48-4.62 (m, 3H), 4.80-4.88 (m, 1H), 5.13-5.23 (m, 1H), 5.60-5.70 (m, 1H), 7.00 (d, 1H), 7.41 (s, 1H), 7.81 (d, 1H).

Example 2

Preparation of N-[17-[2-ethoxy-7-methoxy-8-methylquinolin-4-yloxy]-13-methyl-2,14-dioxo-3,13-diazatricyclo[13.3.0.0^{4,6}]octadec-7-ene-4-carbonyl](cyclo-propyl)sulfonamide (3)

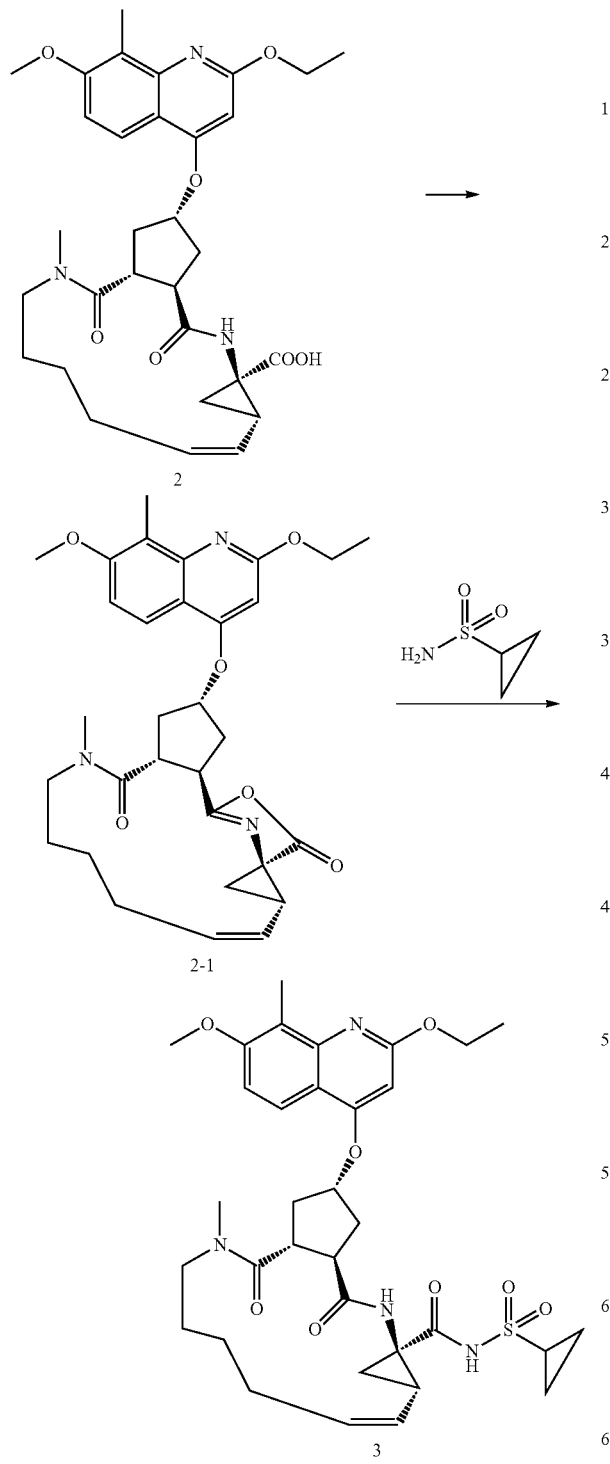

A mixture of (2) (182 mg, 0.32 mmol) and CDI (139 mg, 0.29 mmol) in dry THF (10 mL) was heated at reflux for 1.5 h under nitrogen. LCMS analysis showed one peak of the intermediate (2-1) (a stable intermediate, which can be isolated by purification on silica gel). The reaction mixture was cooled to room temperature and cyclopropyl-sulfonamide (93 mg, 0.76 mmol) was added. Then, DBU (138 mg, 0.91 mmol) was added. The reaction mixture was stirred at room temperature for 1 h, then heated at 55° C. for 12 h. Next, the solvent was evaporated, and the residue partitioned between ethyl acetate and acidic water (pH=3). The organic layer was dried (Na$_2$SO$_4$) and evaporated. The crude material was purified by column chromatography (ethyl acetate/CH$_2$Cl$_2$, 1:9). The residue was sonicated in water for 1 h, filtered off and washed with isopropylether to give the title product (3) as a white powder: m/z=669 (M+H)$^+$. $^1$H NMR (CDCl$_3$): 0.90-1.30 (m, 5H), 1.31-1.52 (m, 6H), 1.61-1.72 (m, 1H), 1.73-1.99 (m, 3H), 2.09-2.20 (m, 1H), 2.30-2.42 (m, 2H), 2.48-2.62 (m, 5H), 2.70-2.83 (m, 1H), 3.01 (s, 3H), 3.30-3.41 (m, 2H), 3.94 (s, 3H), 4.50-4.73 (m, 3H), 5.05 (t, J=10.0 Hz, 2H), 5.62-5.69 (m, 1H), 5.95 (s, 1H), 6.35 (br s, 1H), 7.01 (d, J=9.1 Hz, 1H), 7.85 (d, J=9.1 Hz, 1H), 10.8 (br s, 1H).

Example 3

Preparation of 17-[2-ethoxy-7-methoxyquinolin-4-yloxy]-13-methyl-2,14-dioxo-3,13-diazatricyclo[13.3.0.0$^{4,6}$]octadec-7-ene-4-carboxylic acid (4)

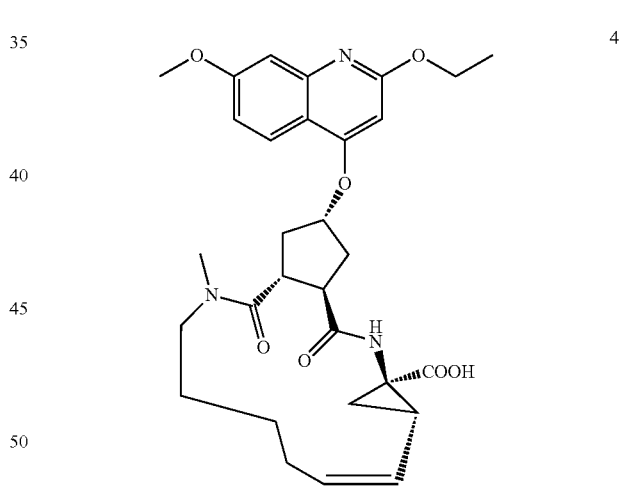

The title compound (4) was prepared from 3-methoxyaniline following the procedure (Steps A-J) reported for synthesis of 17-[2-ethoxy-7-methoxy-8-methylquinolin-4-yloxy]-13-methyl-2,14-dioxo-3,13-diazatricyclo[13.3.0.0$^{4,6}$]octadec-7-ene-4-carboxylic acid (2): m/z=552 (M+H)$^+$.

$^1$HNMR (CDCl$_3$): 1.10-1.21 (m, 1H), 1.31-1.42 (m, 1H), 1.45 (t, J=7.1 Hz, 3H), 1.50-1.65 (m, 1H), 1.71-1.85 (m, 2H), 1.85-2.00 (m, 3H), 2.15-2.51 (m, 7H), 3.00 (s, 3H), 3.21-3.32 (m, 1H), 3.51-3.62 (m, 1H), 3.91 (s, 3H), 4.51-4.62 (m, 3H), 4.91-4.96 (m, 1H), 5.15 (dd, J=10.0 and J=8.0 Hz, 1H), 5.65 (ddd, J=10.0, J=6.6 Hz, J=6.7 Hz, 1H), 6.00 (s, 1H), 6.95 (dd, J=8.9 Hz, J=2.3 Hz, 1H), 7.22 (s, 1H), 7.26 (d, J=2.3 Hz, 1H), 7.88 (d, J=8.9 Hz, 1H).

Example 4

Preparation of N-[17-[2-ethoxy-7-methoxyquinolin-4-yloxy]-13-methyl-2,14-dioxo-3,13-diazatricyclo[13.3.0.0^{4,6}]octadec-7-ene-4-carbonyl](cyclopropyl)-sulfonamide (5)

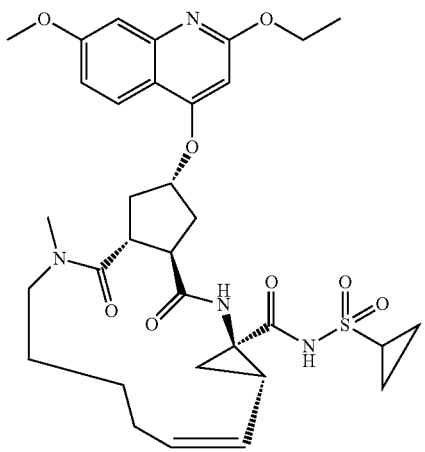

The title compound (5) was prepared from 17-[2-ethoxy-7-methoxyquinolin-4-yloxy]-13-methyl-2,14-dioxo-3,13-diazatricyclo[13.3.0.0^{4,6}]octadec-7-ene-4-carboxylic acid (4) following the procedure reported for synthesis of N-[17-[2-ethoxy-7-methoxy-8-methylquinolin-4-yloxy]-13-methyl-2,14-dioxo-3,13-diazatricyclo[13.3.0.0^{4,6}]octadec-7-ene-4-carbonyl](cyclopropyl)sulfonamide (3): m/z=555 (M+H)$^+$.
$^1$H NMR (CDCl$_3$): 0.80-0.90 (m, 1H), 0.92-1.0 (m, 4H), 1.00-1.3 (m, 3H), 1.41 (t, J=7.1 Hz, 3H), 1.45-1.71 (m, 2H), 1.8-1.95 (m, 4H), 2.21-2.62 (m, 4H), 2.73-2.81 (m, 1H), 2.9-2.94 (m, 1H), 3.0 (s, 3H), 3.31-3.41 (m, 1H), 3.90 (s, 3H), 4.44 (q, J=7.1 Hz, 2H), 5.0-5.08 (m, 2H), 5.6-5.65 (m, 1H), 5.98 (s, 1H), 6.8 (br s, 1H), 7.10 (dd, J=9.1 Hz and J=2.5 Hz, 1H), 7.12 (d, J=2.5 Hz, 1H), 7.28 (s, 1H), 7.9 (d, J=9.1 Hz, 1H), 11.02 (br s, 1H).

Example 5

Preparation of 17-[8-bromo-2-ethoxy-7-methoxyquinolin-4-yloxy]-13-methyl-2,14-dioxo-3,13-diazatricyclo[13.3.0.0^{4,6}]octadec-7-ene-4-carboxylic acid (6)

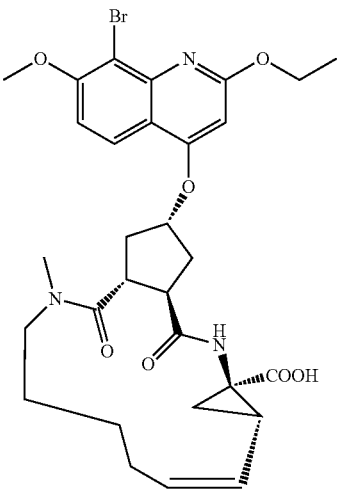

The title compound (6) was prepared from 2-bromo-3-methoxyaniline following the procedure (Steps A-J) reported for synthesis of 17-[2-ethoxy-7-methoxy-8-methyl-quinolin-4-yloxy]-13-methyl-2,14-dioxo-3,13-diazatricyclo[13.3.0.0^{4,6}]octadec-7-ene-4-carboxylic acid (2): m/z=631 (M+H)$^+$.

Example 6

Preparation of N-[17-[8-bromo-2-ethoxy-7-methoxyquinolin-4-yloxy]-13-methyl-2,14-dioxo-3,13-diazatricyclo[13.3.0.0^{4,6}]octadec-7-ene-4-carbonyl](cyclo-propyl)sulfonamide (7)

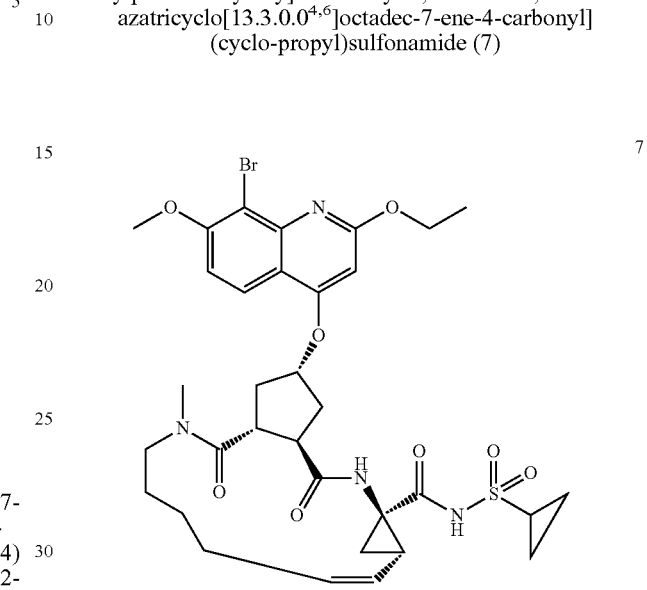

The title compound (7) was prepared from 17-[8-bromo-2-ethoxy-7-methoxyquinolin-4-yloxy]-13-methyl-2,14-dioxo-3,13-diazatricyclo[13.3.0.0^{4,6}]octadec-7-ene-4-carboxylic acid (6) following the procedure reported for synthesis of N-[17-[2-ethoxy-7-methoxy-8-methylquinolin-4-yloxy]-13-methyl-2,14-dioxo-3,13-diaza-tricyclo[13.3.0.0^{4,6}]octadec-7-ene-4-carbonyl](cyclopropyl)sulfonamide (3): m/z=734 (M+H)$^+$.

Example 7

Preparation of 17-[2-ethoxy-8,9-dihydrofuro[2,3-h]quinolin-4-yloxy]-13-methyl-2,14-dioxo-3,13-diazatricyclo[13.3.0.0^{4,6}]octadec-7-ene-4-carboxylic acid (8)

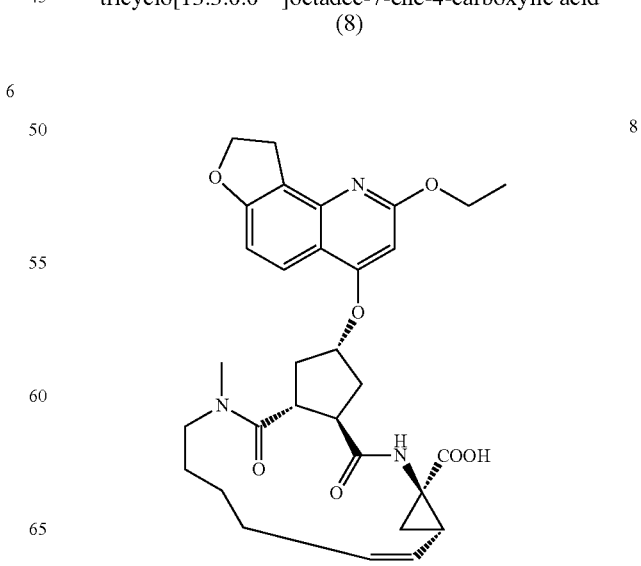

The title compound (8) was prepared from 4-amino-2,3-dihydrobenzofurane following the procedure (Steps A-J) reported for synthesis of 17-[2-ethoxy-7-methoxy-8-methylquinolin-4-yloxy]-13-methyl-2,14-dioxo-3,13-diazatricyclo[13.3.0.046]-octadec-7-ene-4-carboxylic acid (2): m/z=564 (M+H)+.

Example 8

Preparation of N-[17-[2-ethoxy-8,9-dihydrofuro[2,3-h]quinolin-4-yloxy]-13-methyl-2,14-dioxo-3,13-diazatricyclo[13.3.0.0$^{4,6}$]octadec-7-ene-4-carbonyl](cyclo-propyl)sulfonamide (9)

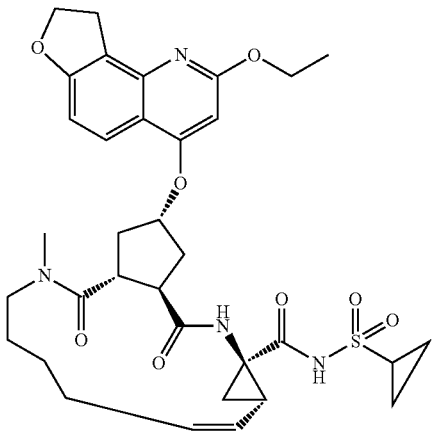

9

The title compound (9) was prepared from 17-[2-ethoxy-8,9-dihydrofuro[2,3-h]-quinolin-4-yloxy]-13-methyl-2,14-dioxo-3,13-diazatricyclo[13.3.0.0$^{4,6}$]octadec-7-ene-4-carboxylic acid (8) following the procedure reported for synthesis of N-[17-[2-ethoxy-7-methoxy-8-methylquinolin-4-yloxy]-13-methyl-2,14-dioxo-3,13-diazatricyclo[13.3.0.0$^{4,6}$]octadec-7-ene-4-carbonyl](cyclopropyl)sulfonamide (3): m/z=667 (M+H)+.

Example 9

Preparation of 17-[8-chloro-2-ethoxyquinolin-4-yloxy]-13-methyl-2,14-dioxo-3,13-diazatricyclo[13.3.0.0$^{4,6}$]octadec-7-ene-4-carboxylic acid (10).

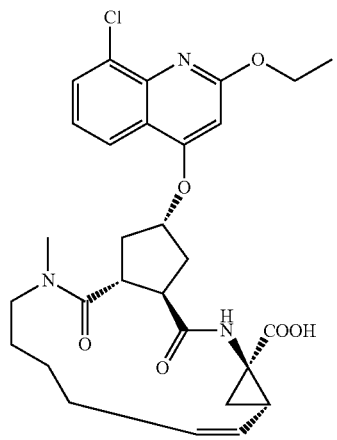

10

The title compound (10) was prepared from 2-chloroaniline following the procedure (Steps A-J) reported for synthesis of 17-[2-ethoxy-7-methoxy-8-methylquinolin-4-yl-oxy]-13-methyl-2,14-dioxo-3,13-diazatricyclo[13.3.0.0$^{4,6}$]octadec-7-ene-4-carboxylic acid (2): m/z=556 (M+H)+.

Example 10

Preparation of N-[17-[8-chloro-2-ethoxyquinolin-4-yloxy]-13-methyl-2,14-dioxo-3,13-diazatricyclo[13.3.0.0$^{4,6}$]octadec-7-ene-4-carbonyl](cyclopropyl)-sulfonamide (11)

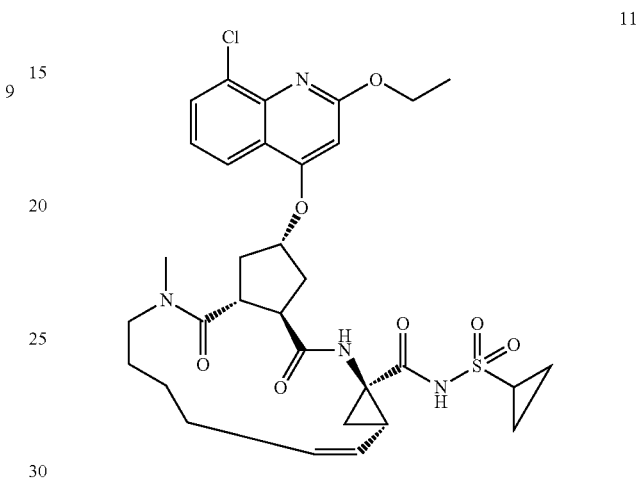

11

The title compound (11) was prepared from 17-[8-chloro-2-ethoxyquinolin-4-yloxy]-13-methyl-2,14-dioxo-3,13-diazatricyclo[13.3.0.0$^{4,6}$]octadec-7-ene-4-carboxylic acid (10) following the procedure reported for synthesis of N-[17-[2-ethoxy-7-methoxy-8-methylquinolin-4-yloxy]-13-methyl-2,14-dioxo-3,13-diazatricyclo-[13.3.0.0$^{4,6}$]octadec-7-ene-4-carbonyl](cyclopropyl)sulfonamide (3): m/z=659 (M+H)+.

Example 11

Preparation of 17-[2-ethoxy-8-methylquinolin-4-yloxy]-13-methyl-2,14-dioxo-3,13-diazatricyclo[13.3.0.0$^{4,6}$]octadec-7-ene-4-carboxylic acid (12).

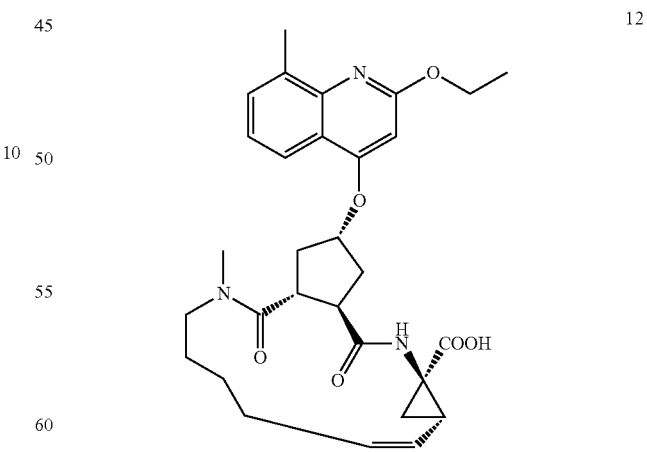

12

The title compound (12) was prepared from 2-methylaniline following the procedure (Steps A-J) reported for synthesis of 17-[2-ethoxy-7-methoxy-8-methylquinolin-4-yloxy]-13-methyl-2,14-dioxo-3,13-diazatricyclo[13.3.0.0$^{4,6}$]octadec-7-ene-4-carboxylic acid (2): m/z=536 (M+H)+.

Example 12

Preparation of N-[17-[2-ethoxy-8-methyl quinolin-4-yloxy]-13-methyl-2,14-dioxo-3,13-diazatricyclo[13.3.0.0⁴,⁶]octadec-7-ene-4-carbonyl](cyclopropyl)sulfonamide (13)

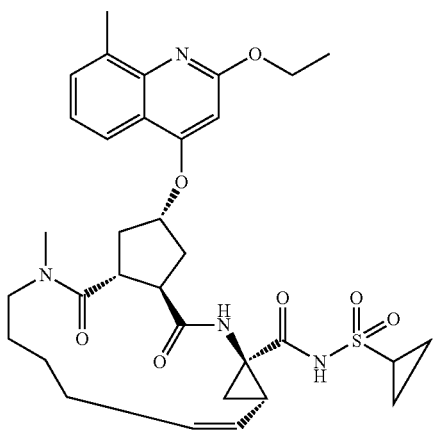

The title compound (13) was prepared from 17-[2-ethoxy-8-methylquinolin-4-yloxy]-13-methyl-2,14-dioxo-3,13-diazatricyclo[13.3.0.0⁴,⁶]octadec-7-ene-4-carboxylic acid (12) following the procedure reported for synthesis of N-[17-[2-ethoxy-7-methoxy-8-methylquinolin-4-yloxy]-13-methyl-2,14-dioxo-3,13-diazatricyclo-[13.3.0.0⁴,⁶]octadec-7-ene-4-carbonyl](cyclopropyl)sulfonamide (3): m/z=639 (M+H)⁺.

Example 13

Preparation of 17-[8-ethoxy[1,3]dioxolo[4,5-h]quinolin-6-yloxy]-13-methyl-2,14-dioxo-3,13-diazatricyclo[13.3.0.0⁴,⁶]octadec-7-ene-4-carboxylic acid (14)

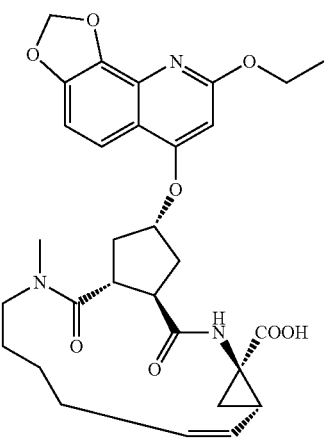

The title compound (14) was prepared from benzo[1,3]dioxol-4-ylamine following the procedure (Steps A-J) reported for synthesis of 17-[2-ethoxy-7-methoxy-8-methyl-quinolin-4-yloxy]-13-methyl-2,14-dioxo-3,13-diazatricyclo[13.3.0.0⁴,⁶]octadec-7-ene-4-carboxylic acid (2): m/z=566 (M+H)⁺.

Example 14

Preparation of N-[17-[8-ethoxy[1,3]dioxolo[4,5-h]quinolin-6-yloxy]-13-methyl-2,14-dioxo-3,13-diazatricyclo[13.3.0.0⁴,⁶]octadec-7-ene-4-carbonyl]-(cyclo-propyl)sulfonamide (15)

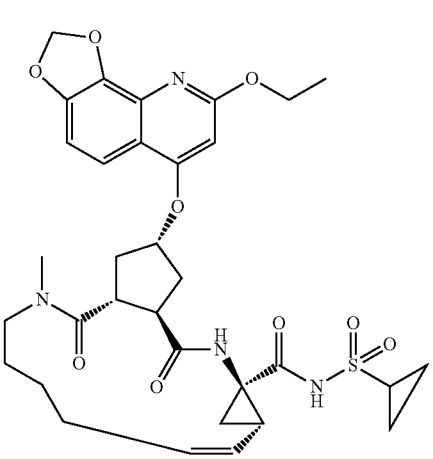

The title compound (15) was prepared from 17-[8-ethoxy[1,3]dioxolo[4,5-h]quinolin-6-yloxy]-13-methyl-2,14-dioxo-3,13-diazatricyclo[13.3.0.0⁴,⁶]octadec-7-ene-4-carboxylic acid (14) following the procedure reported for synthesis of N-[17-[2-ethoxy-7-methoxy-8-methylquinolin-4-yloxy]-13-methyl-2,14-dioxo-3,13-diazatricyclo[13.3.0.0⁴,⁶]octadec-7-ene-4-carbonyl](cyclopropyl)sulfonamide (3): m/z=669 (M+H)⁺.

Example 15

Activity of Compounds of Formula (I)

Replicon Assay

The compounds of formula (I) were examined for activity in the inhibition of HCV RNA replication in a cellular assay. The assay demonstrated that the compounds of formula (I) exhibited activity against HCV replicons functional in a cell culture. The cellular assay was based on a bicistronic expression construct, as described by Lohmann et al. (1999) Science vol. 285 pp. 110-113 with modifications described by Krieger et al. (2001) Journal of Virology 75: 4614-4624, in a multi-target screening strategy. In essence, the method was as follows.

The assay utilized the stably transfected cell line Huh-7 luc/neo (hereafter referred to as Huh-Luc). This cell line harbors an RNA encoding a bicistronic expression construct comprising the wild type NS3-NS5B regions of HCV type 1b translated from an internal ribosome entry site (IRES) from encephalomyocarditis virus (EMCV), preceded by a reporter portion (FfL-luciferase), and a selectable marker portion (neo^R, neomycine phosphotransferase). The construct is bordered by 5' and 3' NTRs (non-translated regions) from HCV type 1b. Continued culture of the replicon cells in the presence of G418 (neo^R) is dependent on the replication of the HCV RNA. The stably transfected replicon cells that express HCV RNA, which replicates autonomously and to high levels, encoding inter alia luciferase, were used for screening the antiviral compounds.

The replicon cells were plated in 384 well plates in the presence of the test and control compounds which were added in various concentrations. Following an incubation of three days, HCV replication was measured by assaying luciferase activity (using standard luciferase assay substrates and reagents and a Perkin Elmer ViewLux™ ultraHTS microplate imager). Replicon cells in the control cultures had high luciferase expression in the absence of any inhibitor. The inhibitory activity of the compound on luciferase activity was monitored on the Huh-Luc cells, enabling a dose-response curve for each test compound. $EC_{50}$ values were then calculated, which value represents the amount of the compound required to decrease by 50% the level of detected luciferase activity, or more specifically, the ability of the genetically linked HCV replicon RNA to replicate.

Inhibition Assay

The aim of this in vitro assay was to measure the inhibition of HCV NS3/4A protease complexes by the compounds of the present invention. This assay provides an indication of how effective compounds of the present invention would be in inhibiting HCV NS3/4A proteolytic activity.

The inhibition of full-length hepatitis C NS3 protease enzyme was measured essentially as described in Poliakov, 2002 Prot Expression & Purification 25 363 371. Briefly, the hydrolysis of a depsipeptide substrate, Ac-DED(Edans)EEA-buψ[COO]ASK(Dabcyl)-NH$_2$ (AnaSpec, San José, USA), was measured spectrofluorometrically in the presence of a peptide cofactor, KKGSVVIVGRIVLSGK (Åke Engström, Department of Medical Biochemistry and Microbiology, Uppsala University, Sweden) (Landro, 1997 Biochem 36 9340-9348). The enzyme (1 nM) was incubated in 50 mM HEPES (4-(2-hydroxyethyl)-1-piperazineethanesulfonic acid) pH 7.5, 10 mM dithiothreitol, 40% glycerol, 0.1% n-octyl-D-glucoside, with 25 μM NS4A cofactor and inhibitor at 30° C. for 10 min, whereupon the reaction was initiated by addition of 0.5 μM substrate. Inhibitors were dissolved in DMSO, sonicated for 30 sec and vortexed. The solutions were stored at −20° C. between measurements.

The final concentration of DMSO in the assay sample was adjusted to 3.3%. The rate of hydrolysis was corrected for inner filter effects according to published procedures (Liu, 1999 Analytical Biochemistry 267 331-335). $K_i$ values were estimated by non-linear regression analysis (GraFit, Erithacus Software, Staines, MX, UK), using a model for competitive inhibition and a fixed value for $K_m$ (0.15 μM). A minimum of two replicates was performed for all measurements.

The following Table 1 lists compounds that were prepared according to any one of the above examples. The dotted line in the structures in the column $R^9$ represents the bond by which the group is linked to the remainder of the molecule. The activities of the compounds tested are also depicted in Table 1.

| Comp. nr. | —$R^1$ | —$R^9$ | $EC_{50}$ (μM) Replicon assay | $K_i$ (μM) Enzymatic assay |
|---|---|---|---|---|
| 2 | OH | 7-methoxy-8-methyl-2-ethoxyquinoline (linked at 4-position) | 1.06 | 0.037 |
| 3 | —NH—S(=O)$_2$—cyclopropyl | 7-methoxy-8-methyl-2-ethoxyquinoline (linked at 4-position) | 0.0043 | 0.0001 |

-continued
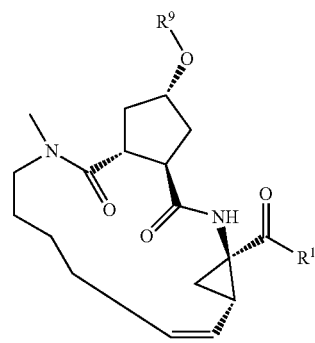
| Comp. nr. | —R¹ | —R⁹ | EC$_{50}$ (μM) Replicon assay | K$_i$ (μM) Enzymatic assay |
|---|---|---|---|---|
| 4 | OH | 7-methoxy-2-ethoxyquinolin-4-yl | 4.26 | 0.046 |
| 5 | —NH—S(=O)$_2$—cyclopropyl | 7-methoxy-2-ethoxyquinolin-4-yl | 0.014 | 0.0001 |
| 7 | —NH—S(=O)$_2$—cyclopropyl | 8-bromo-7-methoxy-2-ethoxyquinolin-4-yl | 0.0035 | 0.0001 |
| 9 | —NH—S(=O)$_2$—cyclopropyl | 2,3-dihydrofuro-2-ethoxyquinolin-4-yl | 0.029 | 0.0008 |
| 10 | OH | 8-chloro-2-ethoxyquinolin-4-yl | 3.81 | 0.0077 |
| 11 | —NH—S(=O)$_2$—cyclopropyl | 8-chloro-2-ethoxyquinolin-4-yl | 0.0063 | 0.0005 |

-continued
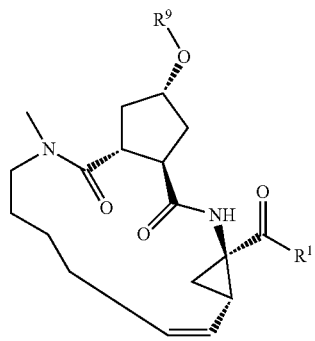
| Comp. nr. | —R¹ | —R⁹ | $EC_{50}$ (μM) Replicon assay | $K_i$ (μM) Enzymatic assay |
|---|---|---|---|---|
| 12 | OH | 8-methyl-2-ethoxyquinolin-4-yl | 7.5 | 0.017 |
| 13 | —NH—S(=O)₂—cyclopropyl | 8-methyl-2-ethoxyquinolin-4-yl | 0.014 | 0.0001 |
| 14 | OH | 2-ethoxy-[1,3]dioxolo-quinolin-4-yl | 3.3 | 0.058 |
| 15 | —NH—S(=O)₂—cyclopropyl | 2-ethoxy-[1,3]dioxolo-quinolin-4-yl | 0.0035 | 0.0002 |

The invention claimed is:
1. A compound having the formula

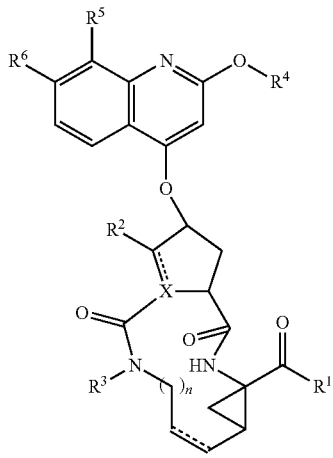

(I)

and the salts and stereoisomers thereof, wherein
each dashed line (represented by -----) independently represents an optional double bond;
X is N, CH and where X bears a double bond it is C;
$R^1$ is —$OR^7$;
$R^2$ is hydrogen, and where X is C or CH, $R^2$ may also be $C_{1-6}$alkyl;
$R^3$ is hydrogen, $C_{1-6}$alkyl, $C_{1-6}$alkoxy$C_{1-6}$alkyl, $C_{3-7}$cycloalkyl;
n is 3, 4, 5, or 6;
$R^4$ is $C_{1-6}$alkyl or $C_{3-7}$cycloalkyl;
$R^5$ represents hydrogen, halo, $C_{1-6}$alkyl, hydroxy, $C_{1-6}$alkoxy, polyhalo$C_{1-6}$alkyl;
$R^6$ represents hydrogen, $C_{1-6}$alkoxy, mono- or di$C_{1-6}$alkylamino; or
$R^5$ and $R^6$ may optionally, together with the carbon atoms to which they are attached, form a 5- or 6-membered unsaturated or partially unsaturated ring, and wherein said ring may optionally comprise one or two heteroatoms selected from O, N and S;
$R^7$ is hydrogen; $C_{3-7}$cycloalkyl optionally substituted with $C_{1-6}$alkyl; or $C_{1-6}$alkyl optionally substituted with $C_{3-7}$cycloalkyl.

2. A compound according to claim 1, wherein the compound has the formula (I-c) or (I-d):

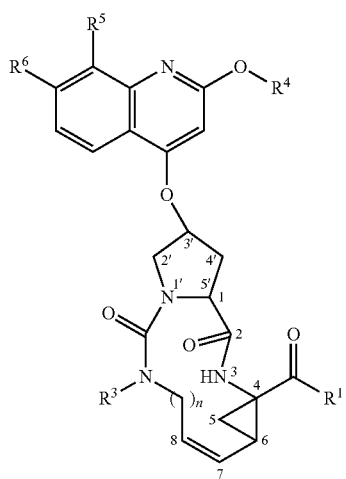

(I-c)

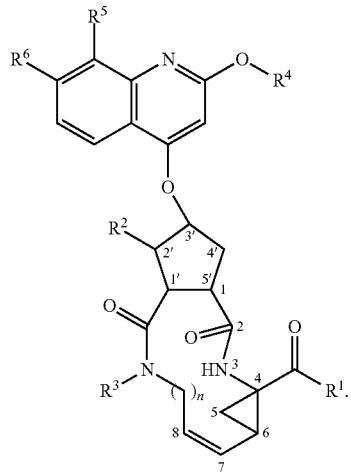

(I-d)

3. A compound according to claim 1, wherein $R^1$ is —$OR^7$, wherein $R^7$ is $C_{1-6}$alkyl or hydrogen.
4. A compound according to claim 1, wherein n is 4 or 5.
5. A compound according to claim 1, wherein $R^3$ is hydrogen or $C_{1-6}$alkyl.
6. A compound according to claim 1, wherein $R^5$ is hydrogen, methyl, ethyl, isopropyl, tert-butyl, fluoro, chloro, bromo, or trifluoromethyl.
7. A compound according to claim 1, wherein $R^6$ is hydrogen or methoxy.
8. A compound having the formula

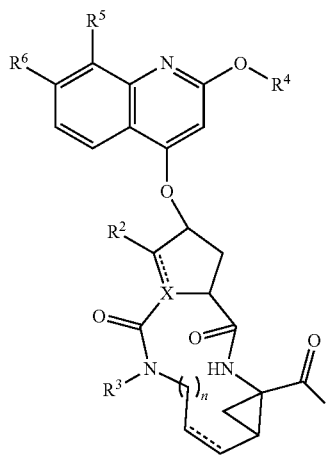

(I)

and the salts and stereoisomers thereof, wherein
each dashed line (represented by -----) independently represents an optional double bond;
X is N, CH and where X bears a double bond it is C;
$R^1$ is —NH—$SO_2R8$;
$R^2$ is hydrogen, and where X is C or CH, $R^2$ may also be $C_{1-6}$alkyl;
$R^3$ is hydrogen, $C_{1-6}$alkyl, $C_{1-6}$alkoxy$C_{1-6}$alkyl, $C_{3-7}$cycloalkyl;
n is 3, 4, 5, or 6;
$R^4$ is $C_{1-6}$alkyl or $C_{3-7}$cycloalkyl;
$R^5$ represents hydrogen, halo, $C_{1-6}$alkyl, hydroxy, $C_{1-6}$alkoxy, polyhalo$C_{1-6}$alkyl;

$R^6$ represents hydrogen, $C_{1-6}$alkoxy, mono- or di$C_{1-6}$alkylamino; or $R^5$ and $R^6$ may optionally, together with the carbon atoms to which they are attached, form a 5- or 6-membered unsaturated or partially unsaturated ring, and wherein said ring may optionally comprise one or two heteroatoms selected from O, N and S;

$R^7$ is hydrogen; $C_{3-7}$cycloalkyl optionally substituted with $C_{1-6}$alkyl; or $C_{1-6}$alkyl optionally substituted with $C_{3-7}$cycloalkyl;

$R^8$ is $C_{3-7}$cycloalkyl optionally substituted with $C_{1-6}$alkyl; $C_{1-6}$alkyl optionally substituted with $C_{3-7}$cycloalkyl; or —$NR^{8a}R^{8b}$, wherein $R^{8a}$ and $R^{8b}$ are, each independently, $C_{1-6}$alkyl, or $R^{8a}$ and $R^{8b}$ together with the nitrogen to which they are attached form a 5- or 6-membered saturated heterocyclic ring.

9. A compound according to claim 8, wherein $R^8$ is methyl, cyclopropyl; or cyclopropyl substituted with methyl.

10. A compound according to claim 8, wherein n is 4 or 5.

11. A compound according to claim 8, wherein $R^3$ is hydrogen or $C_{1-6}$alkyl.

12. A compound according to claim 8, wherein $R^5$ is hydrogen, methyl, ethyl, isopropyl, tert-butyl, fluoro, chloro, bromo, or trifluoromethyl.

13. A compound according to claim 8, wherein $R^6$ is hydrogen or methoxy.

* * * * *

UNITED STATES PATENT AND TRADEMARK OFFICE
CERTIFICATE OF CORRECTION

PATENT NO. : 8,637,663 B2  
APPLICATION NO. : 12/441812  
DATED : January 28, 2014  
INVENTOR(S) : Pierre Jean-Marie Bernard Raboisson et al.

Page 1 of 1

It is certified that error appears in the above-identified patent and that said Letters Patent is hereby corrected as shown below:

In the Claims:

Column 77, line 41, after ...selected from, delete "0" and insert -- O --.

Column 78, line 59, after ...$SO_2$, delete "R8" and insert -- $R^8$ --.

Signed and Sealed this  
Third Day of February, 2015

Michelle K. Lee  
*Deputy Director of the United States Patent and Trademark Office*